United States Patent [19]
Shue et al.

[11] Patent Number: 5,869,488
[45] Date of Patent: Feb. 9, 1999

[54] PIPERAZINO DERIVATIVES AS NEUROKININ ANTAGONISTS

[75] Inventors: Ho-Jane Shue, Pine Brook; Neng-Yang Shih; David J. Blythin, both of North Caldwell; Xiao Chen, Edison; John J. Piwinski, Clinton Township; Kevin D. McCormick, Edison, all of N.J.

[73] Assignee: Schering Corporation, Kenilworth, N.J.

[21] Appl. No.: 703,154

[22] Filed: Aug. 29, 1996

Related U.S. Application Data

[63] Continuation-in-part of Ser. No. 663,880, which is a continuation-in-part of PCT/US96/05660 May 1, 1996, Pat. No. 5,795,894.

[60] Provisional application No. 60/003,048 Aug. 31, 1995.

[51] Int. Cl.$^6$ ................. A61K 31/495; C07D 401/12; C07D 403/12
[52] U.S. Cl. ................. 514/252; 514/212; 540/598; 544/360; 544/364; 544/362; 544/365; 544/367; 544/373
[58] Field of Search ................. 544/362, 373, 544/364, 367; 514/253, 212; 540/598

[56] References Cited

U.S. PATENT DOCUMENTS

| | | | |
|---|---|---|---|
| 4,935,419 | 6/1990 | Bjork et al. | 514/231.5 |
| 5,350,852 | 9/1994 | Emonds-Alt et al. | 544/336 |
| 5,464,788 | 11/1995 | Bock et al. | 514/252 |
| 5,654,316 | 8/1997 | Carruthers et al. | 514/307 |
| 5,688,960 | 11/1997 | Shankar | 546/202 |
| 5,691,362 | 11/1997 | McCormick et al. | 514/339 |
| 5,719,156 | 2/1998 | Shue et al. | 514/255 |

FOREIGN PATENT DOCUMENTS

| | | |
|---|---|---|
| 655442 | 5/1995 | European Pat. Off. |
| 2230262 | 10/1990 | United Kingdom. |
| WO 92/20661 | 11/1992 | WIPO. |
| WO 94/13646 | 6/1994 | WIPO. |
| 9429309 | 12/1994 | WIPO. |
| WO 96/10568 | 4/1996 | WIPO. |

OTHER PUBLICATIONS

Frossaro et al, *Life Sciences* 49, pp. 1941–1953 (1991).
Teixeira et al, *Eur. J. Pharmacol.*, 311 (1996), pp. 7–14.
Picard et al, *Eur. J. Pharmacol.*, 232 (1993), pp. 255–261.
Fleetwood–Walker et al, *Eur. J. Pharmacol.*, 242 (1993), pp. 173–181.
Stratton et al, *Eur. J. Pharmacol.*, 250 (1993), pp. R11–R12.
Walsh et al, *Psychopharmacology*, 121 (1995), pp. 186–191.
Lecci et al, *Neuroscience Let.*, 129 (1991), pp. 299–302.
*J. Med. Chem.*, 9 (1966), p. 181, Roderick et al.
Maggi et al, *Eur. J. Pharmacol.*, 166, (1989), pp. 435–440.
Ellis et al, *J. Pharmacol. Exp. Ther.*, 267, 1 (1993), pp. 95–101.
Furchgott, *Pharm. Rev.*, 7 (1955), PP. 183–265.
Arunlakshana et al, *Brit. J. Pharmacol.*, 14, 48 (1959), pp. 48–58.
Danko et al, *Pharmacol. Comm.*, 1, 3 (1992), pp. 203–209.

*Primary Examiner*—Emily Bernhardt
*Attorney, Agent, or Firm*—Anita W. Magatti

[57] ABSTRACT

The invention relates to compounds of the formula

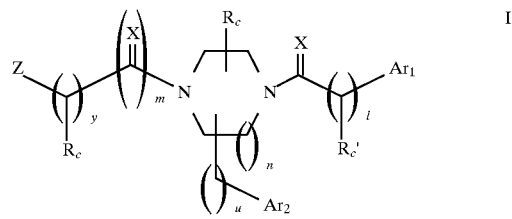

wherein Z, $R_c$, y, m, u, $Ar_2$, n, X, $R_{c'}$, l and $Ar_2$ are as described herein. These compounds are neurokinin antagonists. These compounds are useful in the treatment of chronic airway diseases such as asthma.

6 Claims, No Drawings

PIPERAZINO DERIVATIVES AS NEUROKININ ANTAGONISTS

This application is a continuation-in part of U.S. Ser. No. 08/663,880, filed Jun. 14,1996, which is continuation-in part of International Application No. PCT/US96/05660, filed May 1,1996, which claims the benefit of U.S. Provisional Application No. 60/003048, filed Aug. 31, 1995.

BACKGROUND OF THE INVENTION

The present invention relates to a genus of compounds useful as antagonists of neurokinin receptors. In particular, these can be neurokinin-1 receptor ($NK_1$) antagonists. Some can also be neurokinin-1 receptor ($NK_1$)antagonists and neurokinin-2 receptor ($NK_2$) antagonists, that is, $NK_1/NK_2$ dual receptor antagonists. Some can also be neurokinin-2 receptor ($NK_2$) antagonists. Some can also be neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example pulmonary disorders like asthma, cough, bronchospasm, chronic obstructive pulmonary diseases, and airway hyperreactivity; skin disorders and itch, for example, atopic dermatitis, and cutaneous wheal and flare; neurogenic inflammation inflammatory diseases such as arthritis, migraine, nociception; CNS diseases such as anxiety, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Moreover, $NK_3$ receptor antagonists are especially useful in the treatment and prevention of asthma, inflammatory diseases and conditions, such as ocular inflammation, allergic rhinitis, cutaneous wheal and flare, psoriasis, atopic dermatitis, CNS diseases such as anxiety and Parkinson's disease.

SUMMARY OF THE INVENTION

The invention relates to compounds of the formula:

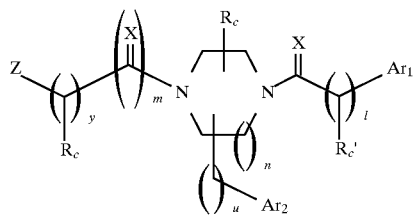

each X is independently, O, (H,H), $NR_d$, or S;
n is 0 to 2; u is 0 to 2; I is 0 to 2;
m is 1, and y is 1 to 3; or m is 2, and y is 0;
and with the further proviso that no more than one $R_c$ is other than H in the

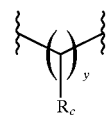

moiety;
each $R_c$ is independently H, $C_1$–$C_6$ alkyl, —$(CH_2)_{n1}$—R4 where $n_1$ is 1 to 6; $R_d$ is independently selected from the group consisting of H, $C_1$–$C_6$ alkyl, CN, $OR_a$, phenyl, substituted phenyl, benzyl, substituted benzyl, or allyl;

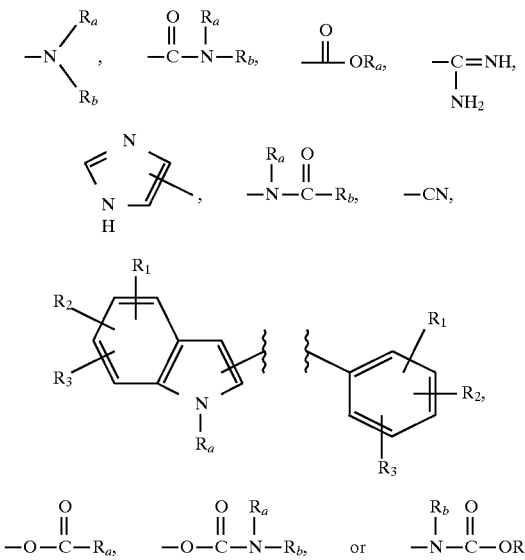

$R_c'$ is H, $C_{1-C6}$ alkyl or $(CH_2)_nOR_a$, with the proviso that no more than one $R_{c'}$ is other than H;
each $R_a$ and $R_b$ is independently selected from the group consisting of H, $C_{1-C6}$ alkyl, phenyl, substituted phenyl, benzyl, substituted benzyl, allyl; with the proviso that when $R_4$ is

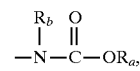

$R_a$ is not H; or when $R_a$ and $R_b$ are attached to the same nitrogen, then $R_a$ and $R_b$ together with the nitrogen to which they are attached, form a 4 to 7 member ring;
wherein each $R_1$ and $R_2$ is independently H, $C_1$–$C_6$ alkyl, $CF_3$,

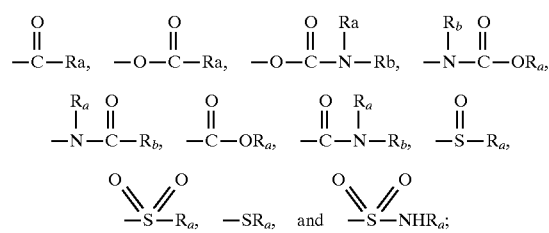

and where $R_a$ is not H

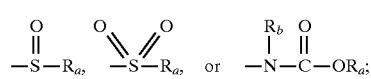

or when $R_1$ and $R_2$ are on adjacent carbons on a ring, they can form

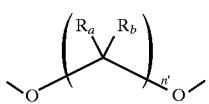

wherein n' is 1 or 2;
and each $R_3$ is independently H, $C_{1-C6}$ alkyl, $CF_3$, $C_2F_5$,

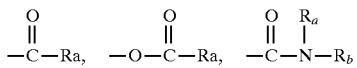

Cl, Br, I, F, $OR_a$, $OCF_3$, or phenyl;

$Ar_1$ is heteroaryl or substituted heteroaryl,

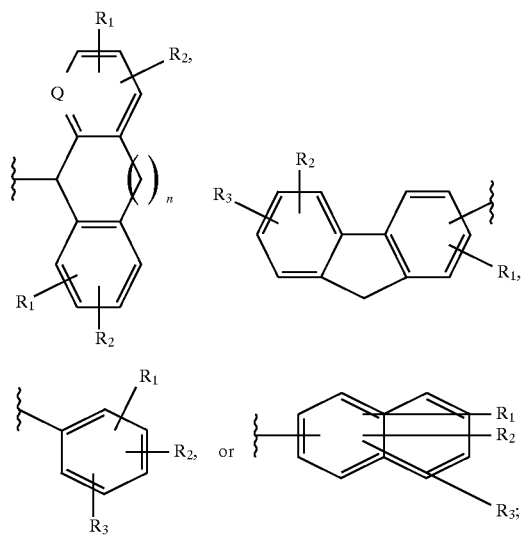

or

Q is N or CH;

$Ar_2$ is heteroaryl or substituted heteroaryl;

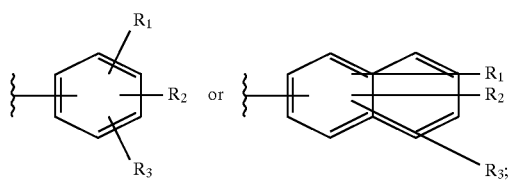

Z is

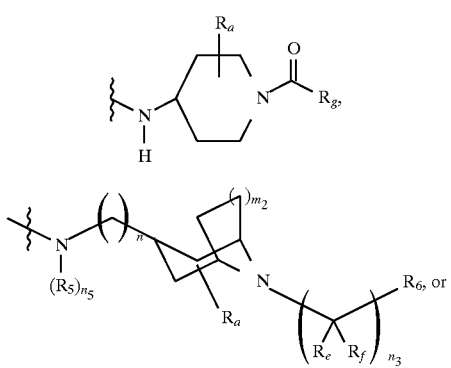

-continued

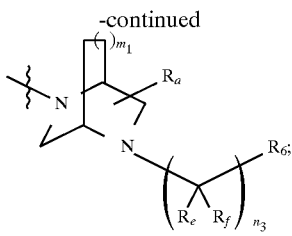

$m_1 = 0-1$; $m_2 = 1-2$; $n_3$ is 0–4;

$R_g$ is —$OR_a$ with the proviso that $R_a$ is not H; aryl, substituted aryl, heteroaryl, substituted heteroaryl, —$NR_aR_b$, —O—$(CR_a,R_b)^n{}_7$-aryl, —O—$(CR_a,R_b)^n{}_7$-substituted aryl, —O—$(CR_a,R_b)^n{}_7$-heteroaryl, —O—$(CR_a,R_b)^n{}_7$-substituted heteroaryl, —$NR_a$—$(CR_a,R_b)n7$-heteroaryl, —$NR_a$—$(CR_a,R_b)n_7$-substituted heteroaryl, —O—$(CR_a,R_b)n_7$-heterocycloalkyl, —O—$(CR_a,R_b)n_7$-substituted heterocycloalkyl, —$NR_a$—$(CR_a,R_b)n_7$-aryl, —$NR_a$—$(CR_a, R_b)n_7$-substituted aryl, —$NR_a$—$(CR_a,R_b)n_7$-heterocycloalkyl, —$NR_a$—$(CR_a,R_b)n_7$-substituted heterocycloalkyl;

$n_7$ is 0 to 4;

each $R_e$ and $R_f$ is independently selected from the group consisting of H, $C_1-C_6$ alkyl, phenyl, substituted phenyl, benzyl, substituted benzyl, allyl; or $R_e$ and $R_f$ taken together with the carbon to which they are attached can also form a carbonyl group with the proviso that no more than one carbonyl group is in the

moiety;

$n_5$ is 1 to 2;

each $R_5$ is independently selected from the group consisting of H, OH,

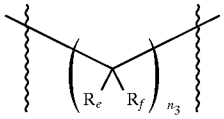

$C_1-C_6$ alkyl, $(CH_2)_{n1}$—$R_4$ wherein $n_1$ is 1 to 6 with the proviso that when $n_1$ is 1, $R_4$ is not OH or $NR_aR_b$; also with the proviso that when $n_5$ is 2, $R_5$ is $C_1-C_6$ alkyl, and two $R_5$ can be attached to the nitrogen to form a quaternary salt;

$R_6$ is H, $C_1-C_6$ alkyl, $C_3-C_6$ cycloalkyl,

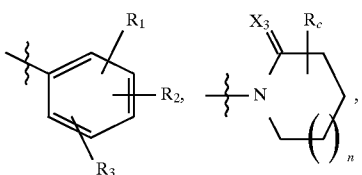

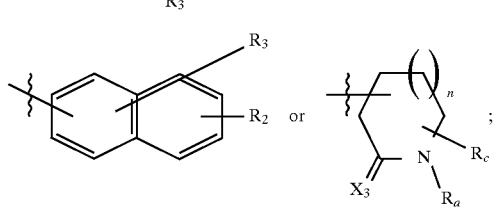

wherein $X_3$ is (H,H), O, $NRd$, or S;

or $R_6$ is heteroaryl, substituted heteroaryl, heterocycloalkyl, substituted heterocycloalkyl, when $n_3$ is 0–4;

when $R_e, R_f$ taken together with the carbon atom to which they are attached form a carbonyl group and $n_3$ is 1, $R_6$ can also be —$OR_a$ wherein $R_a$ is not H, or $R_6$ is —$NR_a,R_b$, —O—$(CR_a,R_b)n_7$-heteroaryl, —O—$(CR_a,R_b)n_7$-substituted heteroaryl, —O—$(CR_a,R_b)n_7$-heterocycloalkyl, —O—$(CR_a, R_b)n_7$-substituted heterocycloalkyl, —O—$(CR_a,R_b)n_7$-aryl, —O—$(CR_a,R_b)n_7$-substituted aryl, —$NR_a$—(CRa,Rb)n_7-heteroaryl, —$NR_a$—(CRa,Rb)n_7-substituted heteroaryl, —$NR_a$—(CRa,Rb)n_7-aryl, —$NR_a$—(CRa,Rb)n_7-substituted aryl, —$NR_a$—$(CR_a,R_b)n_7$-heterocycloalkyl, —$NR_a$—$(CR_a,R_b)n_7$-substituted heterocycloalkyl, wherein $R_a$ and $R_b$ are each independently selected from the group consisting of H and $C_1$–$C_6$ alkyl;

or any enantiomer thereof, or a pharmaceutically acceptable salt thereof.

All of the variables in the above formulas such as Z, $R_1$, $R_2$, and $R_3$, have the same meaning throughout the specification unless otherwise specified.

Preferred compounds of the invention are compounds of formula 1, wherein each X is O or (H,H) and at least one X is O.

Also preferred are compounds of formula I wherein both X's are O.

Also preferred are compounds of formula I wherein l is 0, m is 1, and y is 1–3.

Also preferred are compounds of formula I wherein n is 1 and u is 0.

Also preferred are compounds of formula I wherein $Ar_1$ is

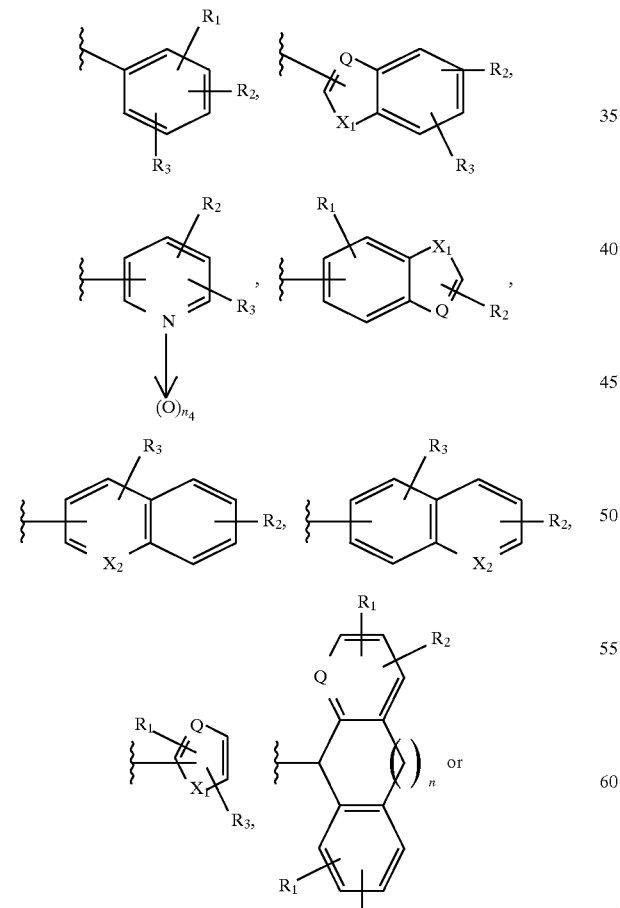

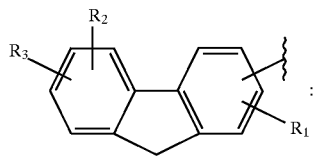

wherein Q is N or CH;

each $X_1$ is independently O, S or $NR_a$;

each $X_2$ is independently CH or N; and $n_4$ is 0 or 1.

Also preferred are compounds of formula I wherein $Ar_2$ is

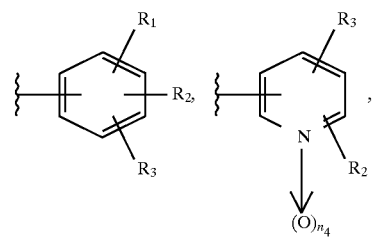

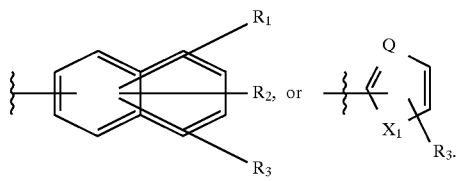

Also preferred are compounds of formula I wherein Z is

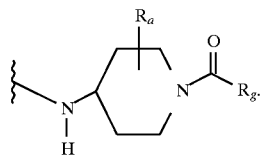

Also preferred are compounds of formula I wherein Z is

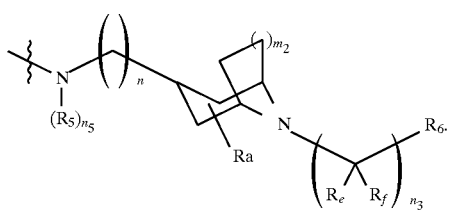

Also preferred are compounds of formula I wherein Z is

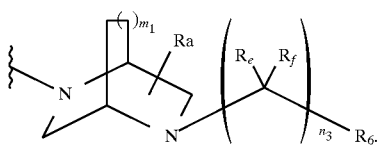

Also preferred are compounds of formula I wherein Z is

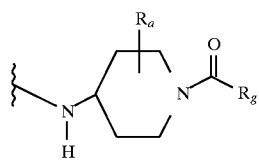

wherein $R_g$ is —ORa, —NR$_a$R$_b$, and —O—(CR$_a$,R$_b$)$^n{}_7$-heteroaryl, with the proviso that when $R_g$ is O—(CR$_a$,R$_b$)$^n{}_7$-heteroaryl, $R_a$ and $R_b$ are each independently selected from the group consisting of H and $C_1$–$C_6$ alkyl;

$n_7$ is 0 to 4.

Also preferred are compounds of formula I wherein both X's are O; l is 0; m is 1; y is 1–3; n is 1; u is 0; $Ar_1$ is

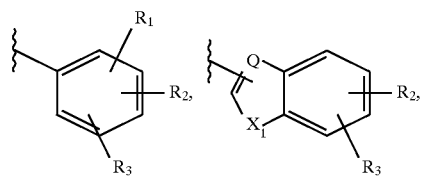

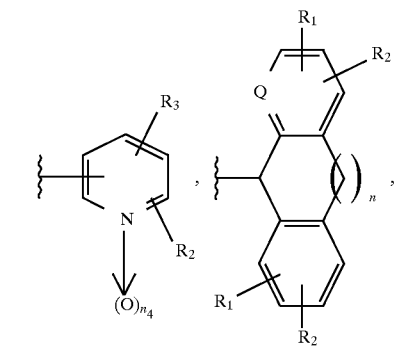

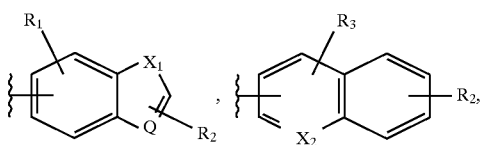

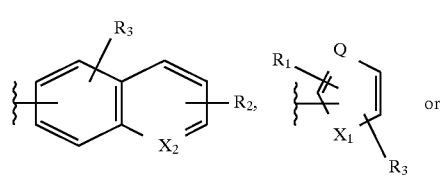

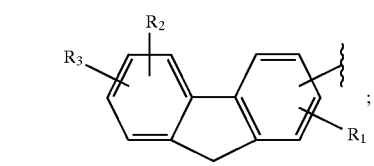

$Ar_2$ is

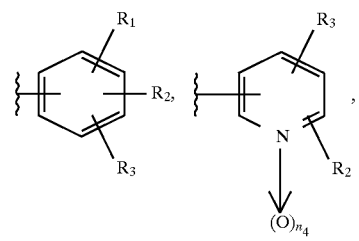

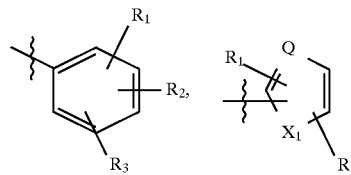

wherein $n_4$ is 0 or 1.

Z is defined in Formula I, when $R_e, R_f$ are H, $C_1$–$C_6$ alkyl, allyl, $n_3$ is 0–4 and $R_6$ is

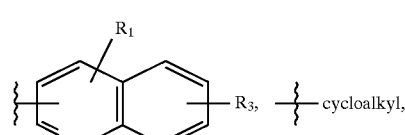

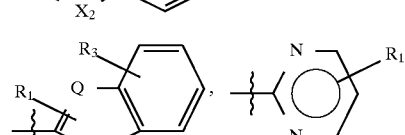

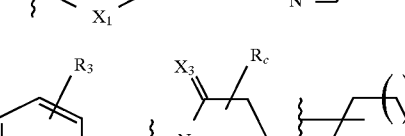

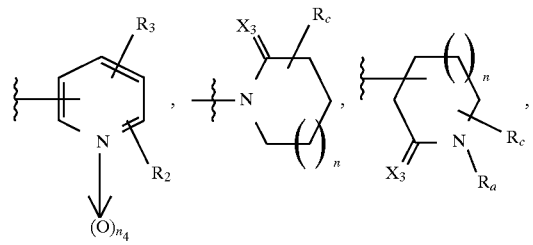

or $R_e$ and $R_f$ taken together with the carbon to which they are attached form a carbonyl group, $n_3$ is 1 and $R_6$ is —O—(CR$_a$,R$_b$)n$_7$—L, wherein L is

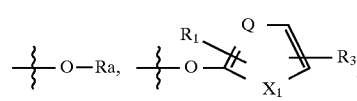

-continued $Ar_1$ and $Ar_2$ are both

[chemical structures with R groups, X, Q substituents including naphthalene, phenyl, pyridine, and pyrimidine derivatives with substituents —O-cycloalkyl, —N(H)Ra, —N-cycloalkyl(H), —cycloalkyl, —$C_1$–$C_6$ alkyl, and (O)$_{n_4}$]

or $R_e$ and $R_f$ taken together with the carbon to which they are attached form a carbonyl group, $n_3$ is 1 and $R_6$ is —O—$(CR_a,R_b)n_7$—L, wherein L is

[chemical structures: —O—Ra, —O-substituted phenyl with $R_3$, naphthalene with —O-cycloalkyl, phenyl with —N(H)Ra, and —NH-naphthalene with $R_3$]

Also preferred are compounds of formula II

[chemical structure of formula II]

where in $R_c$ is H; $m_1$ is 0 or 1; y is 1–3;

-continued
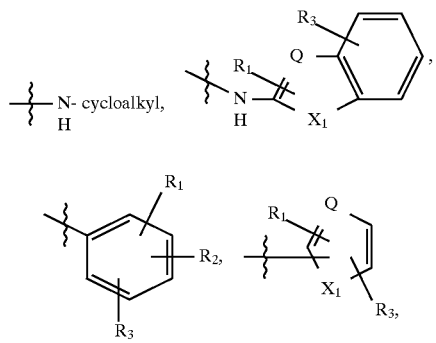
wherein Ar$_1$ and Ar$_2$ are both
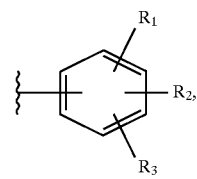
Also preferred are compounds of the invention of the formula III:
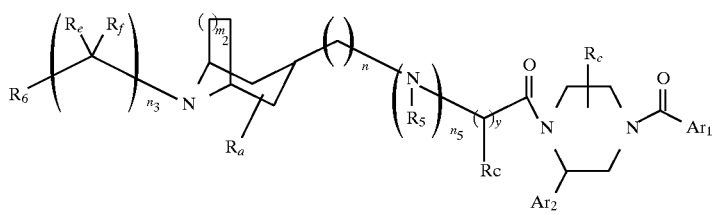
-continued
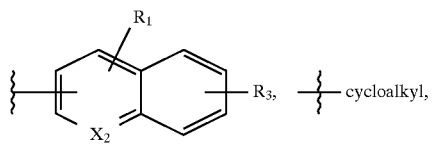
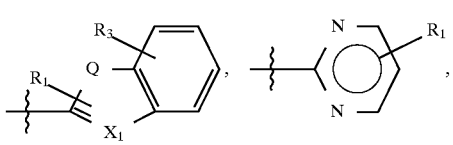
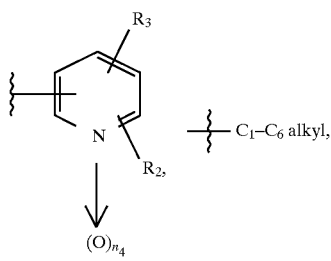
Also preferred are compounds of the invention of the formula II:
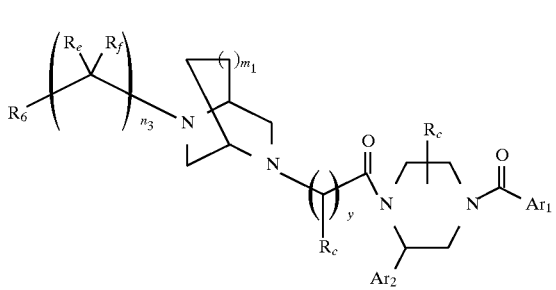
wherein Ar$_1$ and Ar$_2$ are both
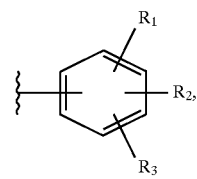
Exemplary compounds of the invention are compounds of the formulas:

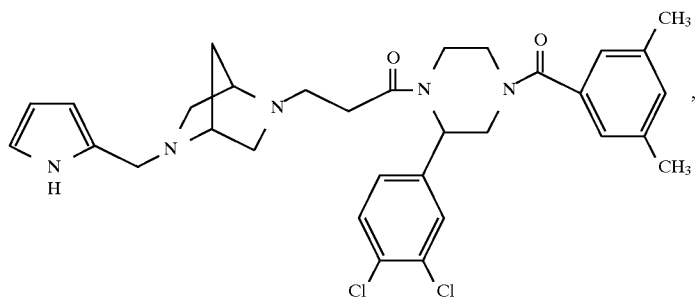
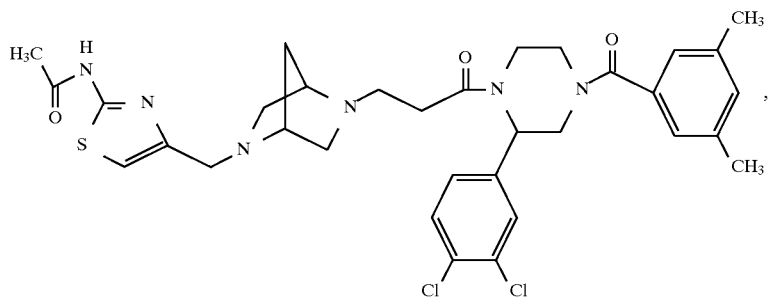
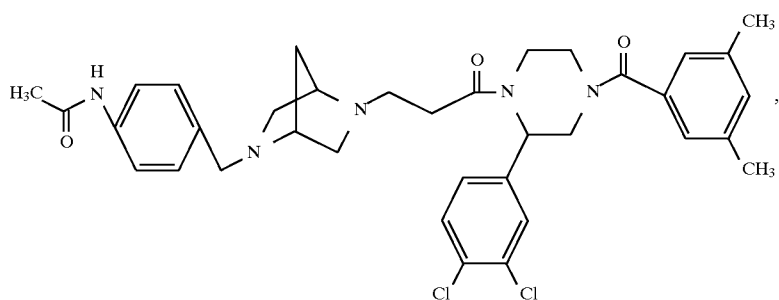
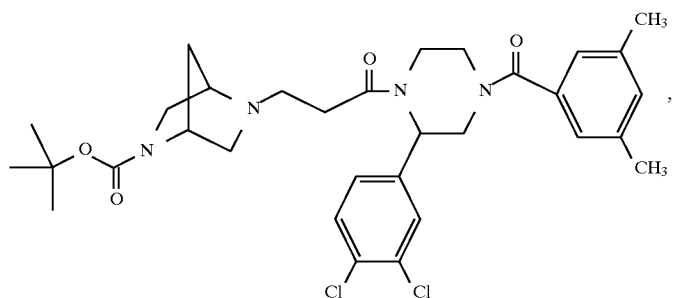
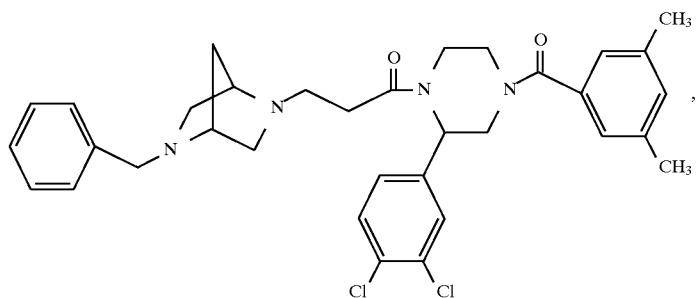

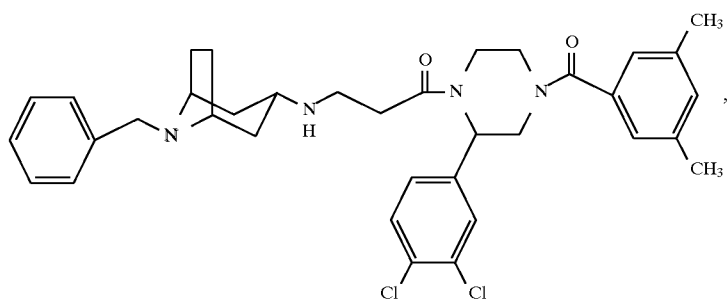
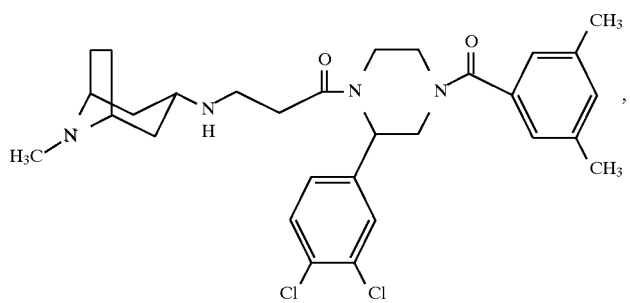
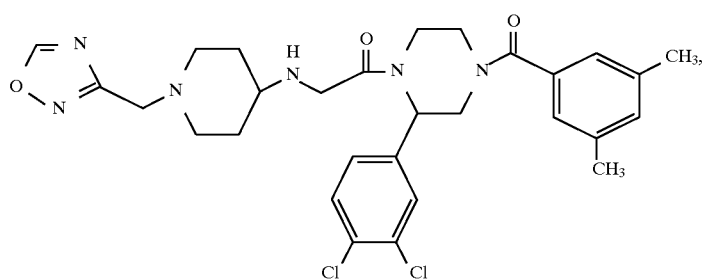
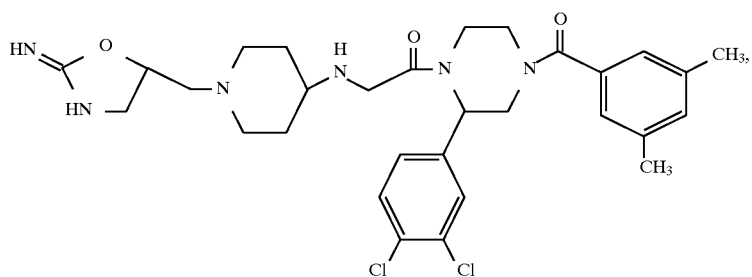
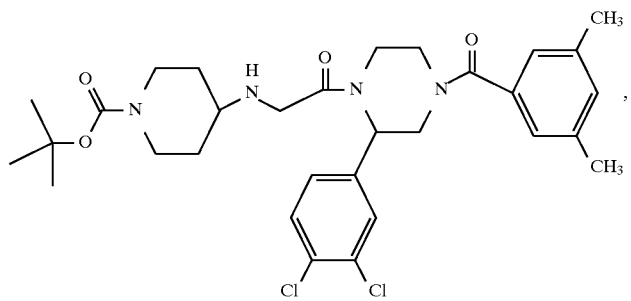

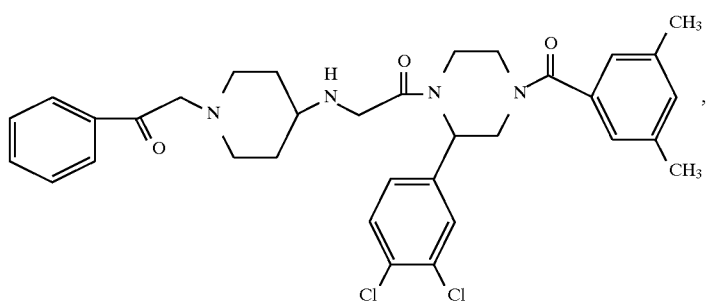,
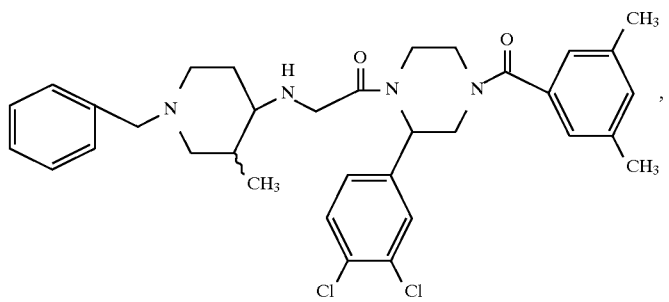,
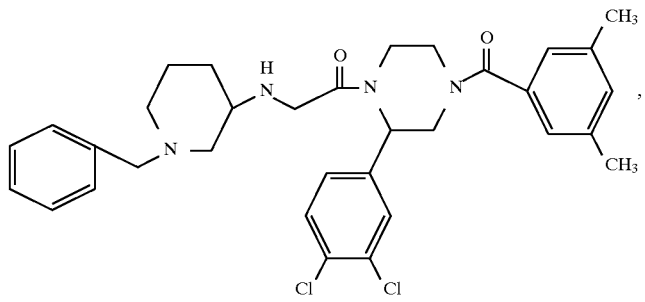,
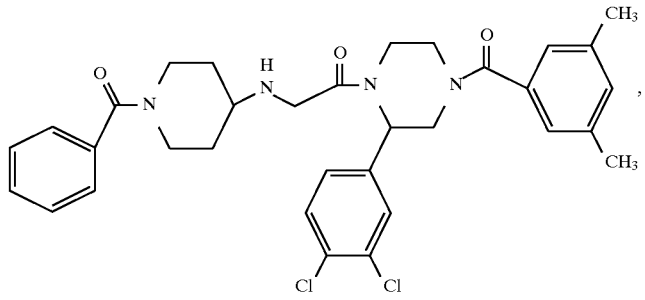,
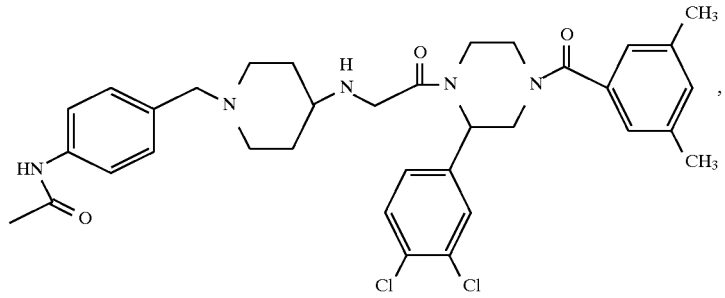,

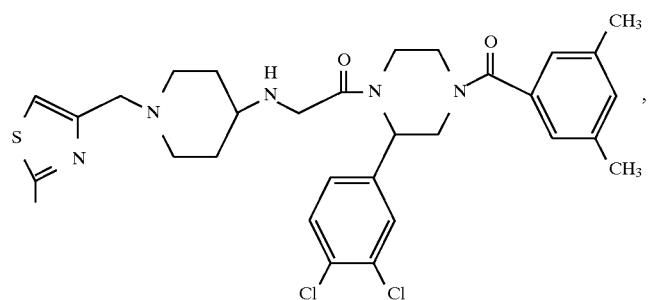
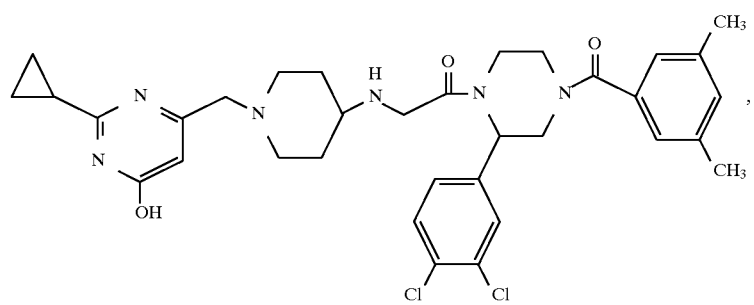
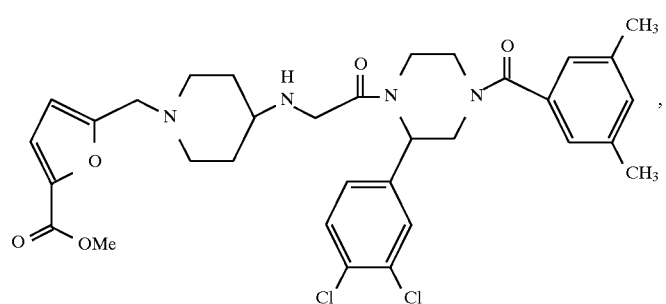
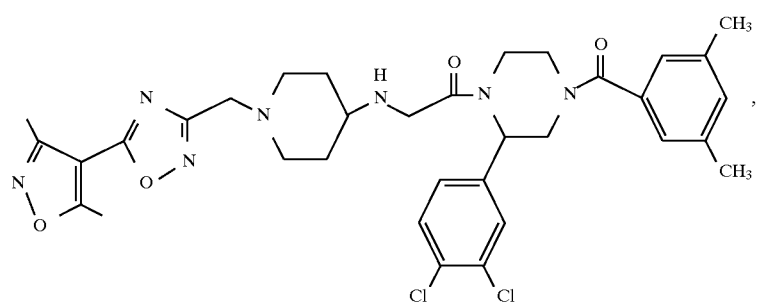
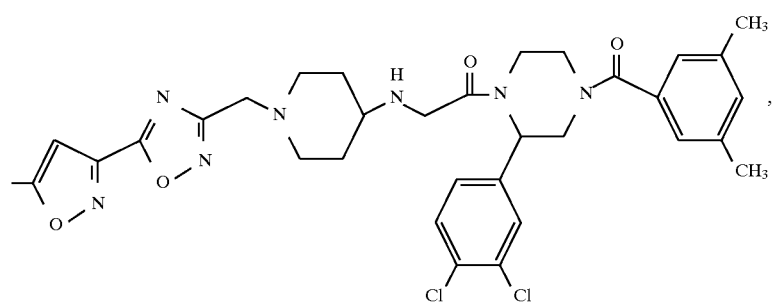

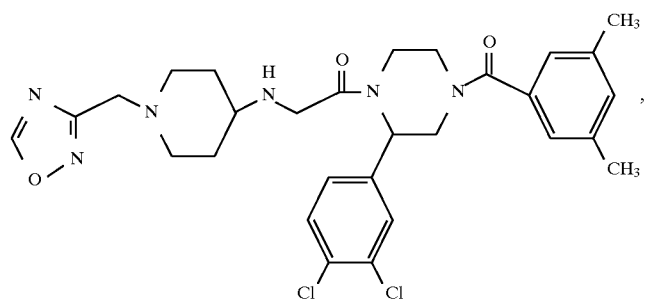
,
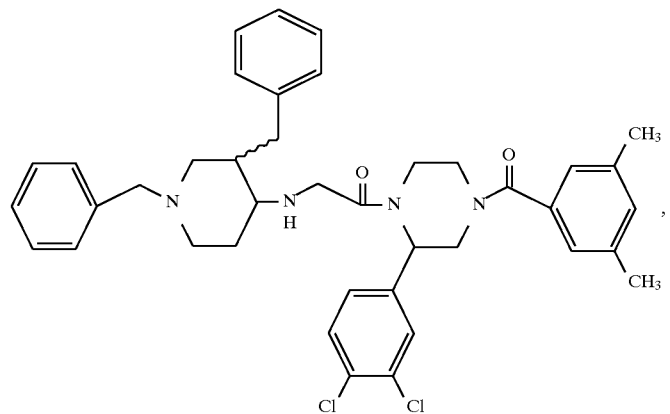
,
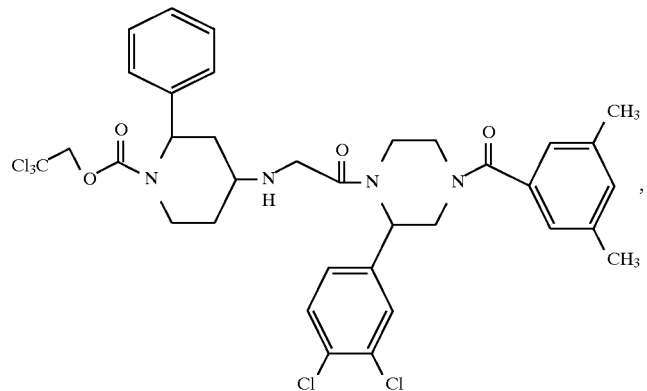
,
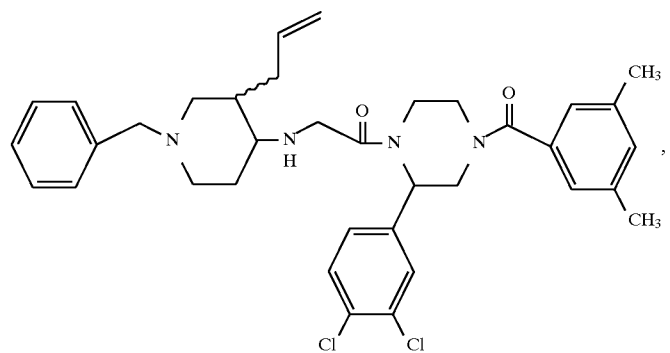
,

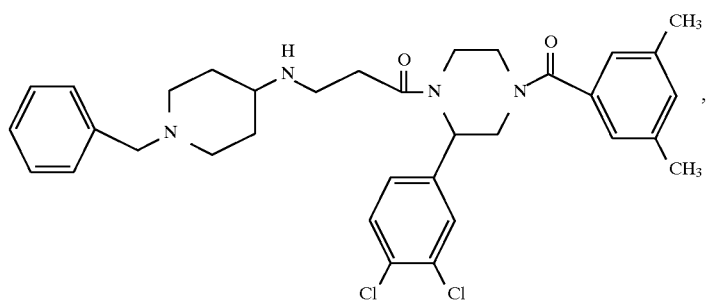
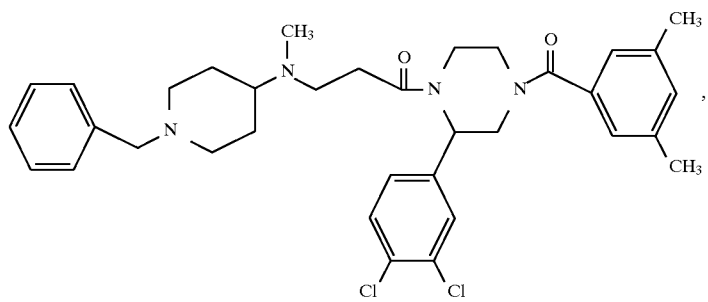
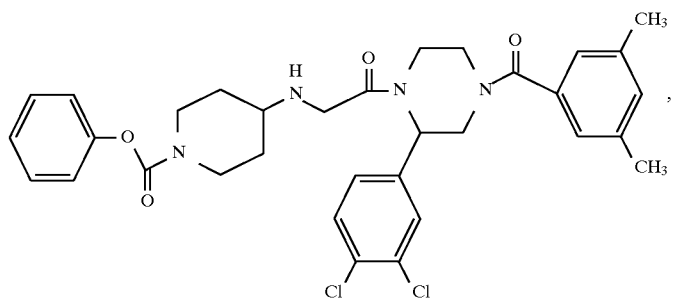
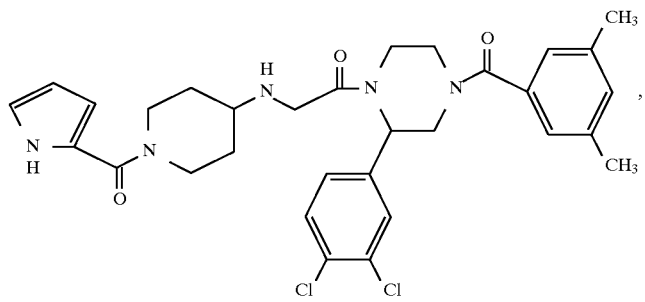
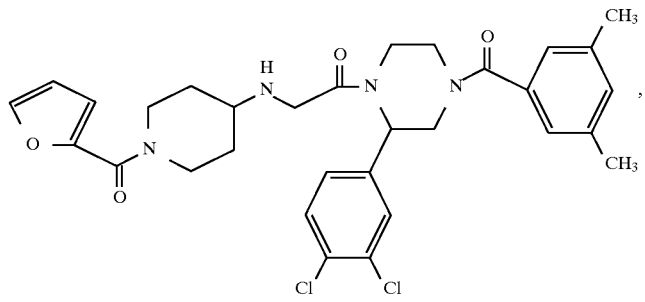

-continued
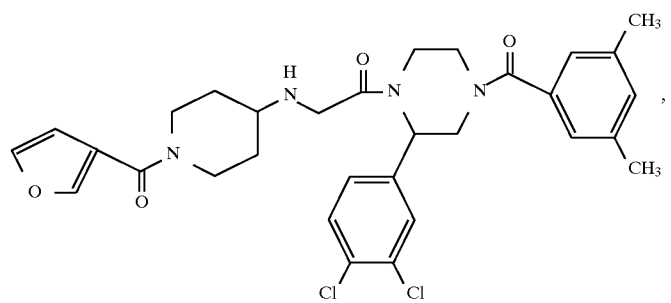
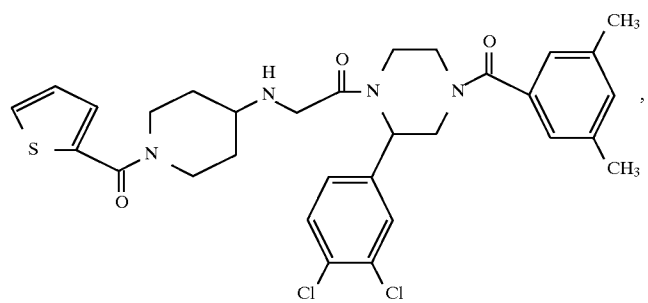
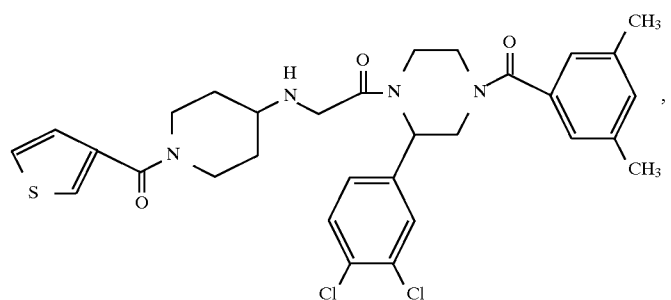
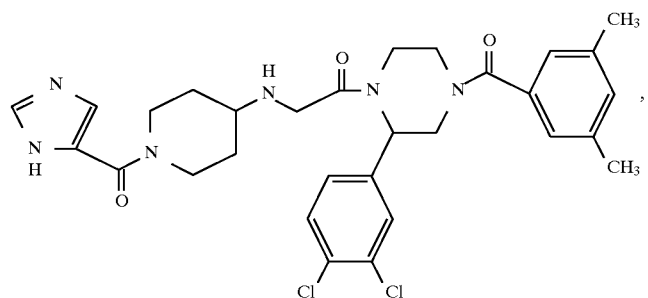
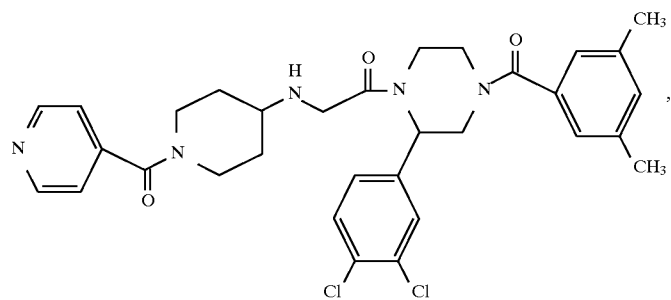

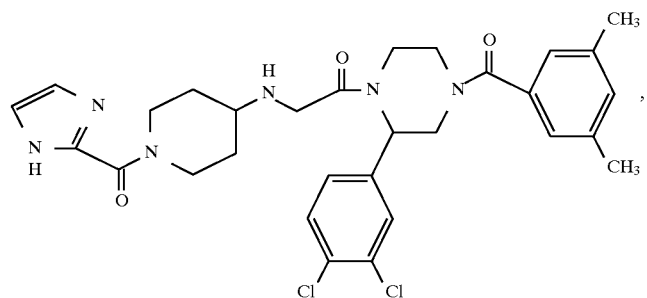
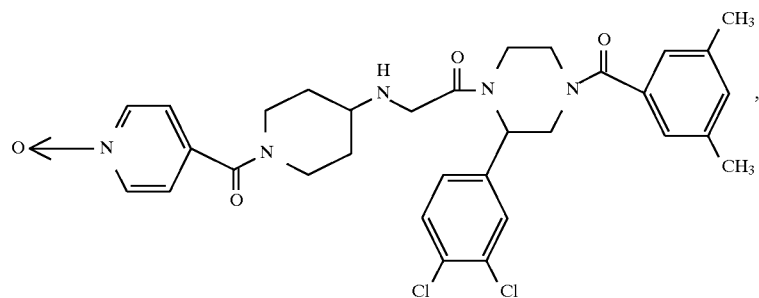
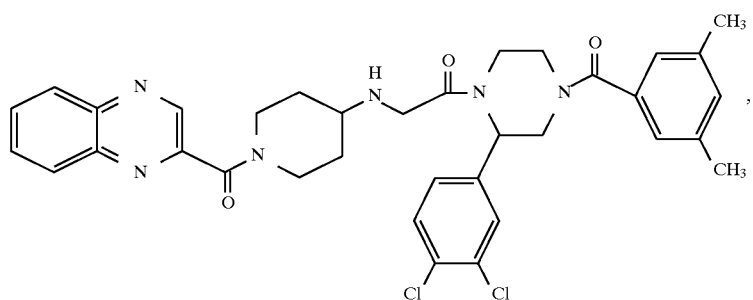
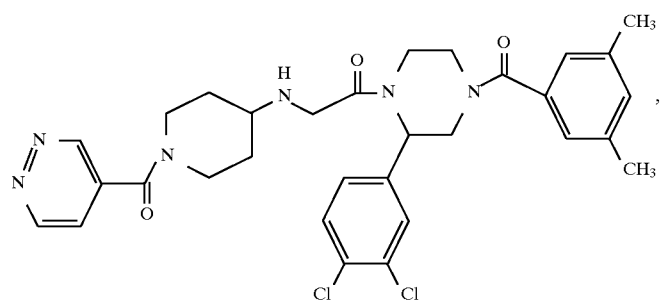
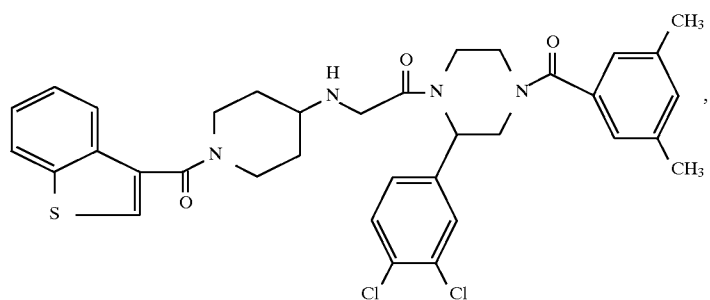

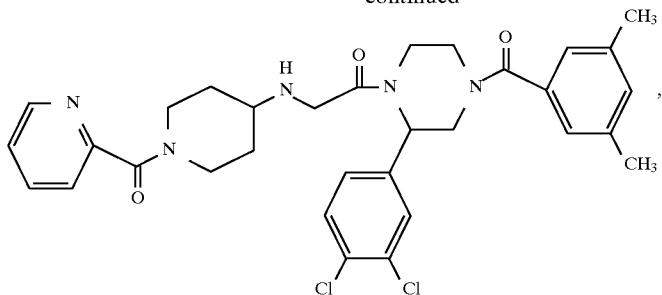

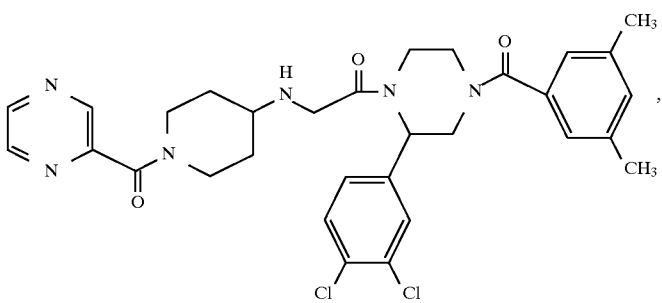

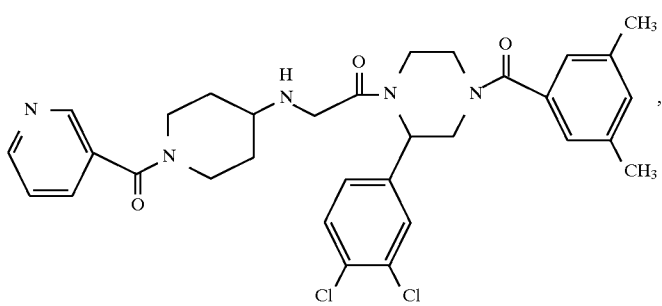

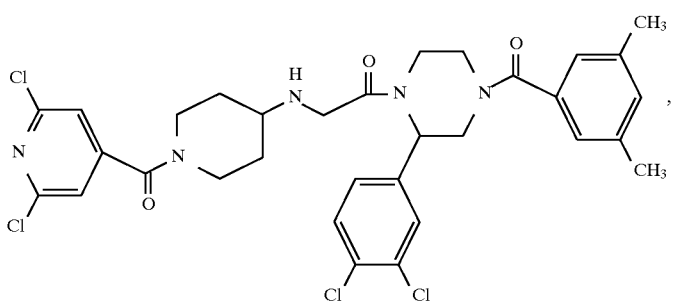

or any enantiomer thereof,
or a pharmaceutically acceptable salt thereof.

The invention also relates to a pharmaceutical composition comprising a thereapeutically effective amount of a compound of formula I in combination with a pharmaceutically acceptable carrier.

The invention also relates to a method for inducing neurokinin antagonism which comprises administering a neurokinin antagonistic effective amount of a compound of formula I to a mammal in need thereof.

The invention also relates to a method for treating chronic airway diseases such as asthma and allergies; inflammatory diseases such as inflammatory bowel disease, psoriasis, fibrositos, osteoarthritis, and rheumatoid arthritis; migraine; central nervous system disorders such as depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term $C_3$–$C_6$ cycloalkyl means a cycloalkyl having from 3 to 6 carbon atoms, that is cyclopropyl, cyclobutyl, cyclopentyl and cyclohexyl.

The term alkenyl means means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

The term alkynyl means a straight or branched alkynyl having from 2 to 6 carbon atoms. The number of carbon atoms may be designated. For example, "$C_2$–$C_6$ alkynyl" represents a straight or branched chain alkynyl having from 2 to 6 carbon atoms.

As used herein, a heavy dark line (━) denotes a chemical bond coming above the plane of the page. A dashed line (⋯) denotes a chemical bond coming below the plane of the page.

As used herein,

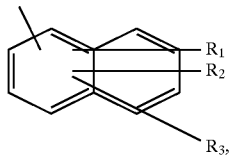

for example, means that $R_1$, $R_2$, and $R_3$ can be in either of the rings of the above naphthyl moiety.

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methanesulfonic, citric, maleic, fumaric, succinic and the like, respectively.

General Methods of Preparation

The compounds of this invention may be prepared by one of the following general methods. As used herein RT means room temperature. Unless otherwise indicated, variables in the structural formulas below are as defined above. Starting materials and reagents used in the methods and examples below, are known or may be prepared according to known methods.

As used herein the term "substituted phenyl" means

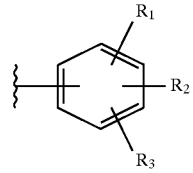

wherein $R_1$, $R_2$, and $R_3$ are as described herein.

"substituted" means substituted by $R_1$, $R_2$, and/or $R_3$ as described herein.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered rings comprising 1 to 3 heteroatoms independently selected from the group consisting of —O—, —S— and —N($R^6$)—, with the remaining ring members being carbon. Examples of heterocycloalkyl rings are tetrahydrofuranyl, pyrrolidinyl, piperidinyl, morpholinyl, thiomorpholinyl and piperazinyl.

"Heteroaryl" refers to 5- to 10-membered single or benzofused aromatic rings comprising 1 to 3 heteroatoms independently selected from the group consisting of —O—, —S— and —N═. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl.

Where $R^2$ and $R^3$ substituents form a ring and additional heteroatoms are present, the rings do not include adjacent oxygen and/or sulfur atoms or three adjacent heteroatoms. Typical rings so formed are morpholinyl, piperazinyl and piperidinyl.

As used herein, the term "BOC" means t-butoxycarbonyl.

As used herein, the term "Ph" means phenyl.

As used herein, the term "RT" means room temperature.

As used herein, the term "parallel synthesis" means the preparation of individual chemical compounds as one of a batch of, for instance, 20, 30, or even 100 identical reactions on usually a single substrate but using a different reagent in each vessel. Such reagents are always of the same general class—in this case, either carboxylic acids or organic amines in any set of parallel reactions. The conditions used for each reaction are identical to those described in the examples, except that a simplified work-up is employed, generally a simple wash either with acid or base if appropriate, then water. The presence of the product is detected by thin layer chromatography (TLC) using known products as representative standards. Further characterization by combination HPLC/MS is generally performed. No further purification is performed on these materials before they are submitted to biological assays.

As used herein, each $R_c$ and $R_{c'}$ is independently selected from the group consisting of H, $C_1$–$C_6$ alkyl, $C_2$–$C_6$ alkenyl, $C_2$–$C_6$ alkynyl, unsubstituted or substituted phenyl, and unsubstituted or substituted benzyl, The starting materials in the methods below are either known or can be prepared in accordance with known methods. In particular, the following compounds are either known or can be prepared in accordance with known methods: the diamine A, the compounds of formulas A, VI, VIII, X, XI, XIV, XVIII, XIX, XXa, A', XXV, and Z-H, as well as esters of formula XI and compounds of formula

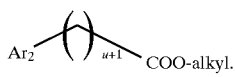

Method 1. If the group $Ar_2$ is an aromatic group with no I or Br substituents, then the following method may be used to prepare the useful intermediates (IV):

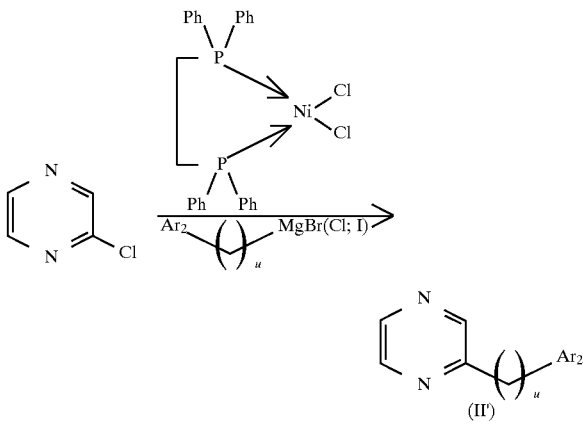

Transition metal catalyzed coupling of 2-chloropyrazine with an aromatic Grignard reagent in a dry, ether solvent, such as THF, yields the aryl-substituted pyrazine of formula II'. The catalyst shown, [1,2-bis-(diphenylphosphino) ethane]nickel$^{II}$ chloride, is a preferred reagent for this transformation. Where $Ar_2$ has no halo substituents, reduction of a compound of formula II' by catalytic hydrogenation, using, for instance, palladium acetate, preferably in acetic acid solvent, results in preferential reduction of the pyrazine ring, leaving the aromatic ring unreduced, that is, it results in a compound of formula II. Similarly, 10% Pd on charcoal (Pd—C) can be used in an alcohol solvent, preferably methanol, with or without the addition of a small quantity (1 to 5 equivalents) of acetic acid. Reaction times of about 1 to 24 hours generally suffice for this reaction, which is preferentially run at room temperature or slightly above (up to about 50° C.) and using from 1 to about 6 atmospheres pressure of hydrogen.

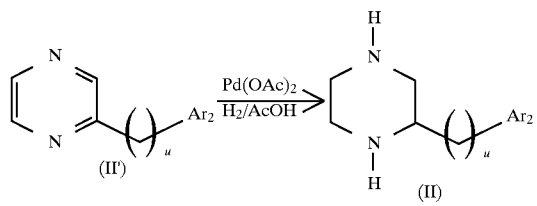

The intermediate of formula 11 may also be prepared from a compound of formula II', even if the group $Ar_2$ contains halogen atoms, by reduction using a strong hydride ion donor, preferably lithium aluminum hydride (LAH) or diisobutyl aluminum hydride (DIBAL-H) in an ether solvent, such as ether, THF or dimethoxyethane (DME).

Selective alkylation of a compound of formula II is possible using low temperature conditions. Thus, reacting a compound of formula 11 with a substituted aryl-alkyl halide of formula III where I is 0 to 2, results in the formation of the 4-substituted derivative of formula IV. Suitable conditions include use of a halogenated solvent, such as $CH_2Cl_2$, at low temperature. Suitable temperatures are from −78° C. initially, allowing the reaction mixture to warm gradually to RT if the reaction is not completed after several hours. The reaction is catalyzed by the addition of an equivalent amount of an organic base, such as triethylamine and diisopropylethylamine (Hünig's base).

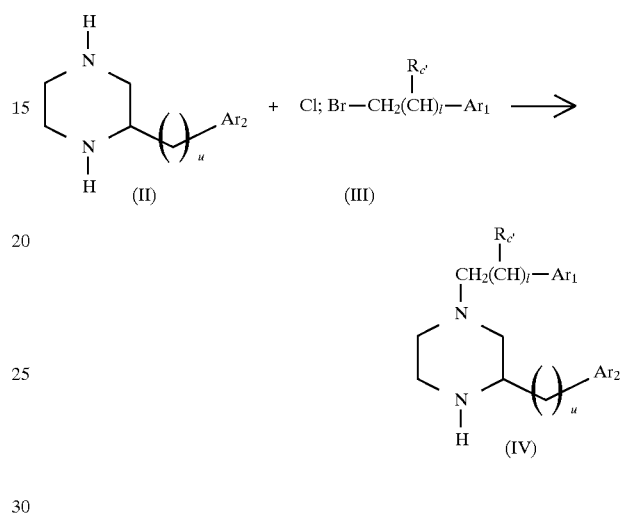

Method 2. If the group $Ar_2$ contains one or more halogen atoms on an aromatic ring and the other groups are as in Method 1, then an alternate route to a compound of formula IV is preferred. In addition, this method can be used to prepare compounds in which I is from 0 to 2. Monoprotection of the diamine of formula (A), preferably with BOC anhydride, or other agents known to introduce the t-butyloxycarbonyl protecting group, in an alcohol solvent, such as methanol, preferably at about −10° C., produces a compound of formula V.

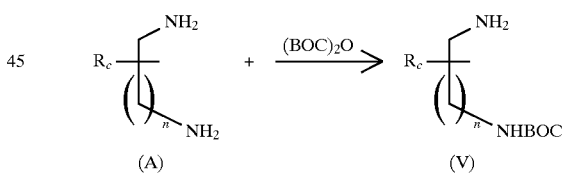

These compounds are used to perform a reductive amination reaction with the aldehyde of formula VI to produce an amine of formula VII. (In structures (A), (V), (VII), and (IX) herein, $R_c$ can be bound to any position between the two nitrogens. In cyclic structures like (IVA) below, $R_c$ can be bound to any available cyclic position that is occupied by carbon, and that is between the two nitrogens.)

Suitable conditions for this type of reaction include the use of an alcohol solvent, preferably methanol, or 2,2,2-trifluoroethanol, made slightly acidic with a weak organic acid, such as acetic acid, and a reducing agent known to favor reductive amination reactions, preferably sodium cyanoborohydride, $NaBH_3CN$.

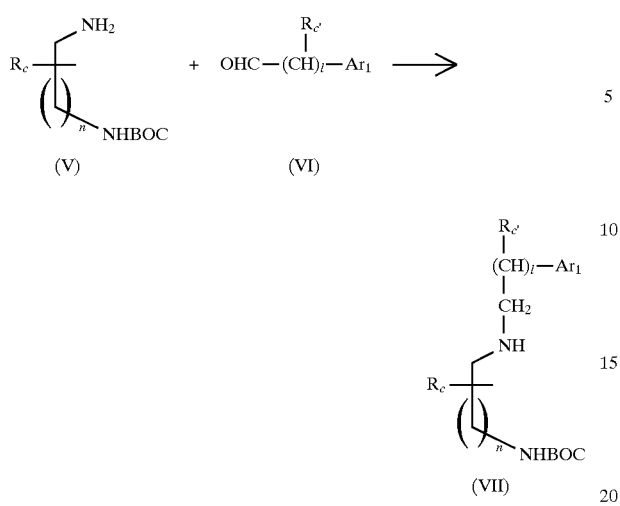

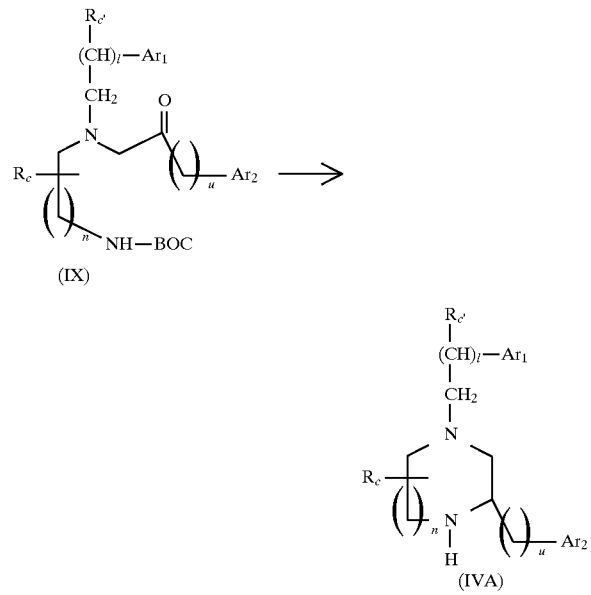

Reaction of a compound of formula VII with an α-haloketone of formula VIII, in which $Ar_2$ preferably represents a halogenated aromatic ring, but may be any of the claimed aromatic rings, in the presence of an organic base, such as di-isopropylethylamine, also known as Hünig's Base, in an ether solvent, such as THF, results in the formation of the intermediates of formula IX.

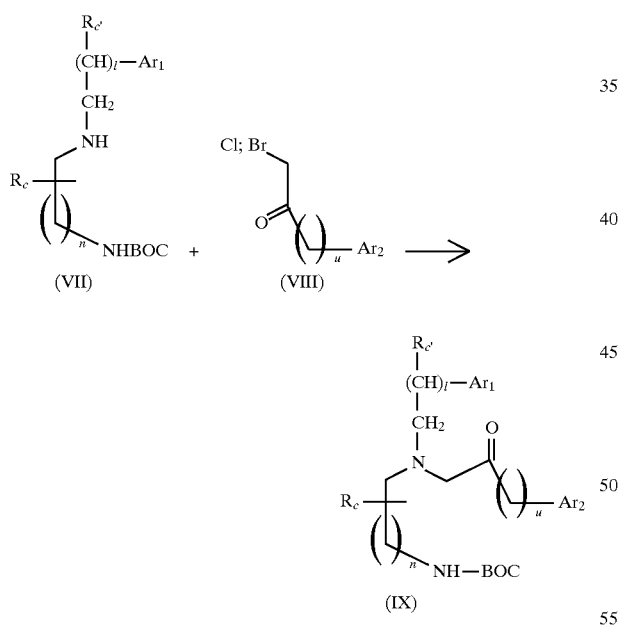

Removal of the BOC protecting group using a suitable acidic catalyst, such as trifluoroacetic acid, followed by an intramolecular reductive 5 amination, under conditions such as those described above for the preparation of a compound of formula VII, leads to the formation of compounds of formula IVA.

Method 3. An alternate route to compounds of the invention in which I is 0 to 2 is as follows. Standard coupling of an N-protected amino acid of formula X, wherein $Ar_2$ is as described above, with an amino acid ester derivative $$H_2N \overset{R_c}{\underset{}{\diagup}} COOR'$$

(R' is $C_2$–$C_4$ alkyl, preferably, the ethyl ester of formula XI, .Et in the formulas herein means ethyl), produces a dipeptide of formula XII. A suitable protecting group is BOC, although many others may also be used. Other esters of the amino acid may also be used. Standard coupling techniques may be applied, an example being the use of N-hydroxybenztriazole (HOBT) and a water-soluble carbodiimide, such as 1-(3-dimethylaminopropyl)-3-ethylcarbodiimide (DEC), in a non-hydroxylic solvent such as $CH_2Cl_2$, DMF or a mixture of the two foregoing solvents. The reaction is run, preferably, at or below RT, and takes from 1 to 40 hours for completion, depending upon the substrates.

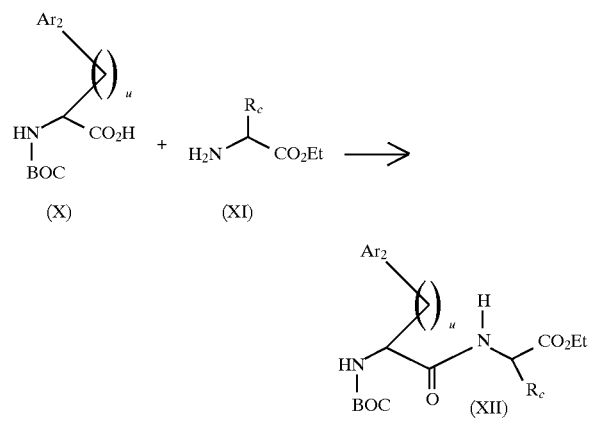

Removal of the protecting group under standard conditions, followed by treatment of the product with a base results in cyclization to the diketopiperazine of formula XIII. Suitable conditions for removal of the exemplified BOC group are well known in the art and include catalysis by trifluoroacetic acid (TFA). A suitable base for cyclization is the alkali metal salt of an alcohol in the alcohol itself used as solvent. For example, a solution of sodium ethoxide in ethanol may be used. The temperature is preferably around RT but may be slightly above or below, in the range 0° C. to about 40° C. The reaction is generally complete within a few hours. Suitable reaction times are from 1 to 24 hours.

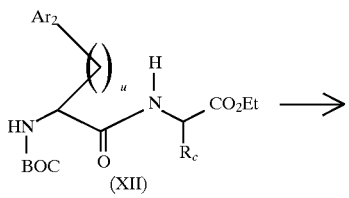

(XII)

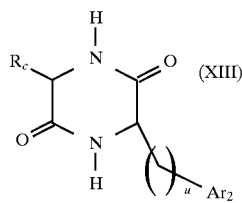

(XIII)

Reduction of the diketopiperazine of formula XIII to a compound of formula 11 may be accomplished preferentially with a strong hydride reducing agent, such as LAH or a solution of sodium bis(2-methoxy-ethoxy)aluminum hydride in toluene (also known as Red-Al®), or the $BH_3 \cdot S(CH_3)_2$ complex. Suitable solvents for this reaction are DME and other higher boiling ethers since the reaction is run at elevated temperatures, from about 50° C. to about 110° C., preferably at about 90° C.

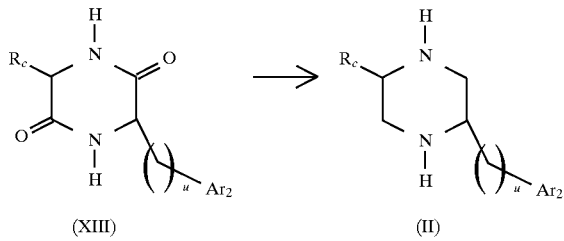

(XIII)     (II)

Alternatively, a compound of formula of 11 may be prepared by the scheme shown below (J. Med. Chem., 9, 191 (1966)). As used herein L is any readily available ester residue such as $C_1$–$C_7$ alkyl, more preferably methyl or ethyl.

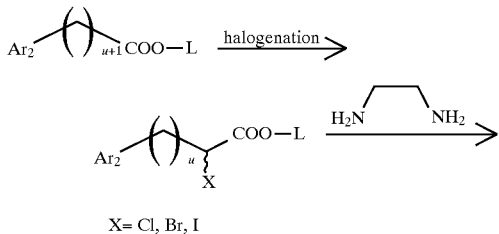

X = Cl, Br, I

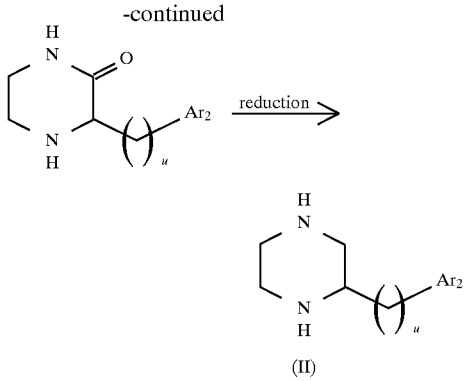

(II)

A compound of formula II may be converted to a compound of formula IV by the processes described in Method 1 above or Method 6 below.

Method 4. The intermediates of formula IV or IVA, formed via any of the previous methods, may be further processed as follows. A compound of formula IVA will be used in the Schemes. Reaction of a compound of formula IVA with an activated halo-acid, generally the acid halide of formula XIV, in which Hal represents Cl, Br, or I, yields the acylated derivative of formula XV that is, m is 1 for formula I. An organic base is used to take up the hydrogen halide formed in the reaction, suitable bases being triethylamine (TEA) and Hünig's Base. Suitable reaction media include halogenated solvents, such as methylene chloride and chloroform. The reaction is preferably run at low temperature, at least initially. Suitable temperatures are in the region of –50° C. down to –80° C. Later in the reaction it may be desirable to allow the mixture to warm up to about RT to ensure completion of the reaction.

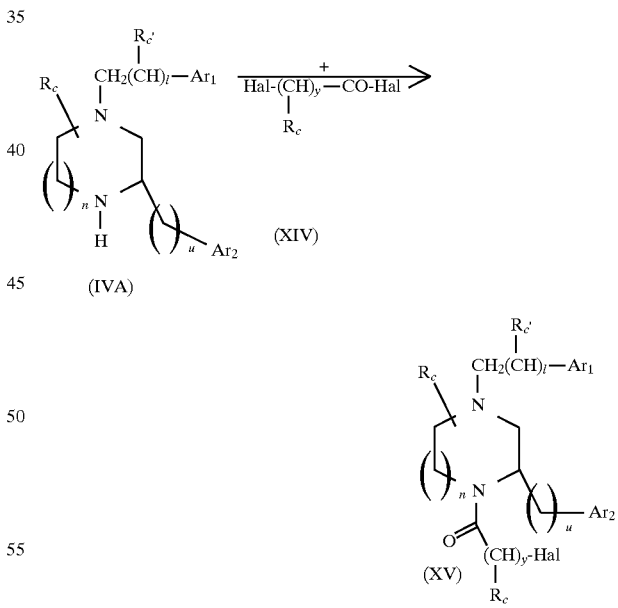

(IVA)         (XIV)

(XV)

Reaction of the halogenated amides of formula XV with an amine of formula Z-H results in formation of the products of formula XVI, which are compounds of the invention in which X is O and m is 1. Compounds of formula XVI have been modified to show the fact that these products could have been prepared from compounds of formula IVA as well as from IV. Suitable solvents for this reaction are halogenated hydrocarbons, such as methylene chloride, and an organic base is present to absorb the H—Hal formed.

Appropriate bases include Hünig's Base. The reaction is performed at or around RT, a suitable temperature being generally in the range of from 0° C. to 40° C. Reaction is complete within 1 to 48 hours.

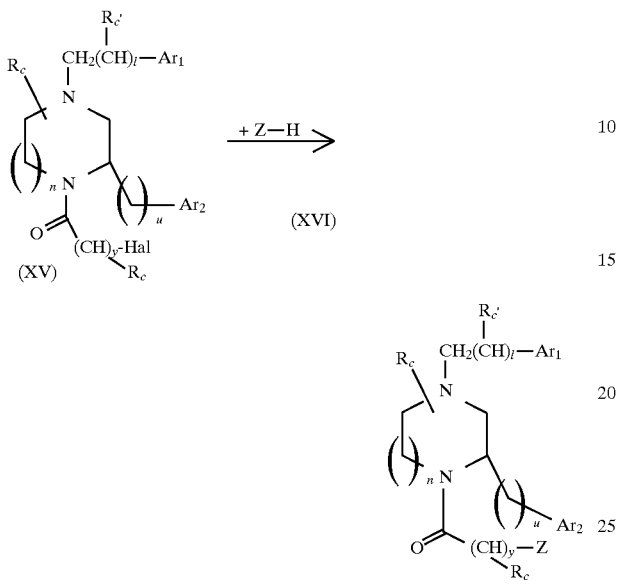

Method 5.

Compounds of formula XVI where y≠0 may be converted to other compounds of the invention of formula XVII by reduction under controlled conditions.

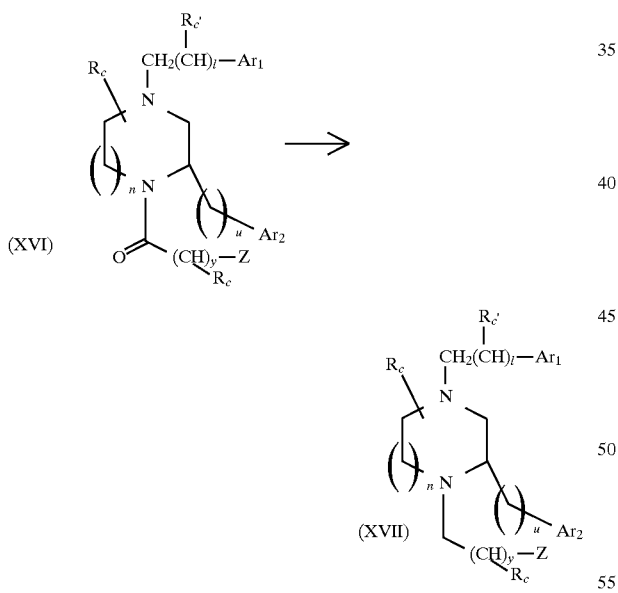

Suitable reducing agents to effect this transformation include the borane-dimethyl sulfide complex, as well as other less selective reagents, such as LAH, (assuming that no other group reactive to LAH is present), Red-Al®, and diborane in ether. Effective temperatures for the boranedimethylsulfide complex to reduce compounds of formula XVI, range from RT to the reflux temperature of the solution of the reagent in THF (about 80° C.).

Method 6. Intermediates of the formula XVIII may be selectively acylated by coupling with an acid of the formula XIX. Standard coupling techniques may be applied, an example being the use of HOBT, a water-soluble carbodiimide, such as DEC, and an organic base, such as triethylamine, in a non-hydroxylic solvent, such as $CH_2Cl_2$, at a temperature of about −20° C. initially. The mixture may be allowed to warm to RT to complete the reaction. The product of reaction is the amide of formula XX.

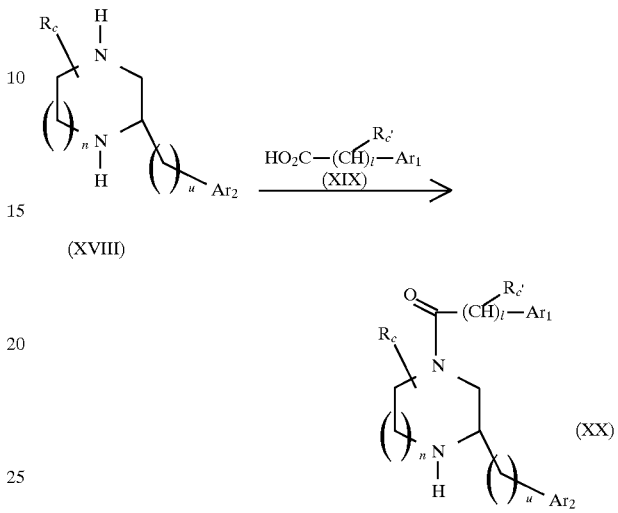

Compounds of the formula XX, may be further acylated using an acid halide of formula XIV. The reaction is run, preferably at about −78° C., over a period of 1 to 12 hours, in a halogenated solvent, such as methylene chloride or similar solvent. An organic tertiary amine is used to absorb the H-Hal produced in the reaction. Suitable amines include triethylamine and Hünig's Base. As used herein Hal means Cl, Br, or I.

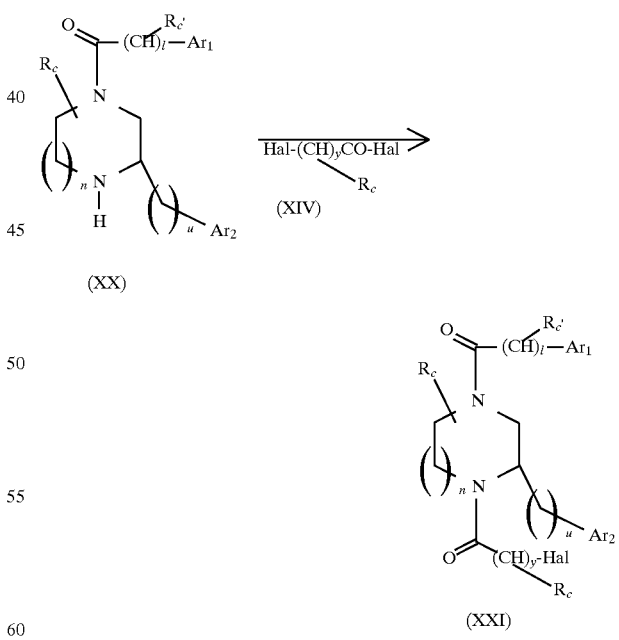

The compounds of formula XXI, that is, m is 1 in formula I, y=1–3, I=0–2 may be used for further reaction without isolation. Additional organic base, for instance, Hünig's Base, is added to the mixture followed by Z-H, at or around −78° C. The reaction is completed by allowing the mixture to warm to RT overnight yielding the compounds of formula XXII after work-up and purification by standard methods.

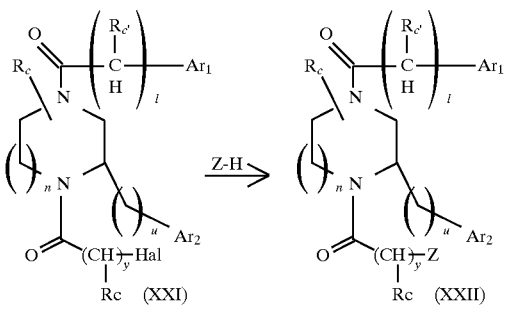

The compounds of formula XXII, in which y=1–3 may be converted to other products of formula XXIII by reduction under controlled conditions.

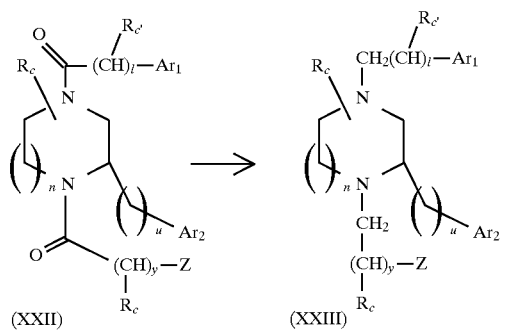

Suitable reducing agents to effect this transformation include the borane-methyl sulfide complex, as well as other less selective reagents, such as LAH, Red-Al®, and diborane in ether or other unreactive solvents, such as THF. Using the borane-methyl sulfide complex in THF, at the reflux temperature of the solution, which is about 80° C., the reaction is complete in about 2 hours to 48 hours depending on the precise substrate.

Some of the substrates Z-H for the alkylation reaction were synthesized from diamino compound (A) by initial conversion to the t-BOC protected derivative(B) followed by removal of the benzyl group by hydrogenolysis over a suitable catalyst such as $Pd(OH)_2$ to yield the t-BOC protected derivative (C). Subsequent elaboration of (C) can be accomplished by either alkylation or reductive alkylation depending on the availability of reagents for these reactions.

Reaction of the intermediate (C) with an aldehyde or ketone (D) under the conditions of reductive amination, such as in methanol and in the presence of $NaBH_3CN$ with sufficient AcOH (acetic acid) present to allow the reaction to proceed at a suitable rate, produces the amine (E) from which the t-BOC group may be removed with 4N-HCl in dioxane followed by basification, for instance, with an aqueous solution of NaOH, to produce the compound of formula (F).

The same product, (Ea), may be prepared from (C) by alkylation with the halide derivative (G) in which "Hal" is Cl, Br, or I. Other activated leaving groups are also possible for this reagent, such as mesylates or tosylates. The reagent is preferably primary but the reaction can also often be made to work acceptably for secondary derivatives.

The product of the alkylation, (Ea), may be treated as described above to produce the reagent (Fa) which represents one of the preferred forms of Z which can be used to convert a compound of formula XXI to a compound of formula XXII.

The intermediate (C) (below) may also be modified by acylation, for instance with an acid halide of formula (H), to produce the intermediate (1), in which $n_3 \neq 0$. Removal of the BOC protecting group, as described previously, leads to the amine (J) which represents one of the preferred forms of Z. This may be used to convert a compound of formula (XXI) to a compound of the invention, as described above.

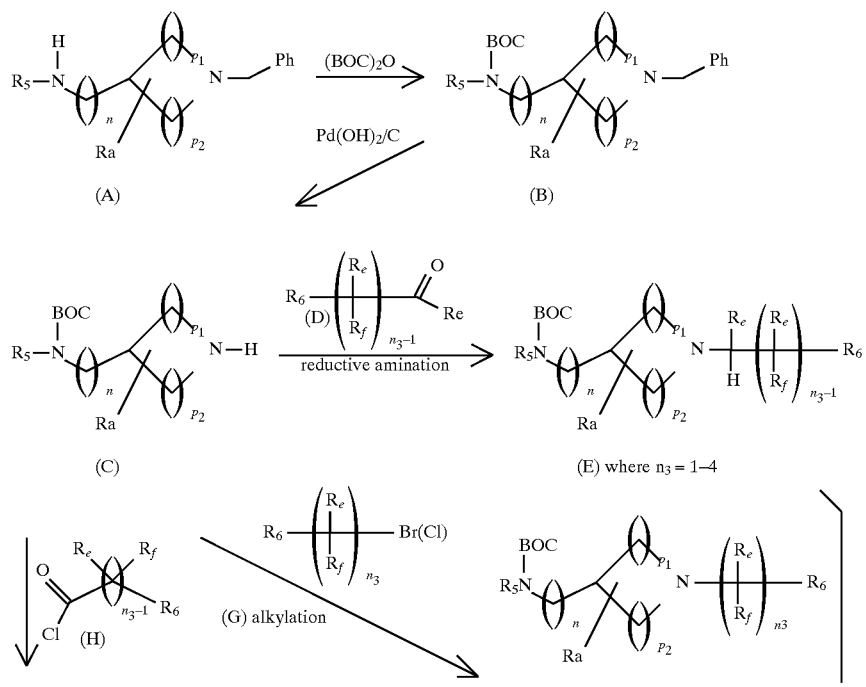

-continued

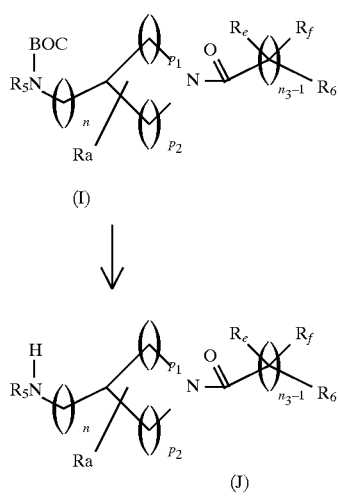

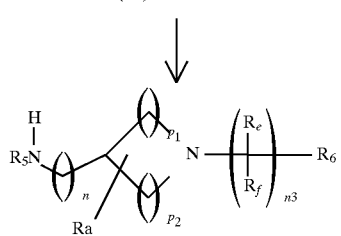

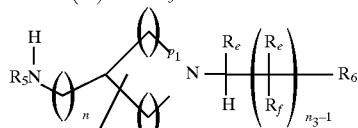

Method 6a A useful intermediate for certain variations in the group Z is the compound (K). This may be prepared from (XXI) and the protected amine (L). The starting material for this process is the N-BOC protected amine (M) which may be converted to (L) by standard techniques involving formation of the oxime using hydroxylamine hydrochloride in pyridine followed by reduction with hydrogen over Raney nickel in ethanol solution. Removal of the protecting group from (K), under conditions described previously, results in the amine (N).

halide, e.g. chloride (P), may be used, or a coupling reaction with a carboxylic acid may be used under conditions essentially similar to those described earlier using a water-soluble carbodimide reagent, for instance.

Sometimes the starting material (N) is provided as a salt, such as the HCl salt. In this case, it is necessary to add an organic tertiary base, such as Hünig's base to produce the free amine.

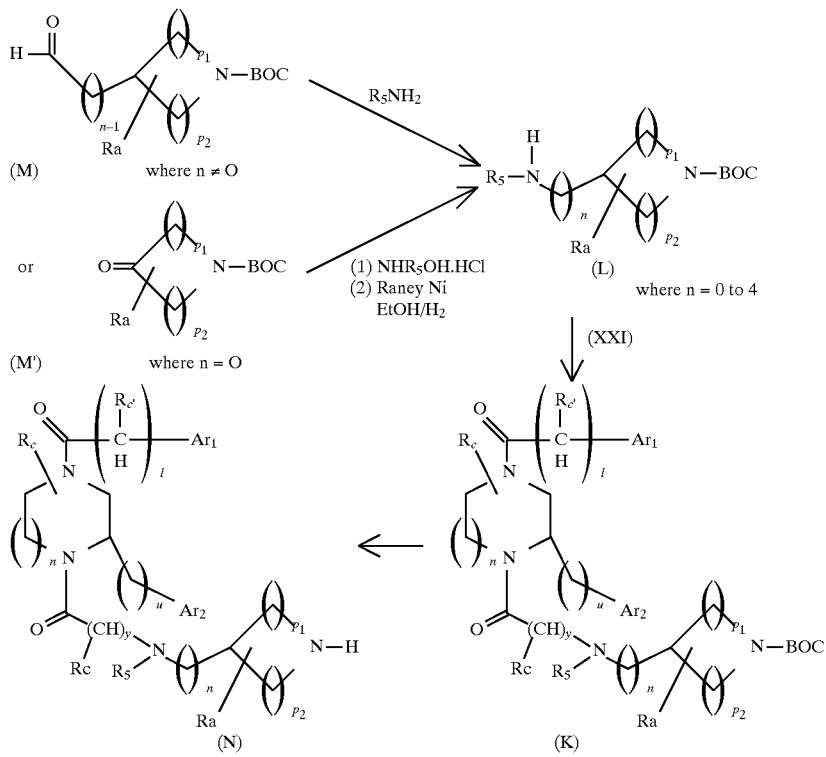

Use of this intermediate under conditions of acylation, under controlled conditions, results in reaction at the ring nitrogen atom to yield products such as (O). Either the acid

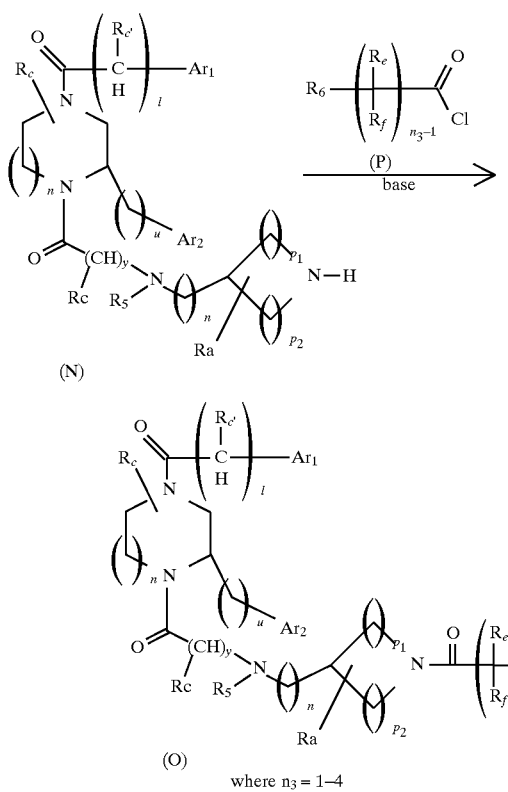

Alkylation of (N) may be accomplished with a suitable halogen-containing reagent, for instance, to produce (Q). Reagents such as (G) may be used for this conversion.

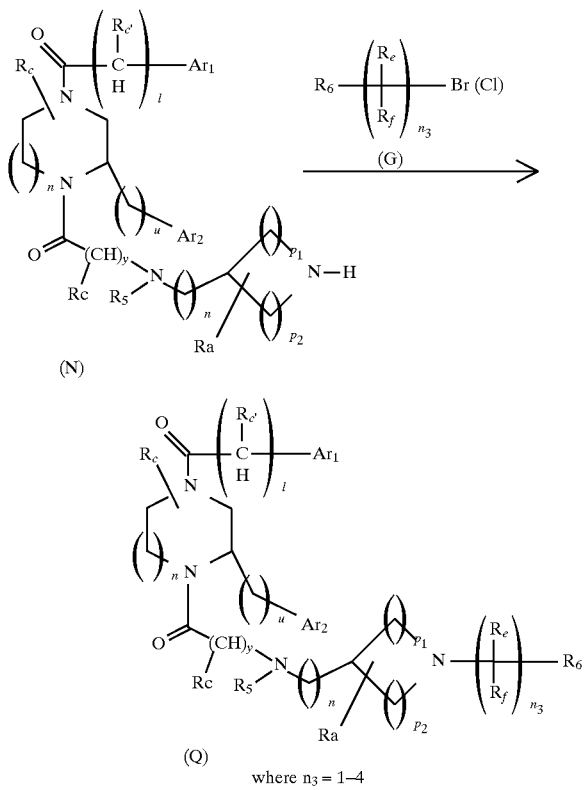

In some cases, one of the —$C(R_e)(R_f)$— groups may be a carbonyl group with the exception that the carbon in the carbonyl can not be directly attached to the nitrogen atom since these products are amides which are described above.

Under certain circumstances, specifically where at least one of the groups $R_e$ and $R_f$ on the carbon atom to be directly attached to the ring nitrogen is H, then a reductive alkylation reaction may be performed, as described previously, to produce the compound of the invention (R). The reagent used for this conversion is (D), an aldehyde (if $R_e$=H) or ketone.

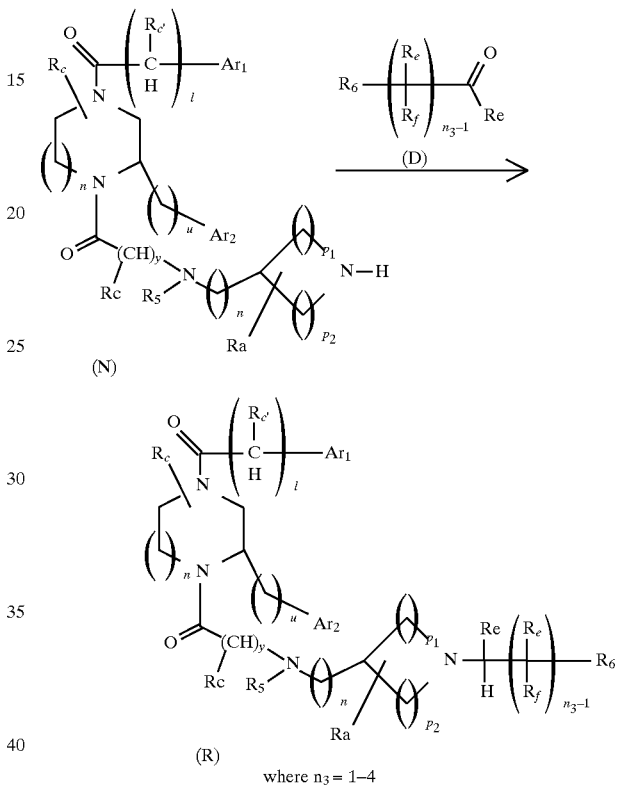

Method 7. The acylated derivatives of formula XX from Method 6 may be reduced to the saturated alkyl chain derivatives of formula IVA.

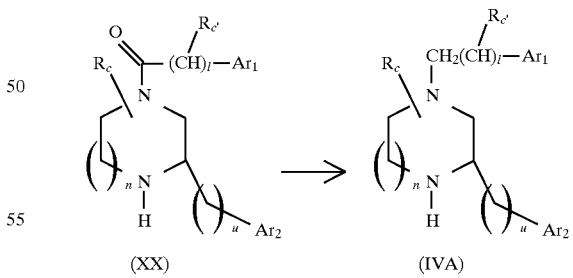

The process to conduct this conversion is the same as described in Method 6 for conversion of a compound of formula XXII to a compound of formula XXIII. The reagent of preference is the borane-methyl sulfide complex.

A compound of formula IVA can be converted to a target compound of formula XVI as described previously.

An alternate route to compounds of structure (XXII) also starts with compound (XVIII). Initial reaction with an amine protecting group reagent, preferably BOC anhydride, produces the N-t-butyloxycarbonyl derivative of the formula XXVIII.

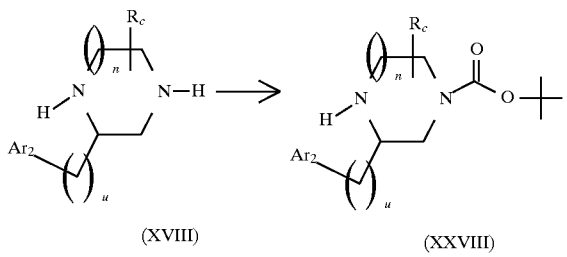

(XVIII)   (XXVIII)

As before, reaction occurs preferentially at the nitrogen atom further away from the $Ar_2$ group. Reaction of this intermediate with a reagent of structure (XIV) as described above, leads to the halo-derivative (XXIX). Reaction of (XXIX) with Z-H, again as described above, produces the intermediate (XXX) which may be de-protected to produce (XXXI). Suitable reagents include trifluoroacetic acid and HCl.

(XXVIII) + (XIV) $\longrightarrow$

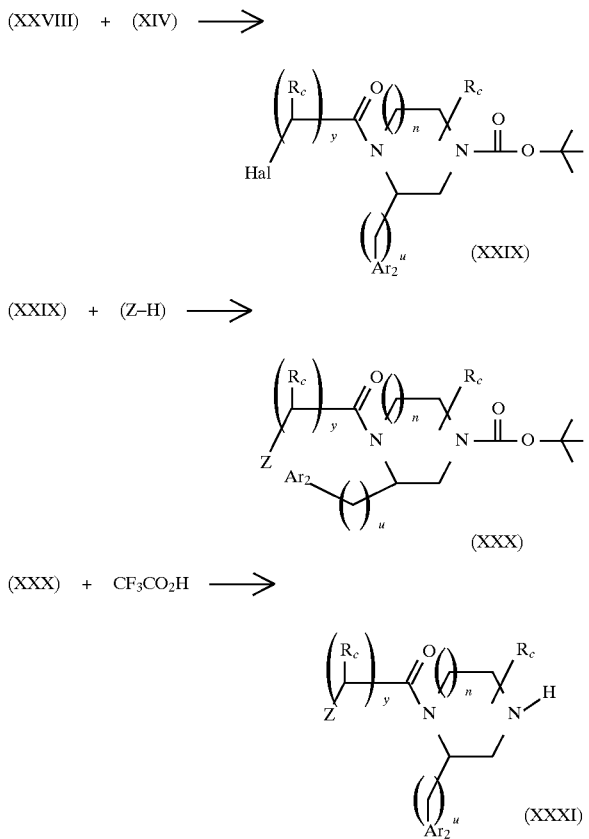

Reaction of (XXXI) with a carboxylic acid (XIX) under such coupling conditions as described above, leads to the products of formula (XXII).

Method 7a.

Synthesis of the compounds of the invention wherein the pendant aromatic group $Ar_2$, or the pendant aromatic group $Ar_2$ and its sidechain, are located in the alternate ring position to the compounds of formula XXII (i.e. compounds of formula C below), may be prepared using compounds of formula XXVIII from method 7 as starting materials. Coupling of compounds of formula XXVIII with any of the acids

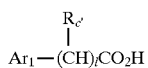

under standard coupling conditions, for instance using HOBT, $Et_3N$ and DEC in $CH_2Cl_2$, produces the intermediate (A). Removal of the t-BOC or other protecting group under standard conditions releases the free amine (B). Acylation of (B) and further reaction with Z-H proceeds as described in Method 6 for the conversion of (XX) via (XXI) to (XXII) to produce compound (C) of the invention.

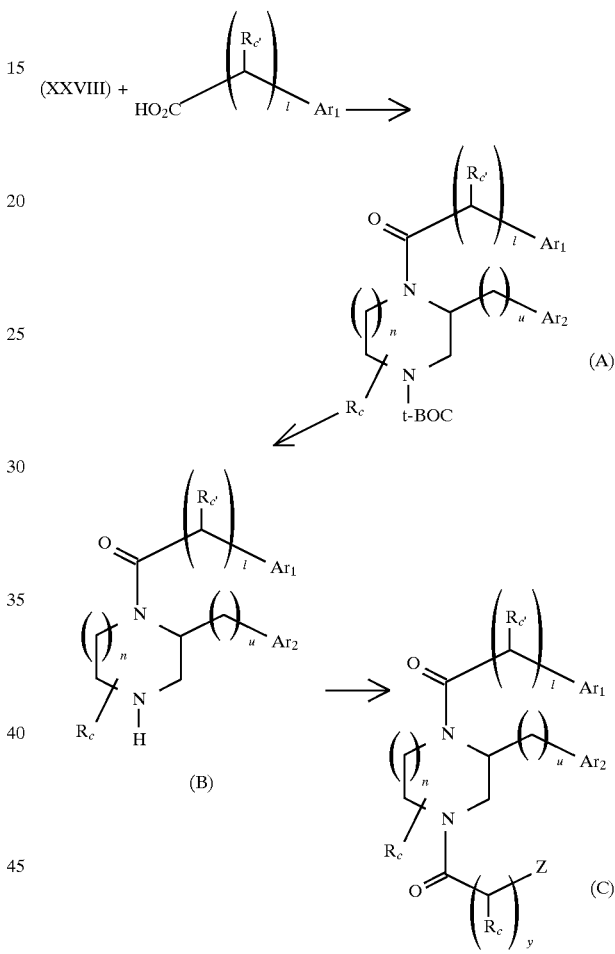

Method 8.

A method for introducing a group, $R_c$, into the sidechain of a compound of the invention begins with a previously prepared compound of formula (XX). This may be coupled with a suitably protected amino-acid derivative of formula (XXXII) in which the t-BOC group is used as a representative protecting group. Use of a relatively reactive coupling agent, such as BOP—Cl of formula (XXXIII), is preferred and the reaction is run under standard coupling conditions well known to one skilled in the art. Suitable conditions include the use of $CH_2Cl_2$ and/or DMF as solvent, with triethylamine or Hünig's Base, and a temperature between 0° C. initially and RT. Usual work-up conditions yield the protected intermediate of formula (XXXIV).

In the case of (XXXIV), in which the N-protecting group is t-BOC, the usual conditions for removal of such a group may be used to free the amine function. Various concentrations of $CF_3CO_2H$ in $CH_2Cl_2$ will usually suffice. In some substrates a fairly dilute solution (e.g. 2N) will be sufficient whereas in other cases a more concentrated solution, up to neat TFA, may be necessary. In addition, other N-protecting groups may be employed and removed by methods well known in the art. An example is use of the N-Cbz which may be removed under either acidic or hydrogenolytic conditions. The result of deprotection is the amine intermediate of the formula (XXXV).

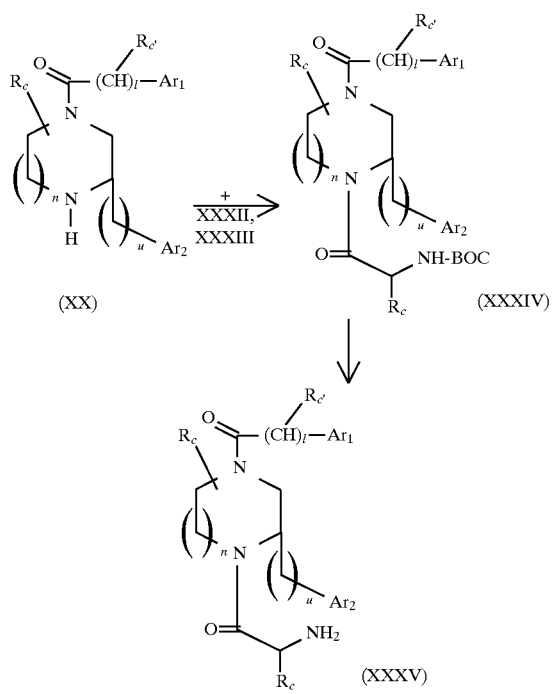

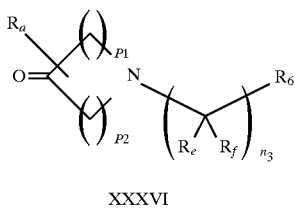

Conversion of intermediate of the formula (XXXV) to compounds of the invention is then carried out by a reductive alkylation process.

The group Z is introduced into the molecule using an aldehyde or ketone in which the aforementioned group is present at the carbon atom that is to be joined to the amino group of the formula (XXXV). An example of such an intermediate is a compound of the formula (XXXVI).

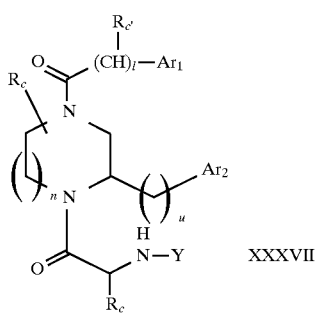

After the reaction this group becomes the Z group of the compounds of the invention, that is, the "Y-NH" group shown in compounds of the formula (XXXVII) just below is equivalent to the "Z" group shown in the Summary of the Invention. Conditions for this reductive amination procedure are known in the art and are exemplified by the use of $NaBH_3CN$ in MeOH with the addition of several equivalents of acetic acid. Generally, the reaction is performed at RT and is left to react overnight.

Product is isolated by standard means, such as decomposition of excess reagent with $H_2O$ and extraction of the product into an organic solvent such as $CH_2Cl_2$ or a mixture of $Et_2O$ and $CH_2Cl_2$.

Using procedures similar to those described in the above or using procedures known to those skilled in the art, one can produce all of the compounds of formula I of the invention. For example, one can obtain compounds of the invention of formula I wherein the $R_c$ moiety is on various carbons of the piperazine ring.

The in vitro and in vivo activity of the compounds of formula I can be determined by the following procedures.

In vitro procedure to identify $NK_1$ activity

Test compounds are evaluated for their ability to inhibit the activity of the $NK_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% $O_2$ and 5% $CO_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1\times10^{-10}M-7\times10^{-7}M$). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.

Isolated Hamster Trachea $NK_2$ Assay

General methodology and characterization of hamster trachea responses to neurokinin agonists as providing an $NK_2$ monoreceptor assay is found in C. A. Maggi, et al., Eur. J. Pharmacol. 166 (1989) 435 and J. L. Ellis, et al., J Pharm. Exp. Ther. 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% $O_2$–5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$–5% $CO_2$ gas. Tracheal rings are placed under 1.0 g initial tension and allowed a 90 min equilibration period with four 1 $\mu$M NKA challenge, wash and recovery cycles at 20 min intervals. 30 min vehicle pretreatment is followed by cumulative additions of rising doses of NKA (3 nM–1 $\mu$M final concentration, 5 min intervals between additions). The final NKA response is followed by a 15 min wash and recovery period. 30 min pretreatment with a test compound or its vehicle is followed by cumulative additions of rising doses of NKA (3 nM–10 $\mu$M final concentration if necessary, 5 minutes intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio >2 at a screening concentration of 1 $\mu$M (i.e. $pA_{2\geq}=6.0$) are considered actives. Further dose response data is obtained for actives so that an apparent $pA_2$ estimate can be calculated. $pA_2$ is calculated either by estimation of $K_i$ as described by Furchgott (where $pA_2=-$Log $K_i$, R. F. Furchgott, Pharm. Rev. 7 [1995] 183) or by Shild Plot Analysis (O. Arunlakshana & H. O. Shild, Br. J. PharmacoL 14[1959] 48) if the data is sufficient.

Effect of $NK_1$ Antagonistspon Substance P-Induced Airway Microvascular Leakage In Guinea Pigs Studies are performed on male Hartley guinea pigs ranging in weight from 400–650 g. The animals are given food and water adlibitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated (VT=4 ml, f=45 breaths/min) with a Harvard rodent respirator. The jugular vein is cannulated for the injection of drugs.

The Evans blue dye technique (Danko, G. et al., Pharmacol. Commun., 1, 203–209, 1992) is used to measure airway microvascular leakage (AML). Evans blue (30 mg/kg) is injected intravenously, followed 1 min later by i.v. injection of substance P (10 $\mu$g/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 $\mu$g/ml in formamide. The dye concentration is expressed as ng dye per mg tissue wet weight. Test compounds were suspended in cyclodextran vehicle and given i.v. 5 min before substance P.

Measurement of $NK_a$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range ±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 $\mu$g/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100units/ml of penicillin and streptomycin, and 0.8 mg of G418/ml at 37° C. in a humidified atmosphere containing 5% $CO_2$.

Cells are detached from T-175 flasks with a sterile solution containing 5mM EDTA in phosphate buffered saline. Cells are harvested by centrifugation and washed in RPMI media at 40° C. for 5 minutes. The pellet is resuspended inTris-HCl (pH7.4) containing 1 uM phosphoramidon and 4 ug/ml of chymostatin at a cell density of $30\times10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at −80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 ($NK_1$) or 1 μM SR-48968 ($NK_2$) (both synthesized by the chemistry department of Schering-Plough Research Institute). $IC_{50}$ values are determined from competition binding curves and $K_i$ values are determined according to Cheng and Prusoff using the experimentally determined value of 0.8 nM for the $NK_1$ receptor and 2.4 nM for the $NK_2$ receptor.

For all of the compounds of the invention, the $NK_1$ binding is in a range of about 0–100% inhibition at 1 μM concentration. For all of the compounds of the invention, the $NK_2$ binding is in a range of about 0–100% inhibition at 1 μM concentration. It should be understood that while the NK binding for certain compounds of the invention is as low as 0% at 1 μM concentration, that at higher concentrations these compounds are expected to have NK binding inhibition activity.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ were determined. The $K_i$'s for $NK_1$ for such compounds fell within a range of about 0.1 nM to about 1 μM.

For those compounds of the invention having higher than 50% inhibition of $NK_2$, $K_i$'s for $NK_2$ were determined. The $K_i$'s for $NK_2$ for such compounds fell within a range of about 0.1 nM to about 1 μM.

Compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. Certain compounds have both strong NK1 and NK2 antagonist activities. Some compounds can also be $NK_3$ antagonists.

Many compounds of formula I have an asymmetric center and therefore exist as a pair of enantiomers. In such cases, one enantiomer can have different biological activity than the other. For example, one enantiomer can have strong $NK_1$ activity and weak $NK_2$ activity while the other enantiomer has weak $NK_1$ activity and strong $NK_2$ activity.

Certain compounds of formula I have been found to be antagonists of both $NK_1$ and $NK_2$ receptors, and are therefore useful in treating conditions caused or aggravated by the activity of $NK_1$ and $NK_2$ receptors.

$NK_1$ binding and $NK_2$ binding values for certain compounds of the invention are as follows:

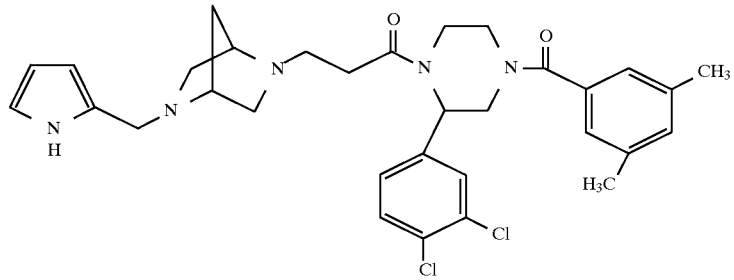

(enantiomer B)
has a $K_i$ for $NK_1$ binding, of 34 nM; and has a $K_i$ for $NK_2$ binding of 12nM.

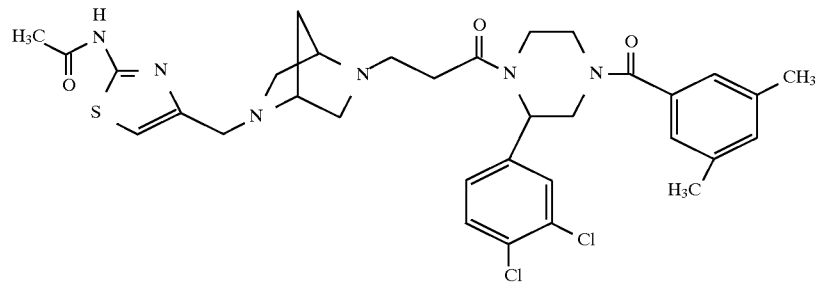

has a $K_i$ for $NK_1$ binding, of 13 nM; and a $K_i$ for $NK_2$ binding, of 13 nM.

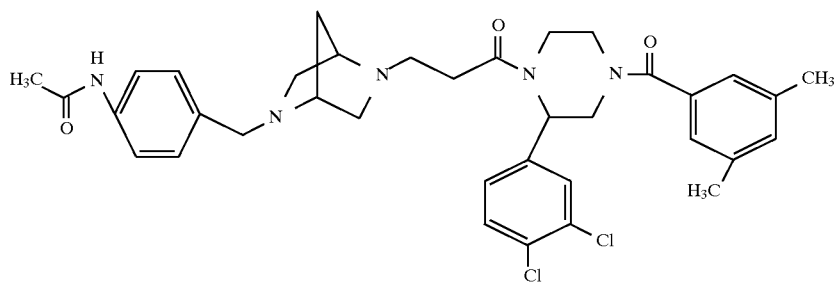
has a $K_i$ for $NK_1$ binding, of 4.8 nM; and a $K_i$ for $NK_2$ binding, of 13 nM.
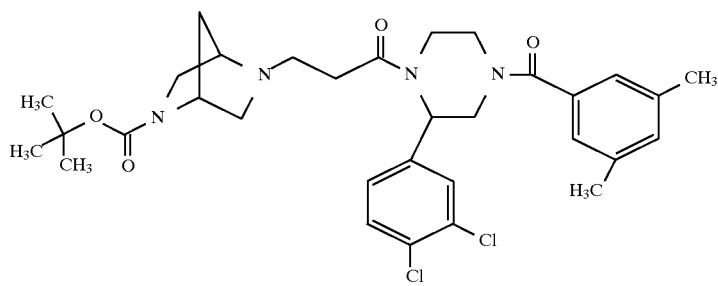
has a $K_i$ for $NK_1$ binding, of 67 nM; and a $K_i$ for $NK_2$ binding, of 18 nM.
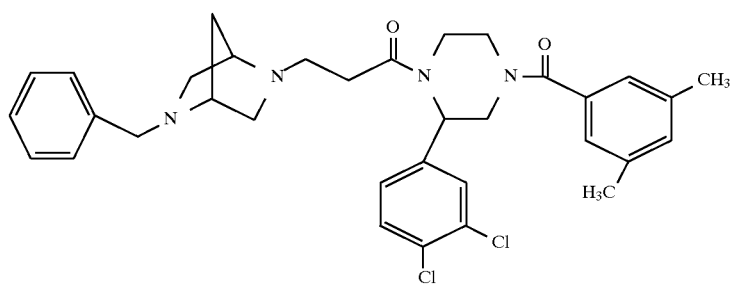
has a $K_i$ for $NK_1$ binding, of 12.4 nM; and a K; for $NK_2$ binding, of 3 nM.
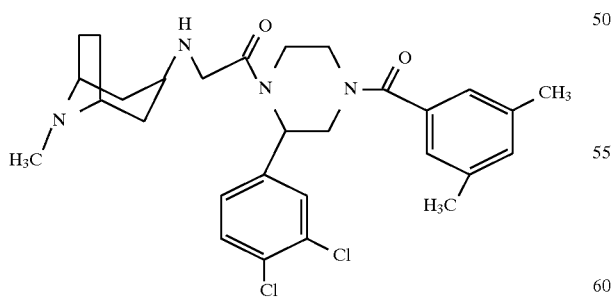
has a $K_i$ for $NK_1$ binding, of 58 nM; and a $K_i$ for $NK_2$ binding, of 9.3 nM.

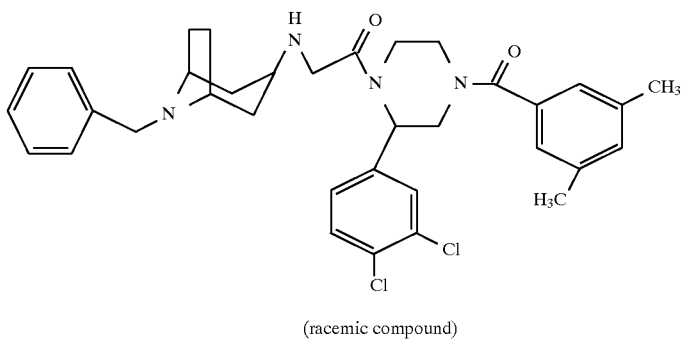

(racemic compound)

(racemic compound)
has a $K_i$ for $NK_1$ binding, of 0.6 nM; and a $K_i$ for $NK_2$ binding, of 7.5nM.

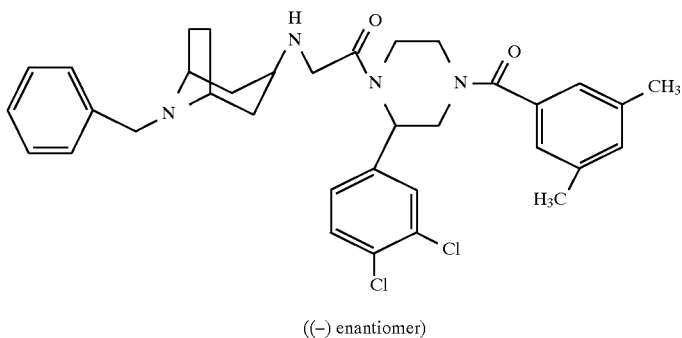

((−) enantiomer)

has a $K_i$ for $NK_1$ binding, of 14.5 nM; and a $K_i$ for $NK_2$ binding, of 2 nM.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ were determined. The $K_i$'s for $NK_1$ for such compounds fell within a range of about 11nM to about 176 nM.

For those compounds of the invention having higher than 50% inhibition of $NK_2$, $K_i$'s for $NK_2$ were determined. The $K_i$'s for $NK_2$ for such compounds fell within a range of about 175nM to about 300 nM.

It will be recognized that compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. While compounds with approximate equipotency are preferred, it is also within the scope of this invention to use compounds of with unequal $NK_1/NK_2$ antagonist activity when clinically appropriate.

Certain compounds of formula I have been found to be antagonists of both $NK_1$ and $NK_2$ receptors, and are therefore useful in treating conditions caused or aggravated by the activity of $NK_1$ and $NK_2$ receptors.

Compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. Certain compounds have both strong NK1 and NK2 antagonist activities. Some compounds can also be $NK_3$ antagonists.

Many compounds of formula I have an asymmetric center and therefore exist as a pair of enantiomers. In such cases, one enantiomer can have different biological activity than the other. For example, one enantiomer can have strong $NK_1$ activity and weak $NK_2$ activity while the other enantiomer has weak $NK_1$ activity and strong $NK_2$ activity.

Certain compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

The invention disclosed herein is exemplified by the following examples, which should not be construed to limit the scope of the disclosure. Alternative mechanistic pathways and analogous structures within the scope of the invention will be apparent to those skilled in the art.

EXAMPLE 1

Preparation of 2-(3,4-dichlorophenyl)piperazine

A. Synthesis of racemic compound 2-(3,4-Dichlorophenyl)piperazine was synthesized according to the method published in J.Med.Chem. 9, 181, 1966.

A. General method for the synthesis of 2-aryl-piperazine derivatives.

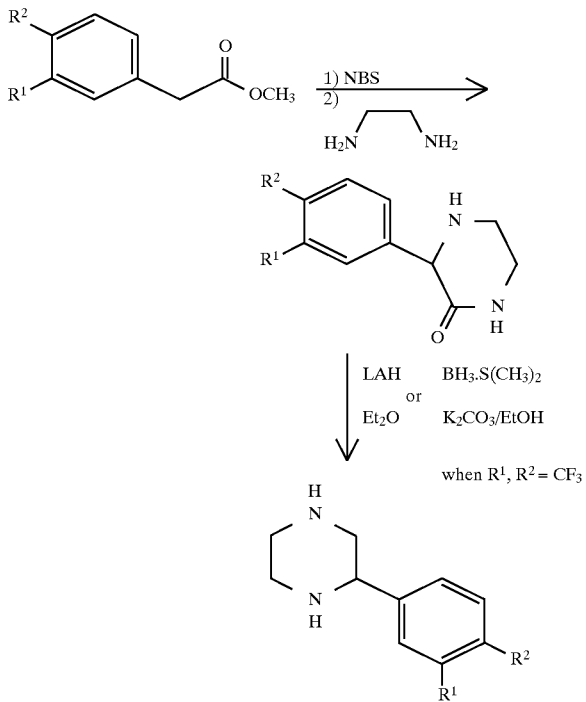

$R^1$=Cl, H or other substituents i.e. $OCH_3$, $CF_3$, Br, I, F, etc.
$R^2$=Cl, H or other substituents i.e. $OCH_3$, $CF_3$, Br, I, F, etc.

B. Resolution of 2-(3,4-dichlorophenyl)piperazine

Step 1

A solution of 2-(3,4-dichlorophenyl)piperazine (36.05 g, 0.156 mol) in methanol (200 mL) was treated with a solution containing two equivalents of N-acetyl-L-leucine (54.02 g, 0.312 mol) and heated until all of the material was dissolved. EtOAc (2.2 L) was added to this solution and allowed to stand at ambient temperature overnight. The solvent phase was decanted from the precipitated salt and concentrated in vacuo. This procedure was repeated using 37.88 g of 2-(3,4-dichlorophenyl)piperazine (0.164 mol) and 56.68 g of N-acetyl-L-leucine (0.327 mol).

Step 2

The concentrated salts from both solvent phases in step 1 were combined and heated in methanol (550 mL) until all of the material dissolved. EtOAc (2.75 L) was added to this solution and allowed to stand at ambient temperature overnight. The solvent phase was decanted from the precipitated salt and concentrated in vacuo to give ~95 g of piperazine salt (72% ee of enantiomer A).

Step 3

The salt from the solvent phase in step 2 was dissolved in a solution of $H_2O$ (800 mL) and aq. ammonia (400 mL) and extracted with $CH_2Cl_2$ (4×400 mL). The combined organic layers were dried with $MgSO_4$ and concentrated to give 37 g of the piperazine free base. The free base was recrystallized three times from hexane (890, 600 and 450 mL) to give 16 g of piperazine (>99.9% ee of enantiomer A).

24.7° C.

$[\alpha]_D$=−45.0°(MeOH)

Step 4

The precipitated salts from step 1 were combined and heated in methanol (220 mL) until all of the material dissolved. EtOAc (2.2 L) was added to this solution and allowed to stand at ambient temperature overnight. The solvent phase was decanted from the precipitated salt and dried in vacuo to give ~43 g of piperazine salt (93% ee of enantiomer B).

Step 5

A 12.3 g portion of salt (75% ee of enantiomer B) prepared by an analogous procedure to that in step 4 was dissolved in 0.5M NaOH (400 mL) and extracted with $CH_2Cl_2$ (4×155 mL). The combined organic layers were dried with $MgSO_4$ and concentrated to give 3.72 g of the piperazine free base. The free base was recrystallized twice from hexane (90 and 70 mL) to give 2.1 g of piperazine (98% ee of enantiomer B).

C. Analytical procedure for measuring piperazine enantiomeric purity.

The enantiomeric purity of the piperazine was measured by chiral HPLC analysis of the di-tert-butoxycarbonyl piperazine derivative. The di-tert-butoxycarbonyl derivative was prepared by adding a small piperazine sample (free base or salt)(~0.2 mg) to di-tert-butyl dicarbonate (~1 mg) and methanol (0.5 mL) and heating at 80° C. for 1 h. If the piperazine sample is a salt, triethylamine (20 μL) is also added. The derivative was analyzed by HPLC using a ChiralPak AD column eluting with 95:5 hexane-isopropyl alcohol.

EXAMPLE 2

Preparation of (+,−)-[3,5-dimethylbenzoyl]-3-(3,4-dichlorophenyl)piperazine

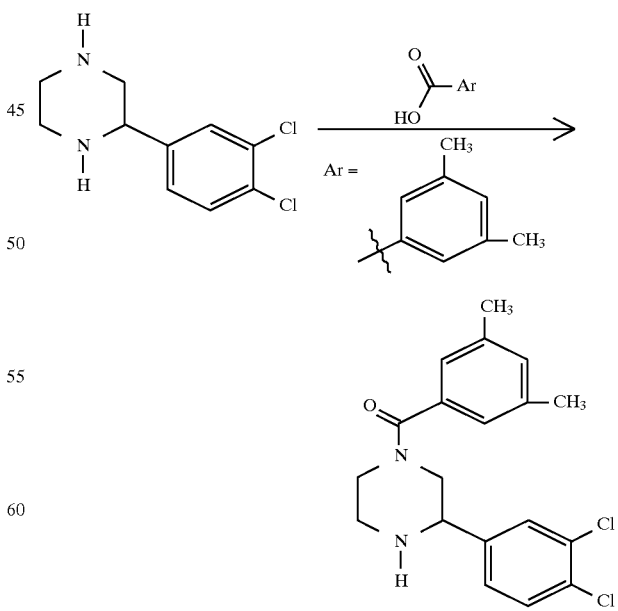

To a cooled solution of $CH_2Cl_2$ (600 mL) containing 2-(3,4-dichlorophenyl)piperazine (6.934 g, 30 mmol), 3,5- dimethylbenzoic acid (4.55 g, 30 mmol), and N-hydroxybenzotriazole monohydrate (4.05 g, 30 mmol) at −20° C. were added Et₃N (4.2 mL, 30 mmol) and N,N-dimethylaminopropylethylcarbodimide (DEC) (5.86 g, 30 mmol) under nitrogen. The reaction was kept at −20° C. for an hour and gradually warmed to RT overnight. After stirring 22 hours, the reaction was complete and CH₂Cl₂ (200 mL) was added. The organic solution was washed with brine (150 mL, 3×), dried over MgSO₄, filtered and concentrated under vacuum to give 8.2 g of crude product. The product was crystallized from CH₂Cl₂/Hexane to give a light yellow solid (6.3 g, 17.34 mmol, 57.8%), m.p.139°–141° C.; FAB MS [M+1]⁺ ³⁵Cl 363.1.

EXAMPLE 3

Preparation of (+,−)-bromoacetyl-2-(3,4-dichlorophenyl)-4-(3,5-dimethylbenzoyl)piperazine

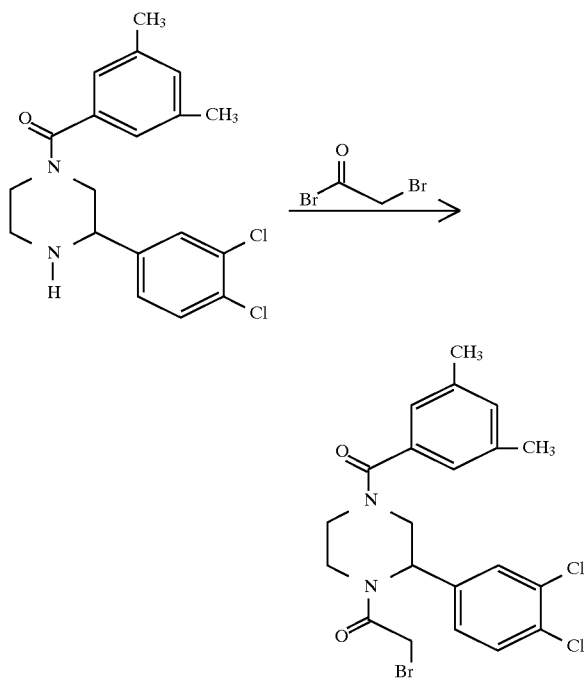

To a cooled solution of (+,−)-[3,5-dimethylbenzoyl]-3-(3,4-dichlorophenyl)piperazine (11.5 g, 31.65 mmol) in CH₂Cl₂ (200 mL) at 0° C. was added Hünig's base (4.5 g, 35 mmol) and bromoacetyl bromide (6.4 g, 31.65 mmol). The solution was stirred at 0° C. overnight under N₂. After completion the reaction was diluted with CH₂Cl₂ (400 mL) and washed with brine (300 mL, 2×), dried over MgSO₄, filtered and concentrated. The crude material was purified by flash grade silica gel chromatography, eluting with 2% [NH₄OH/MeOH (1:9)]/98% CH₂Cl₂ to give the title compound as a light yellow solid (7.1 g, 47.3%), m.p. 77°–79° C., FAB MS [M+1]⁺ ³⁵Cl, ⁷⁹Br 482.9, 484.9.

EXAMPLE 4

Preparation of (+)-[3,5-dimethylbenzoyl]-3-(3,4-dichlorophenyl)piperazine (Enantiomer B)

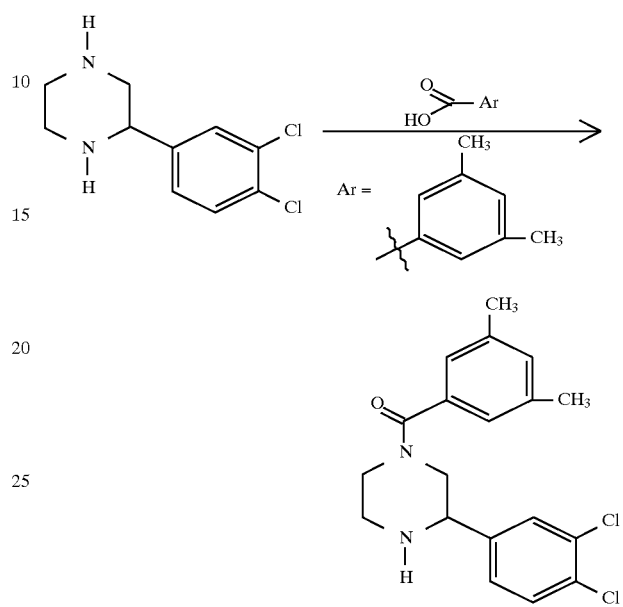

The title compound was prepared by an analogous method to that desecribed in Example 2 using (−)2-(3,4-dichlorophenyl)piperazine in place of (+,−)-2-(phenyl) piperazine, m.p. 97°–100° C.; FAB MS [M+1]⁺ ³⁵Cl 363:1;

$[\alpha]_D^{22.5°\ C.} = +87.2°(MeOH)$.

EXAMPLE 5

Preparation of (−)-bromoacetyl-2-(3,4-dichlorophenyl)-4-(3,5-dimethylbenzoyl)piperazine (Enanitomer B)

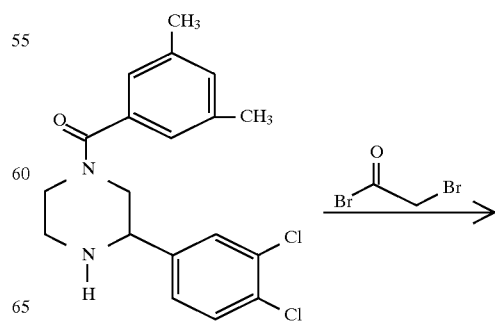

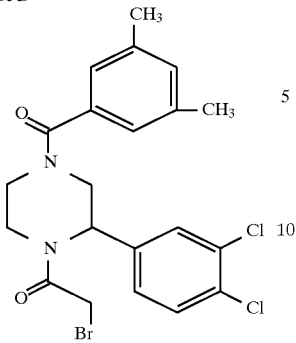

The title compound was prepared by an analogous method to that described in Example 3 using (+)-[3,5-dimethylbenzoyl]3,4-dichlorophenyl)piperazine (Enantiomer B)(Example 4) in place of (+,−)-[3,5-dimethylbenzoyl]-3-(3,4-dichlorophenyl)piperazine, m.p. 68°71° C., FAB MS [M+1]+ $^{35}$Cl $^{79}$Br 482.9, 484.8;

$[α]_D^{21.9° C.}$=−45.6°(MeOH).

EXAMPLE 6

Preparation of (+,−)-2-(3,4-dichlorophenyl)-4-(3,5-dimethylbenzoyl)-1-[[[1-[1-oxo-2-phenyl)ethyl]-4-piperidinyl]amino]acetyl]piperazine Step 1. To a solution of 4-amino-1-benzylpiperidine (9.5 g, 50mmol) in methanol (150 mL) at -10C was added a solution of di-t-butyidicarbonate (10.9 g, 50 mmol) in methanol (60 mL). The mixture was gradually warmed to room temperature overnight. After the reaction was complete, solvent was removed to give a white solid 2, FAB MS [M+1]+ $^{35}$Cl 291.3

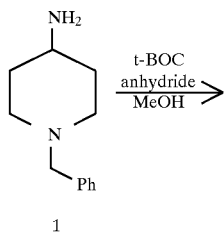

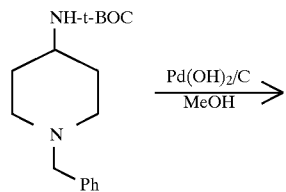

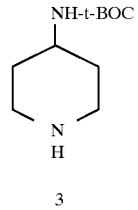

Step 2. To a soultion of compound 2 (11.6 g, 40 mmol) in methanol (140 mL) was added Pd(OH)$_2$(20% on carbon) (2.4 g) and hydrogenolyzed at 47 psi. After the reaction was complete, the catalyst was filtered off. The filtrate was evaporated to give compound 3 (8 g, 40 mmol) as a white solid.

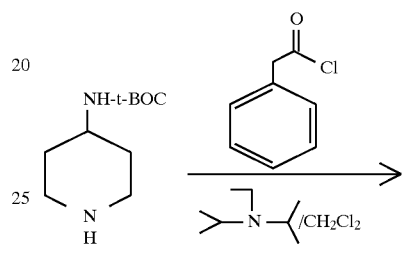

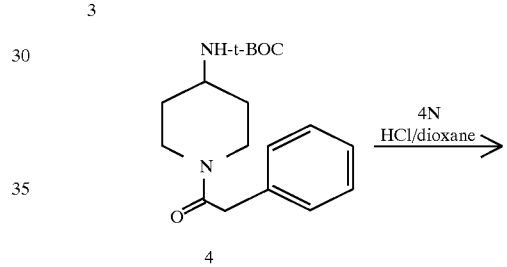

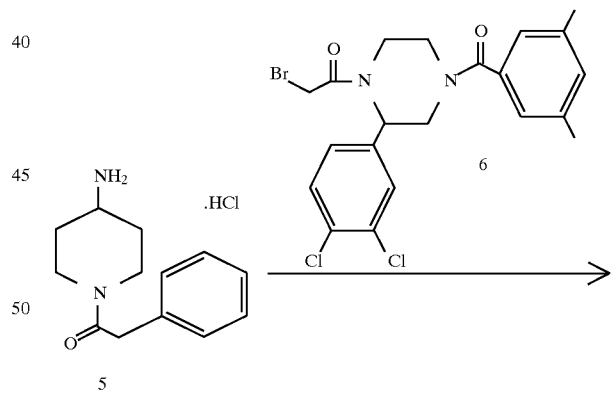

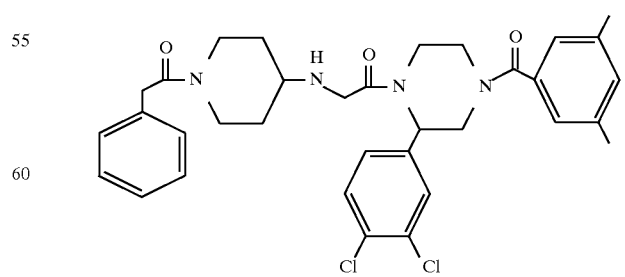

Step 3. Compound 3 (0.69 g, 3 mmol) was mixed with phenylacetyl chloride (0.46 g,3 mmol) and Hünig's base (0.43 g, 3.3 mol) in $CH_2Cl_2$ (10 mL) at $-5°$ C. and the solution was gradually warmed to RT overnight. After completion the reaction was diluted with $CH_2Cl_2$ (50 mL) and washed with brine (30 mL, 3×). The $CH_2Cl_2$ layer was dried over $MgSO_4$, filtered, and concentrated to give compound 4) as a white solid (0.81 g).

Step 4. This crude material was dissolved in dry $CH_2Cl_2$ (3 mL) and treated with 4N HCl-dioxane (6 mL). After stirring at RT for 2 h, solvents were evaporated to give 4-amino-1-(1-oxo-2-phenylethyl)piperidine 5 (0.8 g) as a white solid HCl salt. FAB MS $[M+1]^+$ 219.

Step 5. To a solution of compound 5 (0.31 g, 1.2 mmol) in $CH_2Cl_2$ (10 mL) was added Hünig's base (0.62 g, 4.8 mmol) followed by the addition of compound 6 (0.3 g, 0.6 mmol) (prepared in Example 3). The mixture was stirred at RT for 5 days under $N_2$. After completion the reaction was diluted with $CH_2Cl_2$ (50 mL) and washed with brine (30 mL×2), dried over $MgSO_4$, filtered and concentrated to give a brown gummy crude material (0.56 g). This crude material was purified by silica gel chromatography on flash grade silica (60 g), eluting with 5% [$NH_4OH$/MeOH (1:9)]/95% $CH_2Cl_2$ to give the title compound as a white solid (0.28 g, 0.45 mmol) in 75% of yield.

FAB MS $[M+1]^+$ $^{35}Cl$ 621.1; m.p.87°–89° C.

EXAMPLE 7

Preparation of (+,−)-1,1-dimethylethyl-4-[[2-[2-(3, 4-dichlorophenyl)-1-(3,5-dimethylbenzoyl)-1-piperazinyl]-2-oxoethyl]amino]-1-piperidinecarboxylate

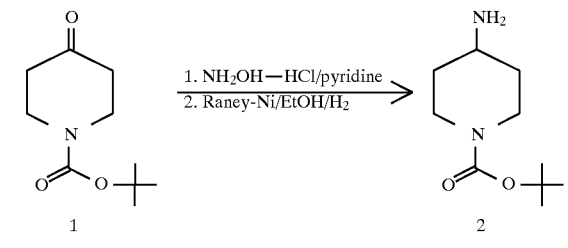

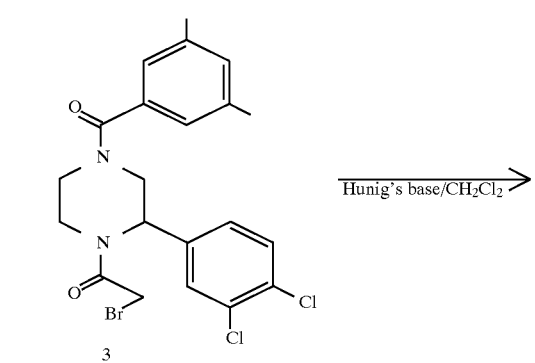

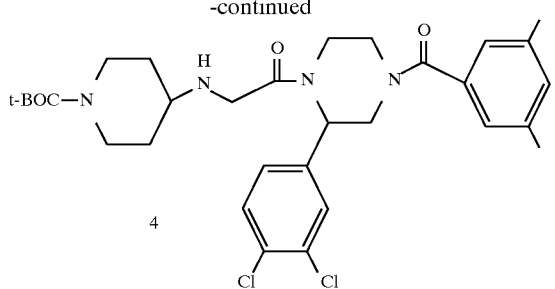

To a solution of N-t-butoxycarbonyl-4-piperidone 1 (15 g, 75.3 mmol) in pyridine (50 mL) was added hydroxylamine·HCl (5.23 g, 75.3 mmol). The mixture was heated in an oil bath at 65° C. for one hour. After cooling, pyridine was removed under reduced pressure and the residue was dried under high vacuum overnight to give a solid. To this solid was added water (100 mL) and the mixture was sonicated. The precipitate was filtered and washed with water then dried under high vacuum to give the oxime derivative of compound I (10.5 g, 65%). FAB MS $[M+1]^+$ 215.3. The oxime compound (10 g, 46.67 mmol) was dissolved in absolute EtOH (100 mL) followed by the addition of Raney Ni (29 g, washed with absolute EtOH). The mixture was hydrogenated in a Parr shaker at 50 psi overnight. After reaction was complete, the Raney Ni was filtered off (caution risk of fire) and the filtrate was concentrated to give compound 2 (9.2 g, 46 mmol,98% yield) as an oil which solidified under high vacuum drying. FAB MS $[M+1]^+$ 201.3.

To a solution of bromoacetyl derivative 3 (3.0 g,6.2 mmol) (prepared in Example 3) in $CH_2Cl_2$ (62 mL) at $-10°$ C. were added Hünig's base (1.2 mL, 6.82 mmol) and compound 2 (2.48 g, 12.39 mmol). The solution was gradually warmed to RT overnight. After reaction was complete, $CH_2Cl_2$ (300 mL) was added and washed with brine (100 mL, 3×), dried over $MgSO_4$ and filtered. The filtrate was evaporated to dryness to give a light yellow solid which was purified by flash chromatography on flash grade silica gel (200 g), eluting with 5% [$NH_4OH$/MeOH (1:9)]/$CH_2Cl_2$ to give 71% yield of the title compound 4 as a white solid (2.66 g, 4.4 mmol), m.p. 78°–81° C.; FAB MS $[M+1]^+$ $^{35}Cl$ 603.1; Calcd. for $C_{31}H_{40}N_4O_4Cl_2$, C, 61.69; H, 6.68; N,9.28; Cl, 11.74. Found: C, 61.33; H, 6.94; N, 9.17; Cl, 11.27.

EXAMPLE 8

Preparation of (−)-1,1-dimethylethyl 4-[[2-[2-(3,4-dichlorophenyl)-1-(3,5-dimethylbenzoyl)-1-piperazinyl]-2-oxoethyl]amino]-1-piperidinecarboxylate (Enantiomer B)

By employing methods analogous to those described in Example 7 using chiral bromoacetyl compound (prepared in Example 5), the title compound was obtained as a white solid, m.p.72°–75° C.; FAB MS $[M+1]^+$ $^{35}Cl$ 603.2;

$[\alpha]_D^{22° C.}=-32.8°$(MeOH).

EXAMPLE 9

Preparation of (+,-)-2-(3,4-dichlorophenyl)-4-[3,5-dimethylbenzoyl]-1-[(4-piperidinylamino)acetyl] piperazine, dihydrochloride

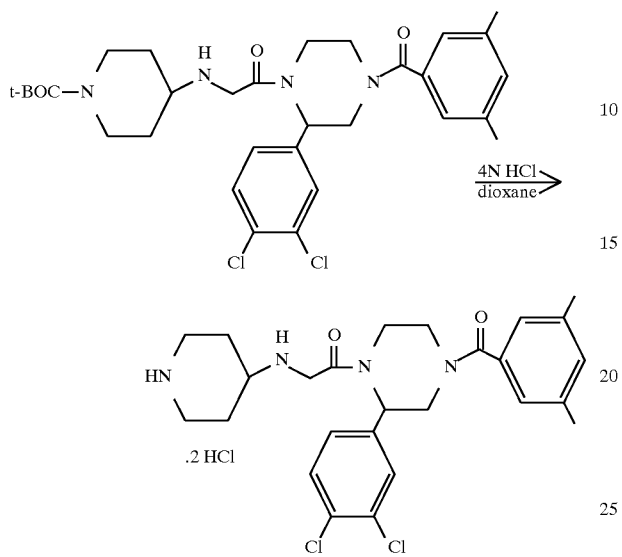

To a solution of (+,-)-1,1-dimethylethyl-4-[[2-[2-(3,4-dichlorophenyl)-1-(3,5-dimethylbenzoyl)-1-piperazinyl]-2-oxoethyl]amino]-1-piperidinecarboxylate (Example 7) (2.5 g, 4.14 mmol) in $CH_2Cl_2$ (20 mL) at 0° C. was added 4N

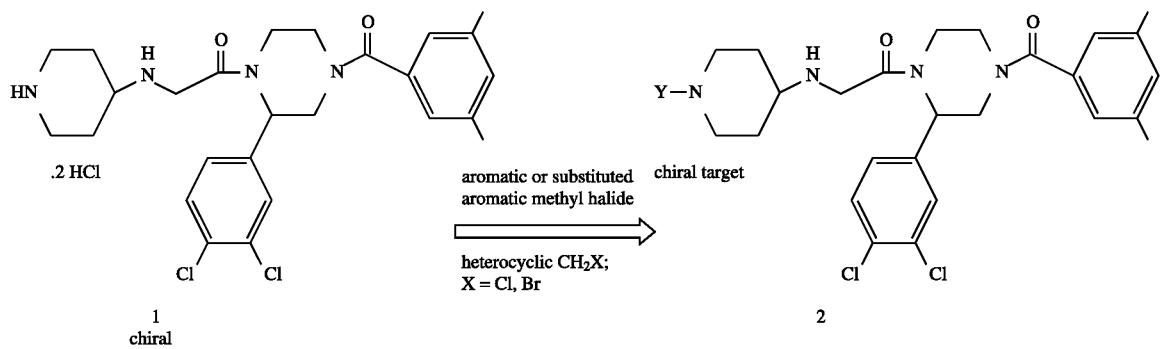

HCl-dioxane (10.35 mL, 41.4 mmol). The mixture was stirred at 0° C. for 1 h and it was gradually warmed to RT over 3 h. After reaction was complete, excess HCl and solvent were evaporated to give a pale yellow solid which was used without further purification. FAB MS $[M+1]^{+\ 35}Cl$ 503.1.

EXAMPLE 10

Preparation of (-)-2-(3,4-dichlorophenyl)-4-[3,5-dimethylbenzoyl]-1-[(4-piperidinyl-amino)acetyl] piperazine, dihydrochloride (Enantiomer B)

By employing method analogous to that described in Example 9 using chiral material obtained from Example 8, the title compound was obtained as a pale yellow solid, FAB MS $[M+1]^{+\ 35}Cl$ 503.2;

$[\alpha]_D^{22.1°\ C.} = -38°(MeOH)$.

EXAMPLE 11

A series of Y derivatives of (-)-2-(3,4-dichlorophenyl)-4-[3,5-dimethylbenzoyl]-1-[(4-piperidinylamino)acetyl] piperazine, dihydrochloride (Enantiomer B) was prepared by parallel synthesis.

To a suspension of compound 1 obtained from Example 10 (1.05 g, 1.822 mmol) in $CH_2Cl_2$ (40 mL) was added Hünig's base (1.0 mL 5.74 mmol). The mixture was dissolved by sonication. This solution was divided into 20 parts and transferred into 20 vials. Each vial contained 2-(3,4-dichlorophenyl)-4-[3,5-dimethylbenzoyl]-1-[(4-piperidinylamino)acetyl]piperazine, dihydrochloride (Enantiomer B) (0.091 mmol), Hünig's base (0.287 mmol) and $CH_2Cl_2$ (2 mL). To each vial was added separately 0.1 mmol of aromatic or substituted aromatic methyl chloride or bromide or heterocyclic halide reagent. After reaction was complete it was diluted with $CH_2Cl_2$ (5 mL), washed with brine (2 mL 3x), dried ($MgSO_4$), filtered and evaporated to dryness.

Representative compounds 2 made by the above routes are shown below.
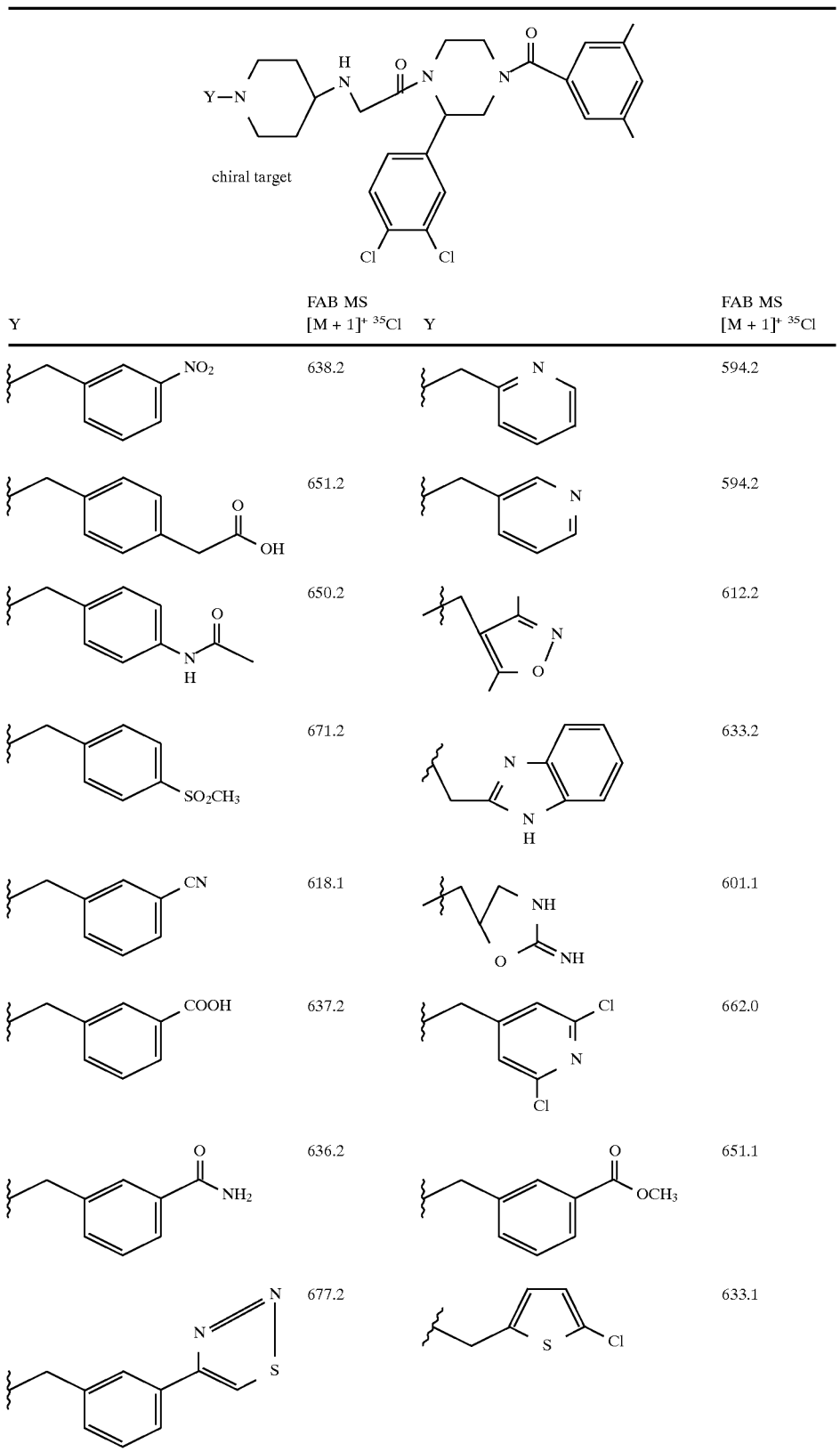

-continued

| Y | FAB MS [M + 1]+ 35Cl | Y | FAB MS [M + 1]+ 35Cl |
|---|---|---|---|
| 3-iodobenzyl | 673.9 | 2-chloro-6-(2-chlorovinyl)pyrimidin-4-yl methylene | 663 |
| quinolin-2-ylmethyl | 644.2 | | |
| 2-cyclopropyl-6-hydroxypyrimidin-4-yl methylene | 651.1 | 3,5-dimethylisoxazol-4-yl (N-oxy)methylene | 680.1 |
| 6-hydroxy-2-(thiophen-2-yl)pyrimidin-4-ylmethyl | 693.1 | 5-(methoxycarbonyl)furan-2-ylmethyl | 641.1 |
| thiophen-2-yl-(N-oxy)methylene | 667.1 | 1,2,4-oxadiazol-3-ylmethyl | 585.1 |
| 6-hydroxy-2-(pyridin-2-yl)pyrimidin-4-ylmethyl | 688.1 | 5-methylisoxazol-3-yl (N-oxy)methylene | 679.1 |

EXAMPLE 12

Preparation of (+,−)-1-benzoyl-4-[[2-[2-(3,4-dichlorophenyl)-4-(3,5-dimethylbenzoyl)-1-piperazinyl]-2-oxoethyl]amino]piperidine

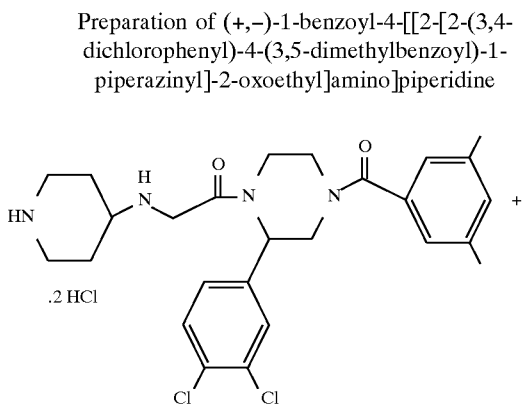

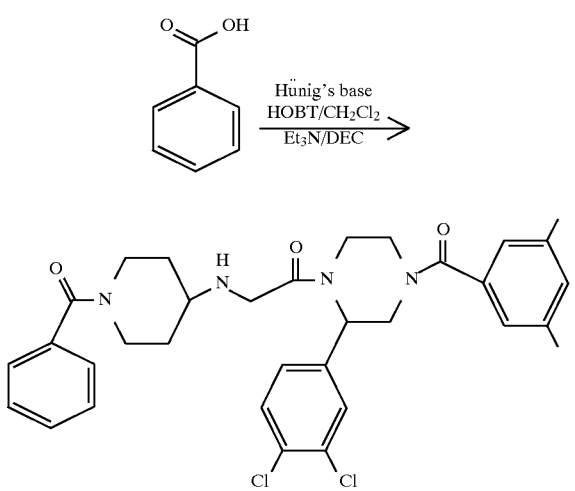

To a solution of compound obtained from Example 9 (0.23 g, 0.4 10 mmol) in CH$_2$Cl$_2$ (5 mL) was added Hünig's base (0.13 g, 1.0 mmol). This was followed by the addition of benzoic acid (49 mg, 0.4 mmol), HOBT (54 mg, 0.4 mmol), Et$_3$N (40 mg, 0.4 mmol) and DEC (77 mg, 0.4 mmol) at 0° C. The solution was gradually warmed to RT and stirred overnight. After reaction was complete, the solution was diluted with CH$_2$Cl$_2$ (50 mL) and washed with saturated NaHCO$_3$ solution (30 mL, 2×) and brine (20 mL, 3×). The organic layer was dried over MgSO$_4$, filtered and concentrated to give crude material as an oil. The product was purified by chromatography on flash grade silica gel (50 g), eluting with 5% [NH$_4$OH/MeOH (1:9)]/CH$_2$Cl$_2$ to give the title compound as a white solid (0.18 g), m.p. 94°–96° C.; FAB MS [M+1]$^+$ $^{35}$Cl 607.3.

EXAMPLE 13

Preparation of (+,−)-2-(3,4-dichlorophenyl)-4-(3,5-dimethylbenzoyl)-1-[[[1-(2-oxo-2-phenylethyl)-4-piperidinyl]amino]acetyl]piperazine

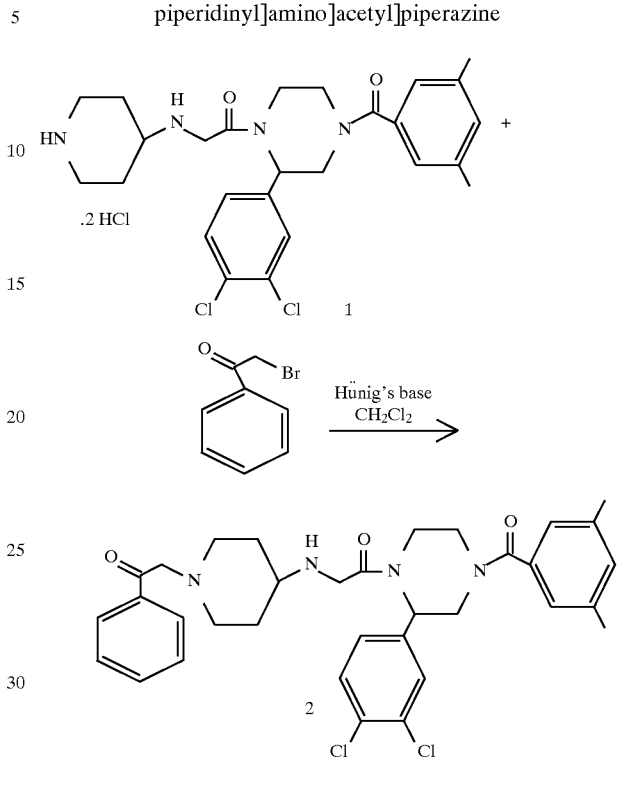

To a solution of compound 1 obtained from Example 9 (0.23 g, 0.4 mmol) in CH$_2$Cl$_2$ (5 mL) were added Hünig's base (0.21 g, 1.6 mmol) and phenylacyl bromide (80 mg, 0.4 mmol) at RT. The mixture was stirred at RT overnight under N$_2$. After reaction was complete, it was worked up and purified according to the methods described in Example 7 to give the title compound 2 as a solid, m.p. 69°–71° C.; FAB MS [M+1]$^+$ $^{35}$Cl 621.3.

EXAMPLE 14

Preparation of (+,−)-2-(3,4-dichlorophenyl)-4-(3,5-dimethylbenzoyl)-1-[[[1-(3-phenylpropyl)-4-piperidinyl]amino]acetyl]piperazine

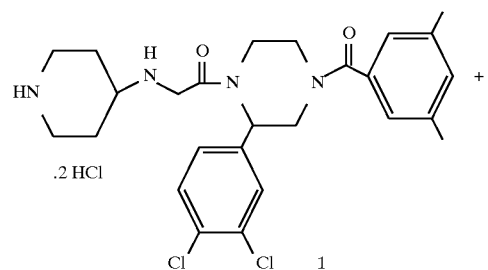

-continued

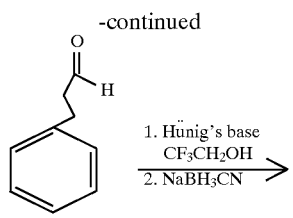

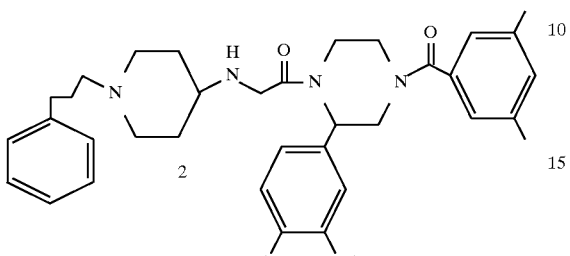

To a solution of compound 1 obtained from Example 9 (0.4 g, 0.7 mmol) in CF$_3$CH$_2$OH (5 mL) was added Hünig's base (0.21 g, 1.6 mmol) at 0° C. After stirring at 0° C. for 10 min, hydrocinnamaldehyde (94 mg, 0.7 mmol) was added. The reaction was stirred at 0° C. for additional 2.5 h, and NaBH$_3$CN (100 mg, 1.6 mmol) was added. The mixture was stirred at 0° C. and gradually warmed to RT overnight. After reaction was complete, it was worked up and purified as described in Example 7 to give the title compound as a white solid, m.p. 52°–54° C.; FAB MS [M+1]$^+$ $^{35}$Cl 621.3.

EXAMPLE 15

Preparation of (−)-N-[4-[[4-[[2-[2-(3,4-dichlorophenyl)-4-(3,5-dimethylbenzoyl)-1-piperazinyl]-2-oxoethyl]amino]-1-piperidinyl]methyl]-2-thiazoyl]acetamide (Enantiomer B)

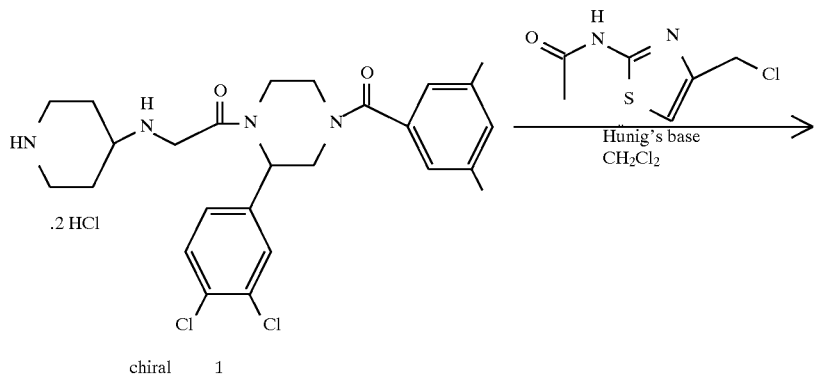

By an analogous method to that described in Example 13, using the chiral intermediate 1 made in Example 10 and 2-acetamido-4-(chloromethyl)-thiazole, in the present of Hünig's base in CH$_2$Cl$_2$, the title compound 2 was obtained as a white solid after purification by flash grade silica gel chromatography, m.p. 104°–107° C., HRMS Calcd. for [M+H$^+$]$^{(2\times35)}$Cl C$_{32}$H$_{39}$N$_6$SO$_3$Cl$_2$ 657.2181; Found 657.2172;

$[\alpha]_D^{24.1°\,C.}=-40.1°$(MeOH).

EXAMPLE 16

Preparation of (+,−)-2-(3,4-dichlorophenyl)-4-[3,5-dimethylbenzoyl]-1-[[[3-methyl-1-(phenylmethyl)-4-piperidinyl]amino]acetyl]piperazine (diastereomers A and B)

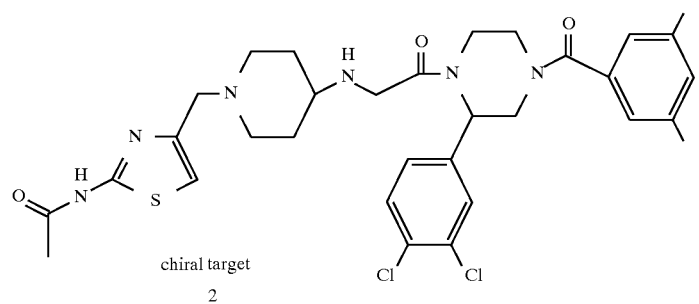

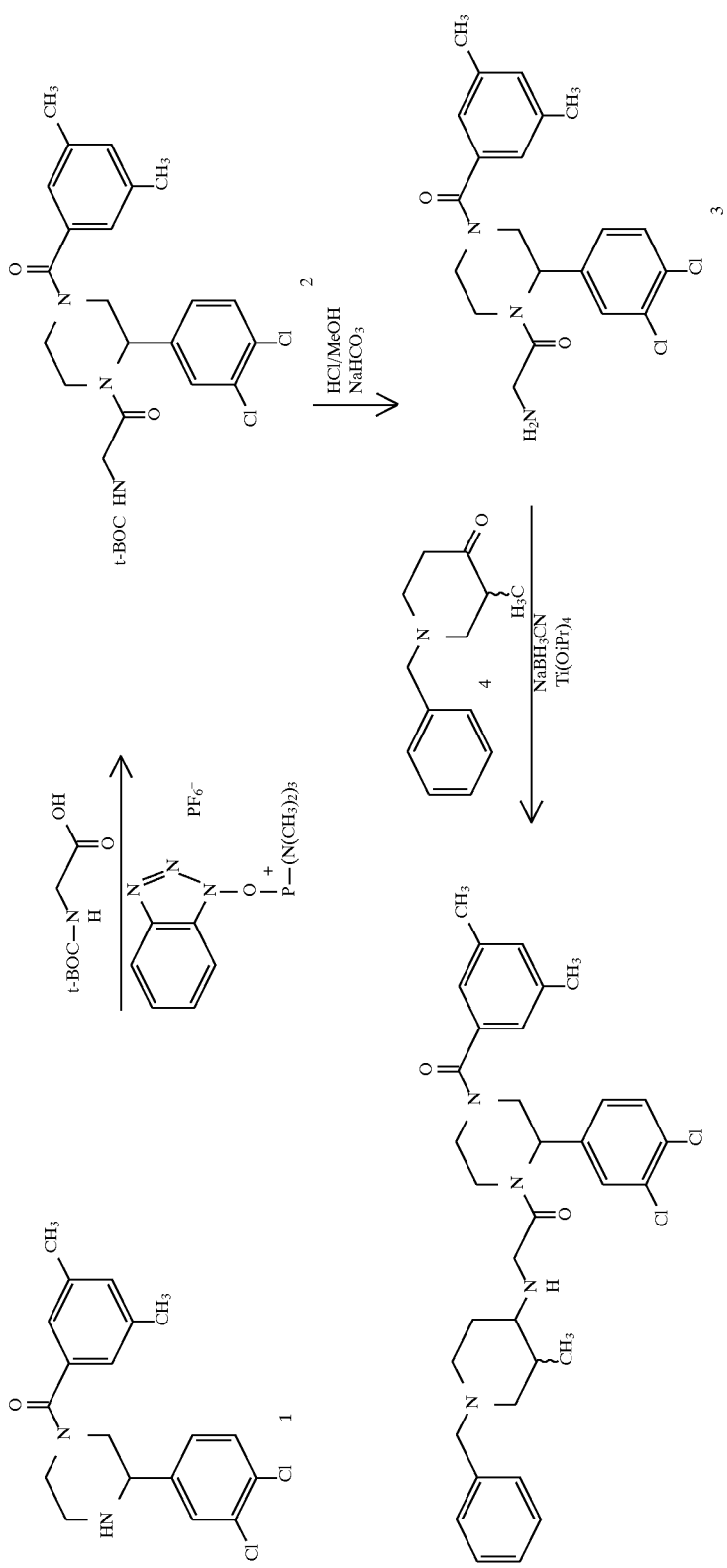

Step 1

To a solution of BOC glycine (0.979 g, 5.59 mmol) and Et₃N (0.85 mL, 6.1 mmol) in CH₂Cl₂ (10 mL) was added BOP (benzotriazol-1-yloxy-tris(dimethylamino)phosphonium hexafluorophosphate) reagent (2.46 g, 5.57 mmol). After stirring for 15 min, (+,–)-(3,5-dimethylbenzoyl)-3-(3,4-dichlorophenyl)piperazine (1.83 g, 5.03 mmol) (prepared in Example 2) was added. After 5 h, the reaction mixture was added to 0.2N HCl (100 mL) and extracted with CH₂Cl₂ (3×60 mL). The combined organic layers were washed with brine, dried with MgSO₄ and concentrated. The crude material was purified by flash chromatography on silica gel eluting with 50:1 to 30:1 CH₂Cl₂—MeOH to give 2.15 g of compound 2 (shown above) as a white foam (4.1 mmol, 82%).

Step 2

Compound 2 (1.32 g, 2.5 mmol) was treated with MeOH saturated HCl (15 mL) for 2.5 h and concentrated. The resulting powder was dissolved in CH₂Cl₂, washed with sat. NaHCO₃, dried with MgSO₄ and concentrated to give compound 3 as the free base.

Step 3

To a –78° C. solution of LDA (10.79 mmol) in THF (30 mL) was added 1-benzyl-4-piperidone (2.0 mL, 10.8 mmol). The reaction mixture was warmed to 0° C. for 20 min and then cooled back to –78° C. Methyl iodide (0.67 mL, 10.8 mmol) was added to the enolate solution which was stirred at 0° C. for 2 h then warmed to RT overnight. The reaction mixture was quenched with sat. NH₄Cl and concentrated. The residue was suspended in H₂O and extracted with CH₂Cl₂. The combined organic layers were dried with MgSO₄, filtered and concentrated. The product was purified by flash chromatography on silica gel eluting with 1:1 hexane-EtOAc to give the 1-benzyl-3-methyl-4-piperidone 4 as a yellow oil (0.65 g, 30%).

Step 4

A mixture of the ketone 4 from step 3 (70 mg, 0.13 mmol) and the compound 3 (34 mg, 0.17 mmol) was stirred in titanium isopropoxide (45 mg, 0.16 mmol) for 1.5 h. To the mixture were added ethanol (1.0 mL) and NaCNBH₃ (5.4 mg, 8.6 mmol) and the mixture was stirred overnight. The reaction mixture was filtered and washed with EtOAc. The filtrate was washed with H₂O and brine, dried with MgSO₄ and concentrated. The residue was chromatographed on silica gel eluting with 5% NH₃ sat. MeOH in CH₂Cl₂ to give both diastereomers pure.

Diastereomer A (15 mg) HRMS (FAB, M+H⁺): m/e calc'd for [C₃₄H₄₁N₄Cl₂O₂]⁺ 607.2607; found 607.2603.

Diastereomer B (17 mg) HRMS (FAB, M+H⁺): m/e calc'd for [C₃₄H₄₁N₄Cl₂O₂]⁺ 607.2607; found 607.2597.

EXAMPLE 17

Preparation of 2-(3,4-dichlorophenyl)-4-[3,5-dimethylbenzoyl]-1-[[[1-(phenylmethyl)-3-piperidinyl]amino]acetyl]piperazine, diastereomers

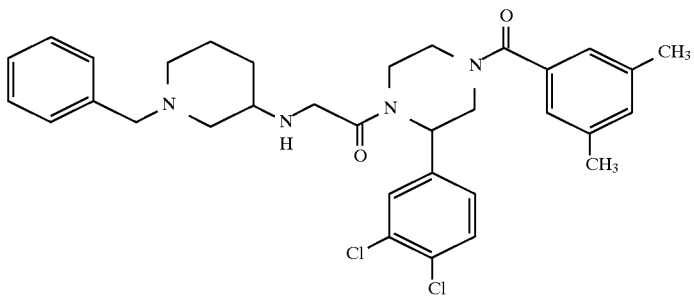

By a procedure analogous to the method described in Example 16 step 4, using 3-benzyl piperidine in place of 1-benzyl-3-methyl-4-piperidone, the title compound was prepared as a solid foam.

HRMS (FAB, M+H⁺): m/e calc'd for [C₃₃H₃₉N₄Cl₂O₂]⁺ 593.2450; found 593.2458.

EXAMPLE 18

Preparation of 2-(3,4-dichlorophenyl)-4-(3,5-dimethylbenzoyl)-1-[[[8-(phenylmethyl)-8-azabicyclo[3.2.1]oct-3-yl]amino]acetyl]piperazine

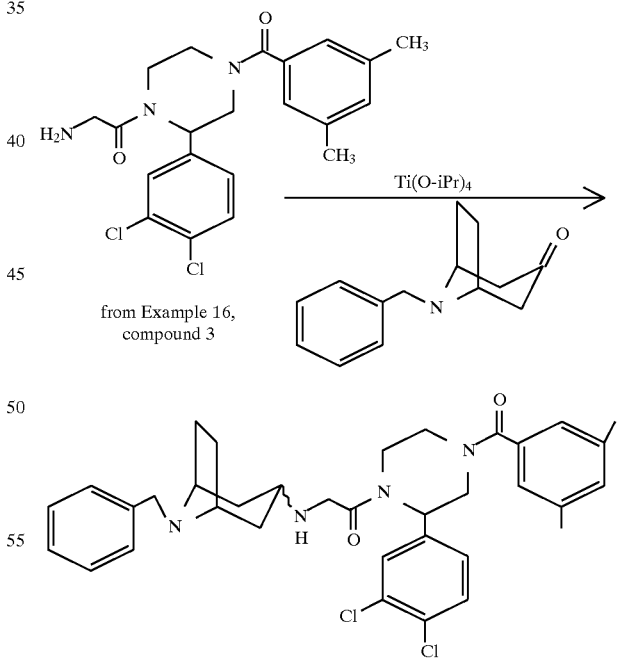

from Example 16, compound 3

By an analogous method to that described in Example 16, the product from Example 16, compound 3 (185 mg, 0.44 mmol) was combined with 8-benzyl-8-azabicyclo[3.2.1]octan-3-one (97 mg, 0.45 mmol) and Ti(O-i Pr)₄ (105 mL, 0.50 mmol) and left stirring for 1 h. To the thick reaction mixture was added NaBH₃CN (59.5 mg, 0.95 mmol) and the mixture was stirred overnight. To the reaction mixture was added H₂O (1 mL) and it was filtered. The filtrate was washed with EtOH, concentrated and purified by silica gel chromatography, eluting with 30:1:0.1 to 15:1:0.1 CH₂Cl₂—MeOH—NH₃ aq. to give the title product as a white foam. HRMS (FAB, M+H⁺); m/e calc'd [C₃₅H₄₁Cl₂N₄O₂]⁺: 619.2607, found 619.2594.

EXAMPLE 19

Preparation of 2-(3,4-dichlorophenyl)-4-(3,5-dimethylbenzoyl)-1-[[[8-methyl-8-azabicyclo[3.2.1]oct-3-yl]amino]acetyl]piperazine (enantiomer B)

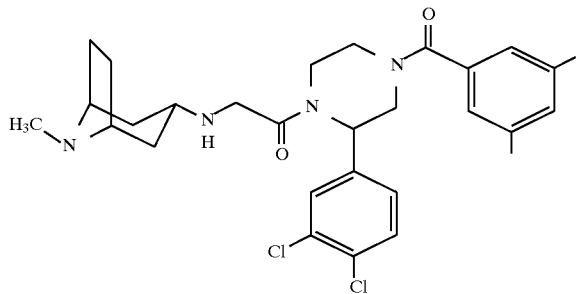

This compound was prepared by a procedure analogous to Example 16 except for the use of (+)-[3,5-dimethylbenzoyl]-3-(3,4-dichlorophenyl)-piperazine (Enantiomer B) in step 1 and tropinone in place of 1-benzyl-3-methyl-4-piperidone. HRMS (FAB, M+H⁺); m/e calc'd [C₂₉H₃₇Cl₂N₄O₂]⁺: 543.2294, found 543.2282.

EXAMPLE 20

Preparation of 2-(3,4-dichlorophenyl)-4-[3,5-dimethylbenzoyl]-1-[[[1,3-bis(phenylmethyl)-4-piperidinyl]amino]acetyl]piperazine, diastereomers from enantiomer B

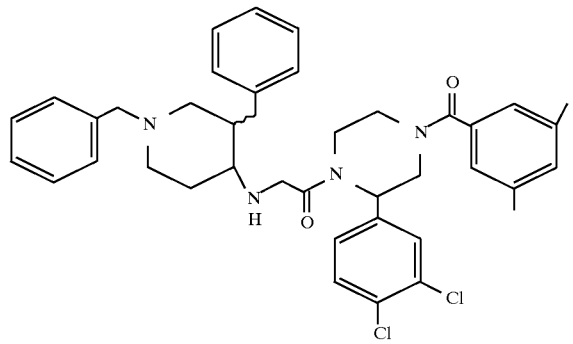

Step 1. A solution of 1-benzyl-3-carbomethoxy-4-piperidone (1.0 g, 4.0 mmol) in THF (10 mL) was treated with 0.5M potassium bis(trimethylsilyl)amide in toluene (9.6 mL, 4.8 mmol) for 15 min, followed by the addition of benzyl bromide (1.2 g, 4.8 mmol). After 2 h, the reaction mixture was quenched with sat. NH₄Cl and extracted with ether. The combined organic layers were washed with brine, dried with MgSO₄ and concentrated. The product was purified by silica gel chromatography eluting with 4:1 hexane-EtOAc to give 3-carbomethoxy-1,3-dibenzyl-4-piperidone (0.61 g) as a light yellow oil.

Step 2. A solution of 3-carbomethoxy-1,3-dibenzyl-4-piperidone (0.61 g, 1.78 mmol), MeOH (10 mL) and 5M HCl aq. (25 mL, 125 mmol) was refluxed overnight. The reaction mixture was concentrated and chromatographed (silica gel, eluting with 4:1 hexane-EtOAc) to give 1,3-dibenzyl-4-piperidone (0.31 g).

Step 3. A solution of 1,3-dibenzyl-4-piperidone (0.033 g, 0.12 mmol) and [[2-(3,4-dichlorophenyl)-4-(3,5-dimethylbenzoyl)-1-amino]acetyl]-piperiazine (Enantiomer B) (0.05 g, 0.12 mmol) [prepared according to the methods described in Example 16, except using (+)-[3,5-dimethylbenzoyl]-3-(3,4-dichlorophenyl)piperazine (Enantiomer B) (Example 4) in step 1] in CH₂Cl₂ (1.0 mL) was treated with NaBH(OAc)₃ (0.035 g, 0.16 mmol) and acetic acid (0.07 mL, 0.12 mmol). The mixture was stirred overnight. After completion, the reaction mixture was quenched with 1N NaOH and extracted with CH₂Cl₂. The combined organic extracts were washed with brine, dried with MgSO₄, concentrated and purified by silica gel chromatography, eluting with 5% NH₃ sat. MeOH/CH₂Cl₂ to give 32 mg of the titled product as a white solid. HRMS (FAB, M+H⁺); m/e calc'd [C₄₀H₄₅Cl₂N₄O₂]⁺: 683.2920, found 683.2932.

EXAMPLE 21

Preparation of 2-(3,4-dichlorophenyl)-4-[3,5-dimethylbenzoyl]-1-[[[3-methyl-1-(phenylmethyl)-4-piperidinyl]amino]acetyl]piperazine (diastereomers A from enantiomer B)

This compound was prepared by a procedure analogous to Example 16 except for the using of (+)-[3,5-dimethylbenzoyl]-3-(3,4-dichlorophenyl)-piperazine (Enantiomer B) in Example 16, step 1. HRMS (FAB, M+H⁺); m/e calc'd [C₃₄H₄₁Cl₂N₄O₂]⁺: 607.2607, found 607.2594.

EXAMPLE 22

Preparation of 2-(3,4-dichlorophenyl)-4-[3,5-dimethylbenzoyl]-1-[[[1-(phenylmethyl)-3-(2-propenyl)-4-piperidinyl]amino]acetyl]piperazine (diastereomers from enantiomer B)

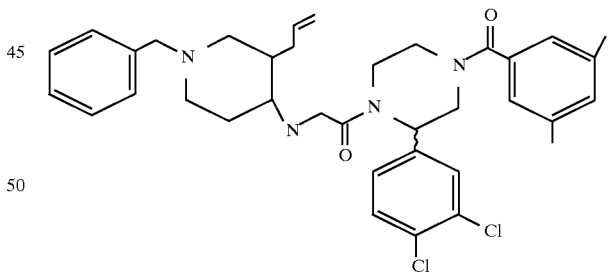

This compound was prepared by a procedure analogous to Example 20 except for the substitution of allyl bromide in place of benzyl bromide in step 1. HRMS (FAB, M+H⁺); m/e calc'd [C₃₆H₄₃Cl₂N₄O₂]⁺: 633.27, found 633.2763.

EXAMPLE 23

Preparation of trichloroethyl-4-[[2-(3,4-dichlorophenyl)-4-(3,5-dimethylbenzoyl)-1-piperazinyl]-2-oxoethyl]amino]-2-phenyl-1-piperidinecarboxylate (diastereomers from enantiomer B)

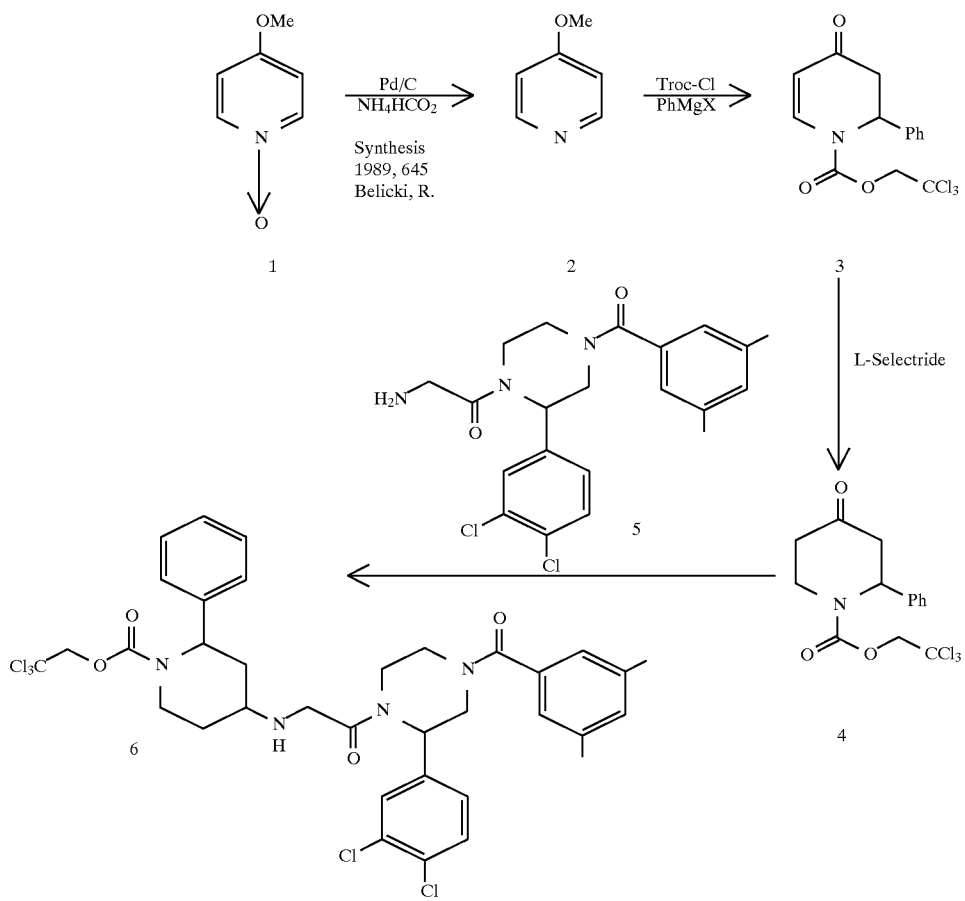

Step 1. To a cooled solution of THF (100 mL) containing 4-methoxypyridine (3.5 g, 32.5 mmol) (prepared according to *Synthesis* 1989, 645, at −15° C. was added 2,2,2-trichloroethyl chloroformate (4.5 mL, 32.7 mmol). After 30 min. at −15° C., 2M PhMgCl in THF (19.5 mL, 39 mmol) was added and the mixture was stirred at −15° C. for 30 min. followed by 30 min. at RT. The reaction mixture was quenched with 10% aq. HCl (100 mL), added to brine (200 mL) and partitioned. The aqueous layer was extracted with Et$_2$O (50 mL). The combined organic layers were dried with MgSO$_4$ and concentrated to give 11.4 g of compound 3 shown above as a light tan solid.

Step 2. To a cooled solution of compound 3 from step 1 (8.65 g, 34.8 mmol) in THF (100 mL) at −23° C. was added 27.8mL of 1M L-selectride (27.8 mmol). The mixture was stirred at −23° C. for 2 h. After warming to RT, the reaction mixture was added to sat. NaHCO$_3$ and partitioned. The aqueous layer was extracted with Et$_2$O (2×50 mL). The combined organic layers were washed with brine (50 mL), dried with MgSO$_4$ and concentrated. The product was purified by silica gel chromatography eluting with 6:1 to 3:1 hexane-EtOAc to give 2.47 g of compound 4 and 2.75 g of recovered starting material.

Step 3. To a solution containing the compound 4 from step 2 (284 mg, 0.81 mmol) in 1,2-dichloroethane (3 ml) and compound 5 (324 mg, 0.81 mmol) [made in Example 16, step 3 except using (+)-[3,5-dimethylbenzoyl]-3-(3,4-dichlorophenyl)piperazine (Enantiomer B) in step 1] was added NaBH(OAc)$_3$ (179 mg, 0.84 mmol) and acetic acid (50 mL, 0.87 mmol). After stirring overnight, the reaction mixture was added to 1N NaOH (40 mL) and was extracted with Et$_2$O (3×15 mL). The combined organic layers were washed with brine (15 mL), concentrated, and purified by silica gel chromatography eluting with 25:1:0.1 CH$_2$Cl$_2$—MeOH—NH$_3$ aq to give 423 mg of the title compound as a white foam. HRMS (FAB, M+H$^+$); m/e calc'd [C$_{35}$H$_{38}$Cl$_4$N$_4$O$_4$]$^+$: 753.1336, found 753.1338.

EXAMPLE 24

Preparation of 2-(3,4-dichlorophenyl)-4-(3,5-dimethylbenzoyl)-1-[3-[5-(phenylmethyl)-(1S,4S)-2,5-diazabicyclo[2.2.1]heptane-2-yl]-1-oxopropyl] piperazine (diastereomer A from enantiomer B)

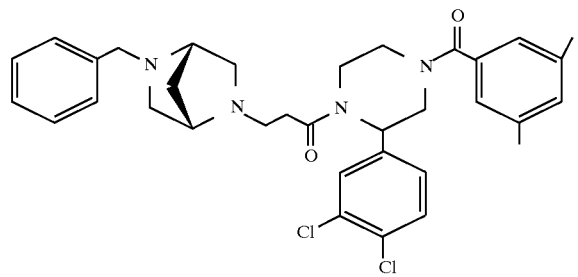

To a cooled solution of CH$_2$Cl$_2$ (10 mL) containing diisopropylethylamine (0.275 mL, 2.0 mmol) and [3,5-dimethylbenzoyl]-3-(3,4-dichlorophenyl)piperazine (Enantiomer B) (Example 4) (305 mg, 0.84 mmol) was added chloropropionyl chloride (0.075 mL, 0.8 mmol). The reaction mixture was allowed to warm to room temperature. After 20 minutes, (1S,4S)-2-benzyl-2,5-diazabicyclo(2.2.1) heptane 2HBr (297 mg, 0.85 mmol) and diisopropylethylamine (0.275 mL, 2.0 mmol) were added and the mixture was left over night, after which the reaction mixture was concentrated. The product was purified by flash chromatography on flash grade silica gel, eluting with 30:1:0.1 $CH_2Cl_2$/MeOH/$NH_3$ to give a foamy solid (140 mg, 0.23 mmol, 29%), High Res. MS:$[M+1]^+$calcd. for $C_{34}H_{39}Cl_2N_4O_2$ 605.2450; Found, 605.2465.

EXAMPLE 25

Preparation of

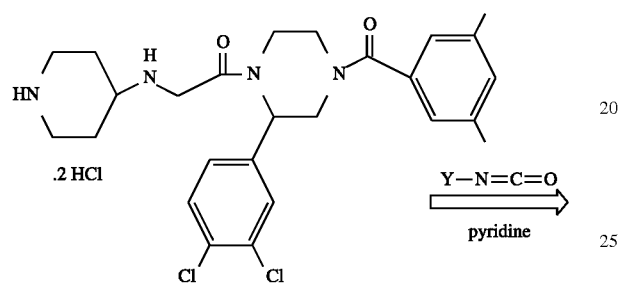

Example 10
chiral

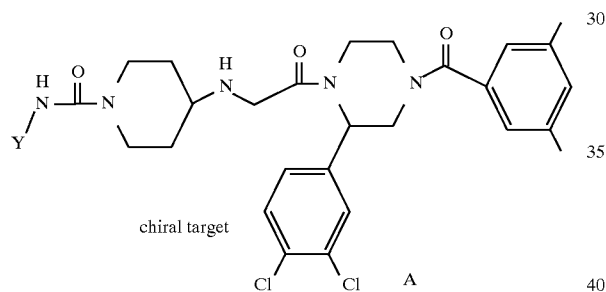

chiral target

A y = aromatic or substituted
aromatic or cycloalkyl group and

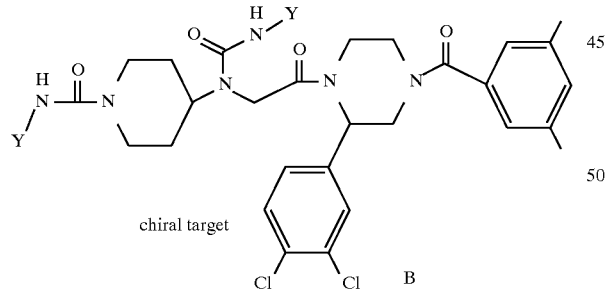

chiral target

B y = aromatic or substituted
aromatic or cycloalkyl group

A series of urea analogs of (−)-2-(3,4-dichlorophenyl)-4-[3,5-dimethylbenzoyl]-1-[(4-piperidinyl-amino)acetyl] piperazine, dihydrochloride (Enantiomer B) (Example 10) as shown above was prepared by parallel synthesis. The product from Example 10 (0.75 g, 1.3 mmol) was dissolved in dry pyridine (13 mL). 1 ml of the above solution was transferred into a vial (2 dram size). To each vial was added 0.1 mmol of an aromatic or substituted aromatic isocyanate reagent. After completion the reaction was diluted with $CH_2Cl_2$ (5 mL) and washed with water (3×5 mL), dried over $Na_2SO_4$, filtered and evaporated to dryness. Most of reactive reagents gave (2:1) adduct B as the major product. Several less reactive reagents gave the product A. Crude products were identified by FAB MS.

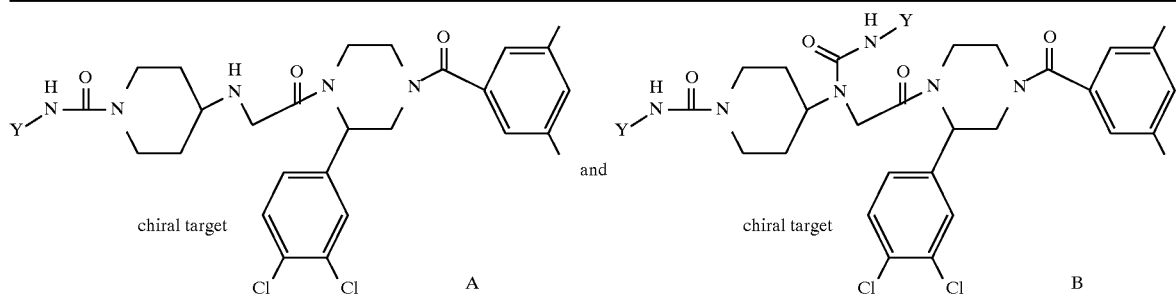
y = aromatic or substituted aromatic group or cycloalkyl (both A and B)
| Y | Product | FAB MS [M + 1]+ 35Cl | Y | Product | FAB MS [M + 1]+ 35Cl |
|---|---|---|---|---|---|
| phenyl | B | 741.1 | 4-(ethoxycarbonyl)phenyl | A | 694.4 |
| 3-(SCH₃)phenyl | B | 833.3 | 3,4-dichlorophenyl | A | 692.2 |
| 3,5-dimethylphenyl | B | 797 | 3-methylphenyl | B | 769.3 |
| 4-(OCF₃)phenyl | B | 909 | 3-cyanophenyl | A | 647.3 |
| 4-acetylphenyl | A | 664.3 | 1-phenylethyl | B | 797.4 |
| 2-naphthyl | B / A | 841.4 / 672.3 | cyclohexyl | B | 753.5 |
| 2-(OCH₃)phenyl | B | 801 | | | |

EXAMPLE 26

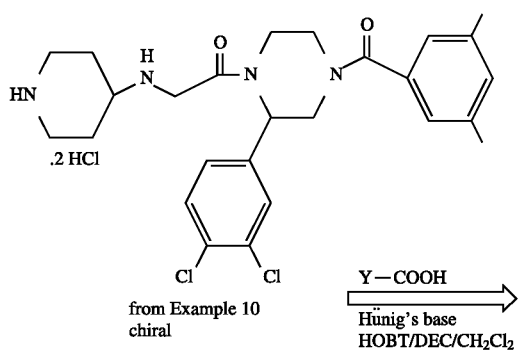

from Example 10
chiral

Y—COOH
⟶
Hünig's base
HOBT/DEC/CH$_2$Cl$_2$

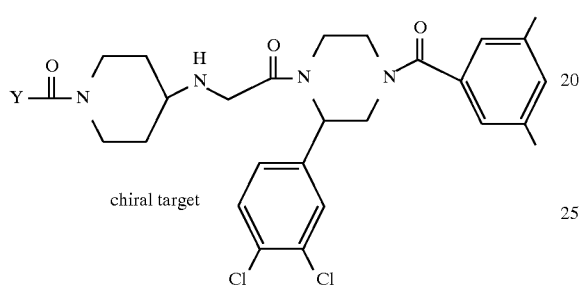

chiral target y = aromatic or substituted aromatic or heterocyclo group

A series of amido analogs of (−)-2-(3,4-dichlorophenyl)-4-[3,5-dimethylbenzoyl-1-[(4-piperidinyl-amino)acetyl] piperazine, dihydrochloride (Enantiomer B) (Example 10) shown above were prepared by parallel synthesis. The chiral product from Example 10 (1.15 g, 2 mmol) was dissolved in a mixture of dry CH$_2$Cl$_2$ (20 mL) and Hünig's base (0.9 g, 7 mmol) followed by the addition of HOBT (0.3 g, 2.2 mmol). After stirring at RT for one hour, 1 mL of this solution was transfered into a brown vial (4 dram size). To each vial was added the appropriate aromatic or heterocyclic acid (0.1 mmol). DEC (0.38 g, 2 mmol) was dissolved in CH$_2$Cl$_2$ (5 mL) and Et$_3$N (0.2 mL) and 0.4 mL(0.2 mmol) of this DEC solution was added into each vial. The reaction was stirred at RT overnight. After completion each reaction mixture was diluted with CH$_2$Cl$_2$ (4 mL) and washed with water (2×4 mL), dried over Na$_2$SO$_4$, filtered and evaporated to dryness. Crude product was identified by FAB MS.

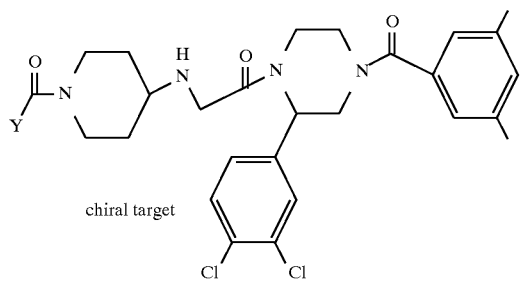

chiral target y = aromatic or substituted aromatic or hetercyclo group

| Y | FAB MS [M + 1]$^+$ $^{35}$Cl | Y | FAB MS [M + 1]$^+$ $^{35}$Cl |
|---|---|---|---|
| phenyl | 607.5 | furyl | 597.7 |
| pyridyl-N-oxide | 624.4 | pyridyl | 607.8 |
| quinoxalinyl | 660.2 | thienyl | 612.7 |

-continued
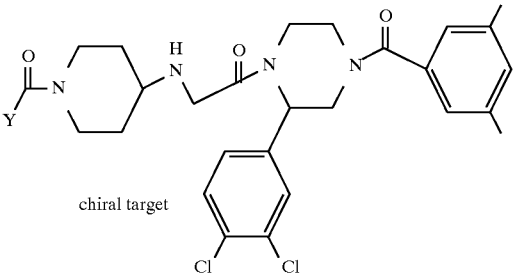
chiral target
y = aromatic or substituted
aromatic or hetercyclo group
| Y | FAB MS [M + 1]+ 35Cl | Y | FAB MS [M + 1]+ 35Cl |
|---|---|---|---|
| 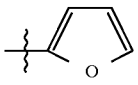 | 597.6 | 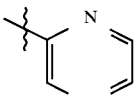 | 608.8 |
| 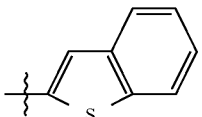 | 663.1 | 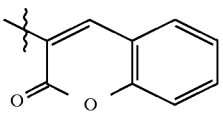 | 674.7 |
| 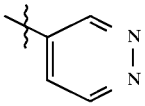 | 609.5 | 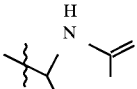 | 614.8 |
| 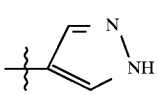 | 597.6 | 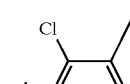 | 698.7 |
|  | 676.3 |  | 682.7 |
| 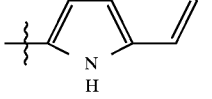 | 658.2 | 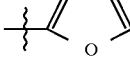 | 677.7 |
| 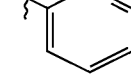 | 613.5 | 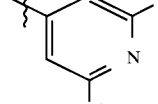 | 607.8 |

EXAMPLE 27

Preparation of (−)-phenyl 4-[[2-[2-(3,4-dichlorophenyl)-4-(3,5-dimethylbenzoyl)-1-piperazinyl-2-oxoethyl]amino]-1-piperidinecarboxylate, hemihydrate (Enantiomer B)

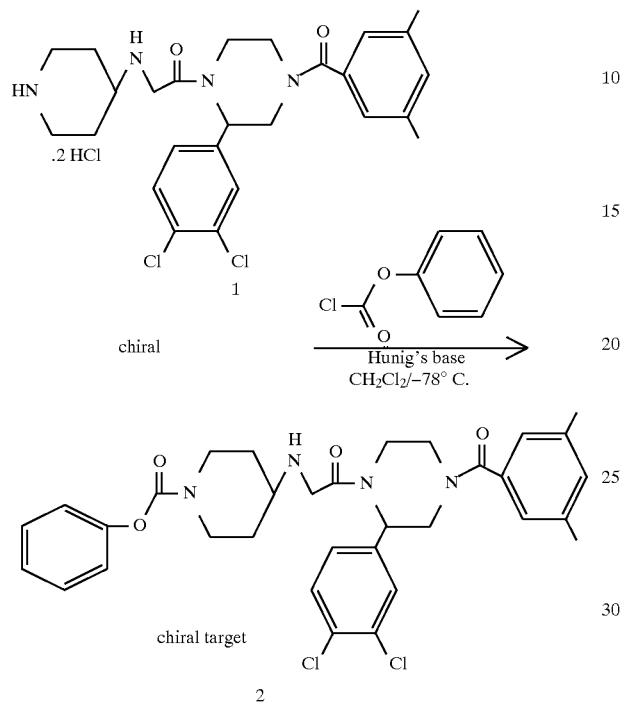

To a cold solution of compound 1 from Example 10 (0.2 g, 0.347 mmol) in CH$_2$Cl$_2$ (8 mL) at −78° C. was added Hünig's base (0.193 mL, 1.11 mmol) and phenylchloroformate (0.046 mL, 0.364 mmol). After stirring at −78° C. for 24 h, the reaction was diluted with CH$_2$Cl$_2$ (200 mL), washed with brine (80 mL, 3×), dried (MgSO$_4$), filtered and evaporated to dryness. The crude material was purified by flash chromatography, using flash grade silica gel (50 g), eluting with 5% [(1:9) (NH$_4$OH/MeOH)]/95% CH$_2$Cl$_2$ to give a 50% yield of the title compound 2 as a white solid (0.108 g, 0.173 mmol), m.p. 71°–75° C.; FAB MS [M+1]$^+$ $^{35}$Cl 623.0; Calcd. for C$_{33}$H$_{36}$N$_4$O$_4$Cl$_2$·0.5 H$_2$O, C, 62.66;H, 5.90; N, 8.86; Cl 11.38.
Found: C, 62.52; H, 5.95; N, 8.87; Cl, 11.01;

$[\alpha]_D^{24.2\,°\,C.}=-42.0°$(MeOH).

EXAMPLE 28

Preparation of 2-(3,4-dichlorophenyl)-4-(3,5-dimethylbenzoyl)-1-[[[1-[(1H-pyrrol-2-yl)methyl]-4-piperidinyl]amino]acetyl]piperazine, hemihydrate (Enantiomer B)

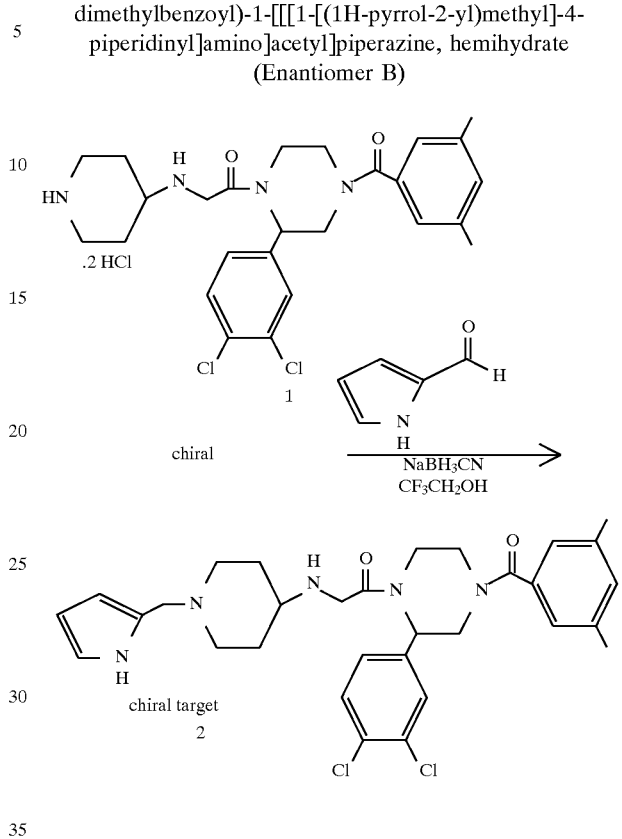

To a solution of compound 1 from Example 10 (0.2 g, 0.347 mmol) in CF$_3$CH$_2$OH (3.47 mL) was added Hünig's base (0.12 mL, 0.694 mmol) and pyrrole-2-carboxaldehyde (40 mg, 0.42 mmol) at RT under nitrogen. After stirring at RT for 1 h, NaBH$_3$CN (67 mg, 0.694 mmol) was added and the mixture was stirred overnight. After the reaction was complete, solvent was evaporated and the residue was mixed with 5% NaHCO$_3$ solution (50 mL) and brine (100 mL) then it was extracted with CH$_2$Cl$_2$ (80 mL,3×). The organic layers were combined, dried (MgSO$_4$), filtered and evaporated to dryness. The crude material was purified by flash chromatography on flash grade silica gel (50 g), eluting with 7.5% [(1 :9)(NH$_4$OH/MeOH)]/92.5% CH$_2$Cl$_2$ to give the title compound 2 in 43% of yield as a white solid, m.p. 73°–76° C.; HRMS, Calcd. for [M+H$^+$] $^{35}$Cl C$_{31}$H$_{38}$N$_5$O$_2$Cl$_2$: 582.2403 Found: 582.2403.

EXAMPLE 29

Preparation of 2-(3,4-dichlorophenyl)-4-(3,5-dimethylbenzoyl)-1-[[[1-[(1 H-pyrrol-2-yl)carbonyl]-4-piperidinyl]amino]acetyl]piperazine, hemihydrate (Enantiomer B)

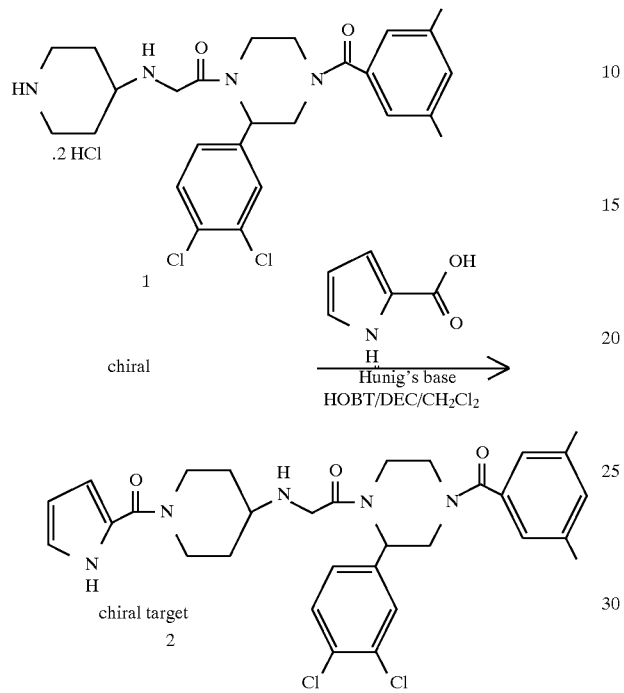

By an analogous method to that described in Example 26, using the chiral compound 1 from Example 10 (100 mg, 0.173 mmol) and pyrrole-2-carboxylic acid (20 mg, 0.178 mmol), the title compound 2 was obtained as a white solid after flash grade silica gel chromatography, m.p. 95°–100° C.; HRMS, Calcd. for [M+H$^+$] $^{35}$Cl, $C_{31}H_{36}N_5O_3Cl_2$: 596.2159 Found: 596.2204.

EXAMPLE 30

Preparation of (−)-2-(3,4-dichlorophenyl)-4-(3,5-dimethylbenzoyl)-1-[[[1-[(1 H-imidazol-2-yl)methyl]-4-piperidinyl]amino]acetyl]piperazine, dihydrate (Enantiomer B)

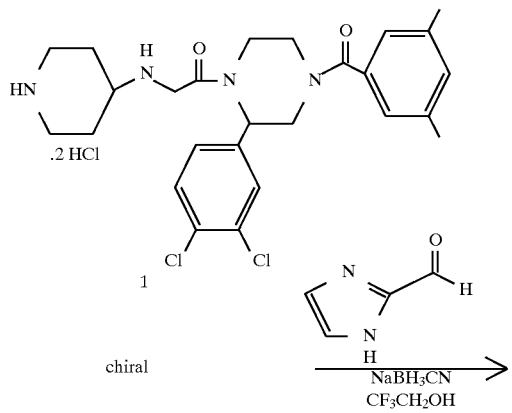

By an analogous method to that described in Example 28, using the chiral compound I from Example 10, (200 mg, 0.347 mmol) and 2-imidazole-carboxaldehyde (34 mg, 0.347 mmol), the title compound 2 was obtained as a white solid after flash grade silica gel chromatography, m.p. 73°–76° C.; HRMS, Calcd. for [M+H$^+$] $^{35}$Cl, $C_{30}H_{37}N_6O_2Cl_2$: 583.2355 Found: 583.2369;

$[\alpha]_D^{23.7°\ C.}=-46.5°$(MeOH).

EXAMPLE 31

Preparation of 2-(3,4-dichlorophenyl)-4-(3,5-dimethylbenzoyl)-1-[1-oxo-3-[[1-(phenylmethyl)-4-piperidinyl]amino]propyl]piperazine (Enantiomer B)

-continued

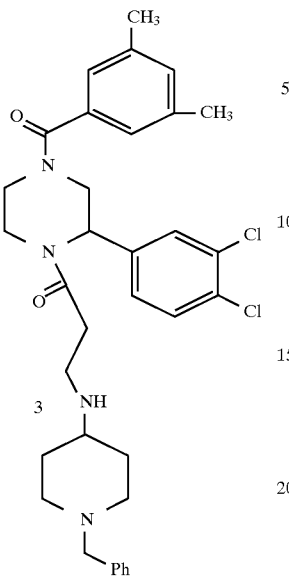

Step 1. To a cold solution of [3,5-dimethylbenzoyl]-3-(3,4-dichlorophenyl)piperazine (Enantiomer B)1 (3.0 g, 8.26 mmol) (Example 4) in CH$_2$Cl$_2$ (82.6 mL) at -78 OC was added Hünig's base (1.582 mL, 9.08 mmol) and bromopropionyl chloride (0.874 mL, 8.67 mmol). After stirring at -78° C. for 5 h, the reaction mixture was diluted with CH$_2$Cl$_2$ (300 mL), washed with brine (150 mL, 2×), dried with MgSO$_4$, filtered and concentrated to dryness to give the crude bromopropionyl intermediate 2 (3.2 g).

Step 2. To a solution of compound 2 (300 mg, 0.6 mmol) in CH$_2$Cl$_2$ (6 mL) were added 4-amino-1-benzyl piperidine (0.245 mL, 1.2 mmol) and Hünig's base (0.1 mL, 0.6 mmol) at 0° C. The reaction was gradually warmed to RT and stirred for 3 days. After completion the reaction mixture was diluted with CH$_2$Cl$_2$ (200 mL) and washed with brine (50 mL, 2×), dried over MgSO$_4$, filtered and concentrated to dryness to give a light yellow solid. The crude material was purified by flash chromatography on flash grade silica gel (80 g), eluting with 6.5% [(1:9) (NH$_4$OH/MeOH)]/93.5% CH$_2$Cl$_2$ to give the title compound as a white solid (0.18 g, 0.3 mmol, 50%), m.p. 51°–54° C.; HRMS, Calcd. for [M+H$^+$] $^{35}$Cl, C$_{34}$H$_{41}$N$_4$O$_2$Cl$_2$: 607.2607 Found: 607.2600.

EXAMPLE 32

Preparation of 2-(3,4-dichlorophenyl)-4-(3,5-dimethylbenzoyl)-1-[1-oxo-3-N-methyl-[[1-(phenylmethyl)-4-piperidinyl]amino]propyl] piperazine (Enantiomer B)

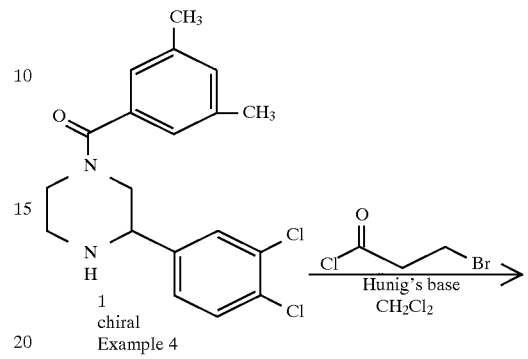

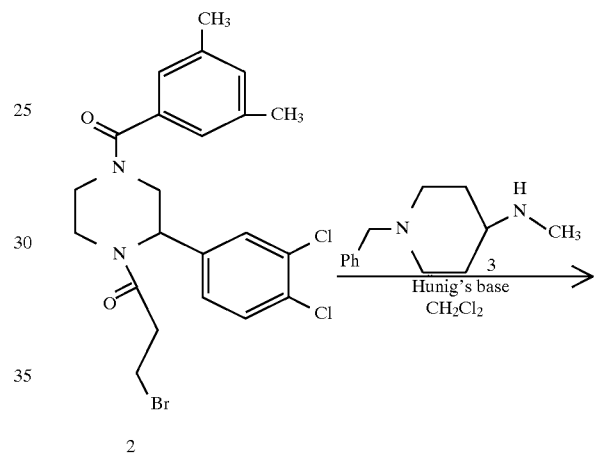

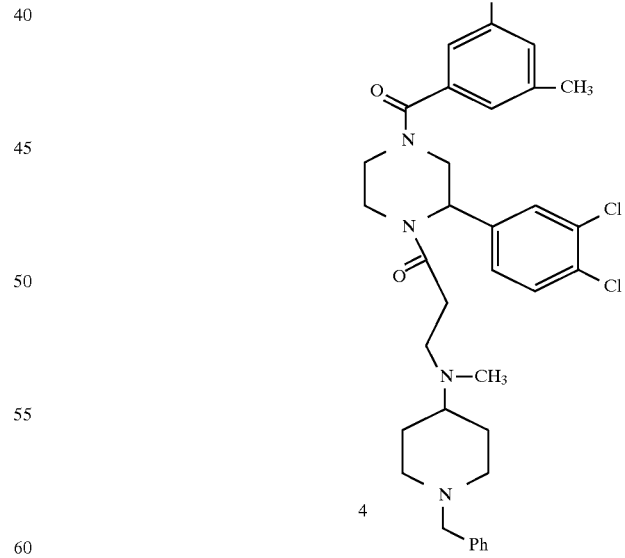

4-Methylamino-1-benzyl piperidine 3 was prepared analogous to the reductive amination method described in Example 28 using 4-amino-1-benzyl piperidine and methylamino hydrochloride as starting materials.

The title compound 4 was prepared as a white soid, analogous to the methods described in Example 31, except using 4-methylamino-1-benzyl piperidine 3 in place of 4-amino-1-benzyl piperidine in step 2. m.p. 47°–49° C.; FAB MS [M+1]$^+$ $^{35}$Cl 621.2; Calcd. for $C_{35}H_{42}N_4O_2Cl_2 \cdot 0.5H_2O$: C, 66.66; H, 6.87; N, 8.88; Cl, 11.24. Found: C, 67.02; H, 7.07; N, 8.81; Cl, 10.75.

EXAMPLE 33

Preparation of (−)-1,2-dimethylethyl 5-[3-[2-(3,4-dichlorophenyl)-4-(3,5-dimethylbenzoyl)-1-piperazinyl]-3-oxopropyl]-(1S,4S)-2,5-diazabicyclo[2.2.1]heptane-2-carboxylate (diastereomer A from enantiomer B)

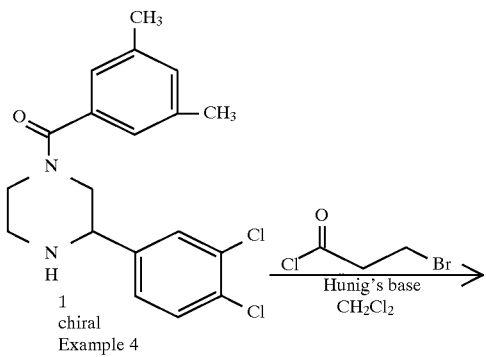

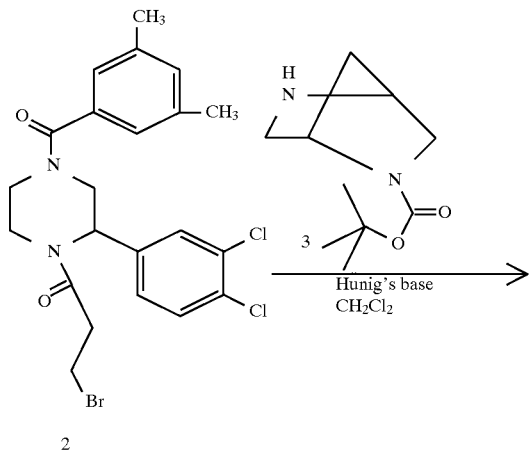

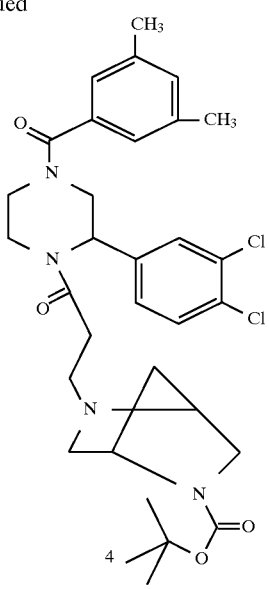

The title compound 4 was prepared as a white solid analogous to the methods described in Example 31 except using (1s,4s)-N-t-BOC-2,5-diazobicyclo[2.2.1]-heptane in place of 4-amino-1-benzyl piperidine in step 2. m.p.78°–82° C.; FAB MS [M+1]$^+$ $^{35}$Cl 615.1;

$[\alpha]_D^{22.0°\ C.} = -51.1°$(MeOH).

EXAMPLE 34

Preparation of (−)-1-[3-(1S,4S)-(2,5-diazabicyclo[2.2.1]heptan-2-yl)-1-oxopropyl]-2-(3,4-dichlorophenyl)-4-(3,5-dimethylbenzoyl) piperazine dihydrochloride (diastereomer A from enantiomer B)

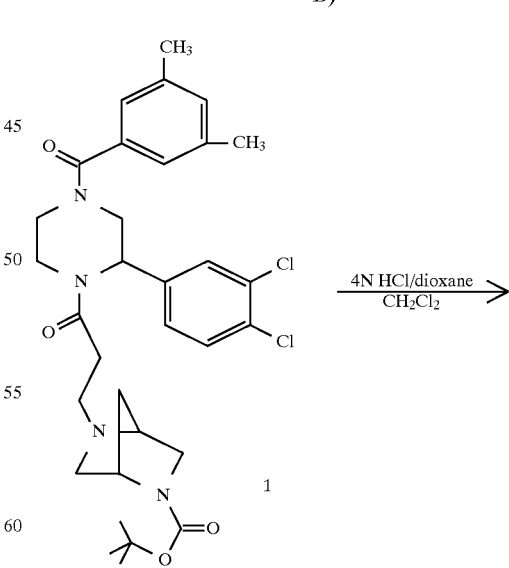

101
-continued

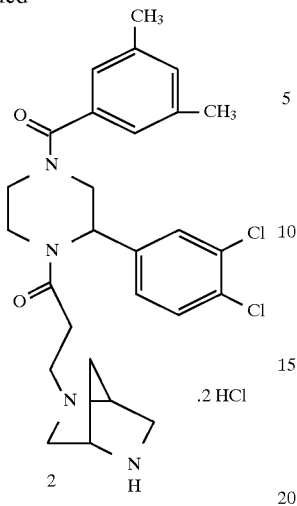

To a solution of compound I obtained from Example 33 (0.74 g, 1.2 mmol) in CH$_2$Cl$_2$ (6 mL) at RT was added 4N HCl (3mL, 12 mmol). After stirring at RT for 4 h, excess acid and solvents were evaporated to give a light yellow solid 2, m.p. 60°–64° C.; FAB MS [M+1]$^+$ $^{35}$Cl 515.1;

$[\alpha]_D^{22.0°\ C.}=-34.4°$(MeOH).

EXAMPLE 35

Preparation of (−)-N-[4-[[5-[3-[2-(3,4-dichlorophenyl-4-(3,5-dimethylbenzoyl]-1-piperazinyl]-3-oxopropyl]-(1S,4S)-2,5-diazabicyclo[2.2.1]heptan-2-yl]methyl-2-thiazolyl]]acetamide (diastereomer A from enantiomer B)

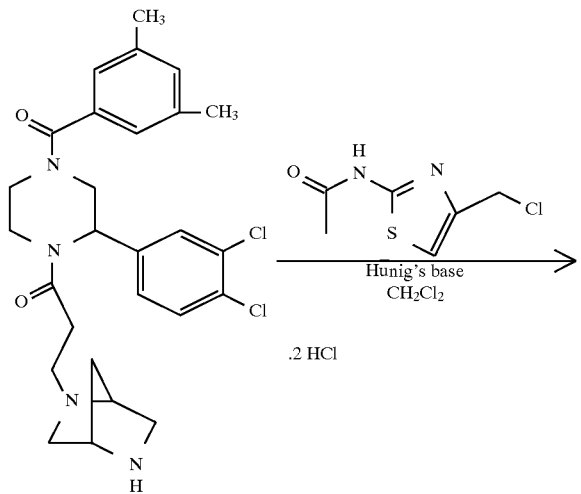

102
-continued

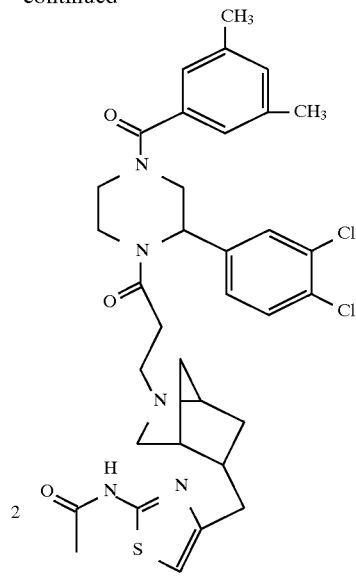

By an analogous method to that described in Example 13, using the chiral intermediate 1 made in Example 34 and 2-acetamido-4-chloromethyl thiazole, in the present of Hünig's base in CH$_2$Cl$_2$, the title compound 2 was obtained as a white solid 2 after purification by flash grade silica gel chromatography, m.p. 105°–110° C.; FAB MS [M+1]$^+$ $^{35}$Cl 669.0;

$[\alpha]_D^{24.7°\ C.}=-23.4°$(MeOH).

EXAMPLE 36

Preparation of (−)-N-[4-[[5-[3-[2-(3,4-dichlorophenyl-4-(3,5-dimethylbenzoyl)-1-piperazinyl]-3-oxopropyl]-(1 S,4S)-2,5-diazabicyclo[2.2.1]heptan-2-yl]methyl]phenyl] acetamide (diastereomer A from enantiomer B)

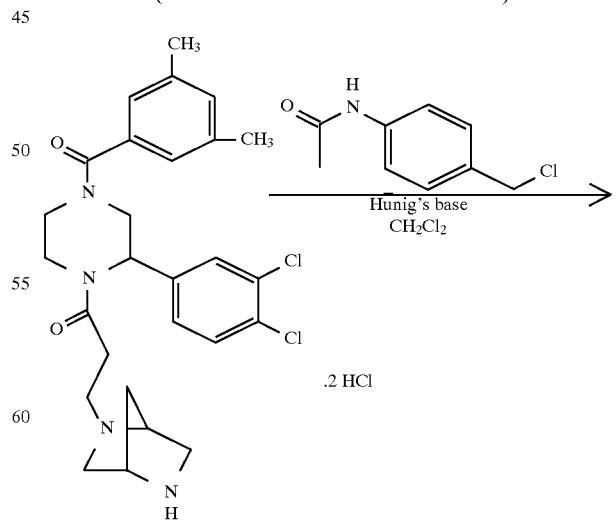

103
-continued

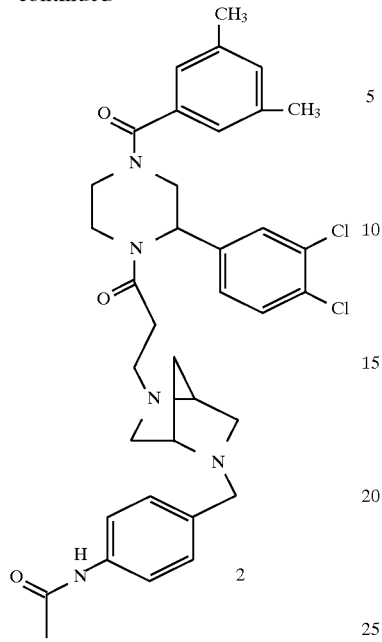

By an analogous method to that described in Example 13, using the chiral intermediate made in Example 34 and 4-acetamidobenzyl chloride, in the present of Hünig's base in $CH_2Cl_2$, the title compound 2 was obtained as a white solid after purification by flash grade silica gel chromatography, m.p. 101°–106° C.; FAB MS $[M+1]^+$ $^{35}Cl$ 662.1;

$[\alpha]_D^{23.3°\ C.} = -27.3°(MeOH)$.

EXAMPLE 37

Preparation of 2-(3,4-dichlorophenyl-4-(3,5-dimethylbenzoyl]-1-[3-[5-(1 H-pyrroll-2-yl)methyl]-(1S,4S)-2,5-diazabicyclo[2.2.1]heptan-2-yl]-1-oxopropyl] piperazine (diastereomer A from enantiomer B)

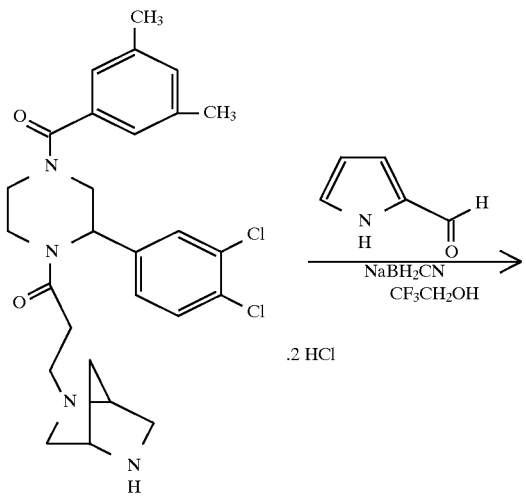

104
-continued

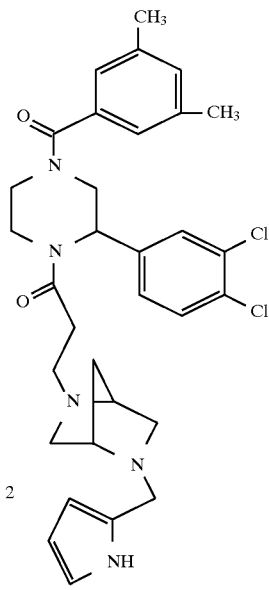

By an analogous method to that described in Example 28, using the chiral intermediate of Example 34, the title compound 2 was obtained as a white solid after purification by flash grade silica gel chromatography, m.p. 81°–83° C.; FAB MS $[M+1]^+$ $^{35}Cl$ 594.1.

EXAMPLE 38

Preparation of (+,−)-2-(3,4-dichlorophenyl)-4-[(4-fluoro-1-naphthalenyl)carbonyl]-1-[[[1-(phenylmethyl)-4-piperidinyl]amino]acetyl] piperazine

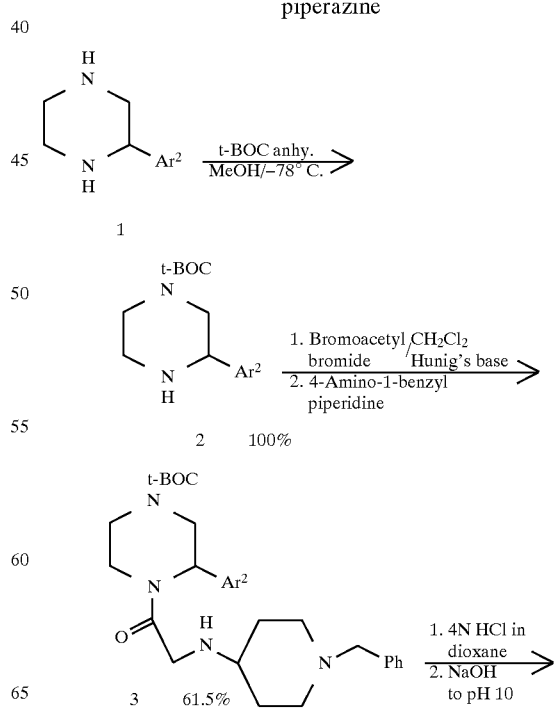

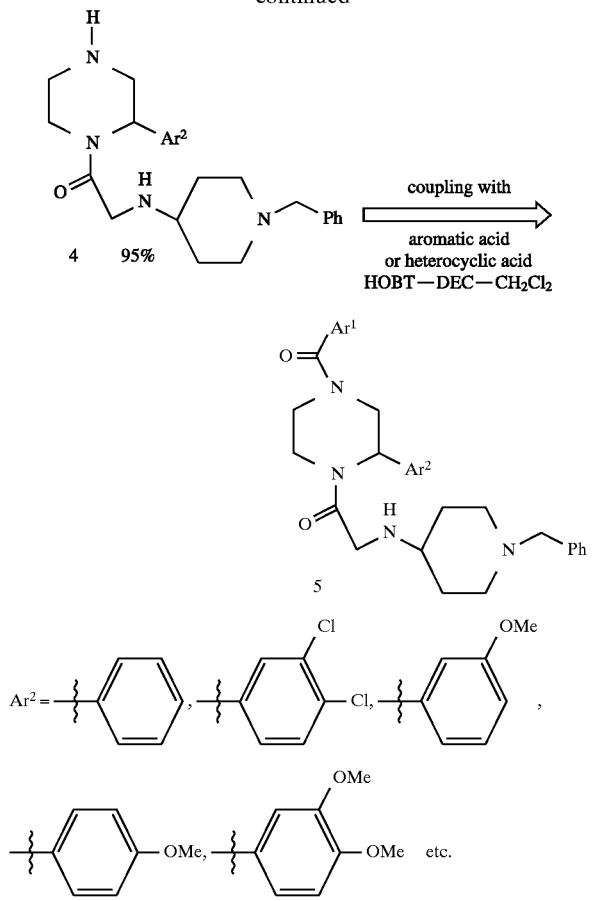

General Method

To a cooled solution of (+,−)-2-(3,4-dichlorophenyl) piperazine (1; $Ar^2$=3,4-dichlorophenyl) (20 g, 86.53 mmol) in MeOH (900 mL) at −78° C. was added dropwise a solution of t-BOC anhydride (19.47 g, 86.53 mmol) in MeOH (263 mL) over 3 h period under $N_2$. The solution was gradually warmed up to RT overnight. After reaction was complete, the solvent was evaporated and the residue was dried under high vacuum overnight to give 2 (28 g) as a white solid. ($Ar^2$=3,4-dichlorophenyl) FAB Mass [M+1]$^+$ $^{35}$Cl 331.2.

To a cooled solution of compound 2 (23.8 g, 71.85 mmol) in $CH_2Cl_2$ (500 mL) at −78° C. was added a solution of bromoacetylbromide (6.88 mL, 79.04 mmol) in $CH_2Cl_2$ (10 mL) through a dropping funnel under $N_2$ over a 10 min. period. After stirring at −78° C. for 3 h, TLC showed that the reaction was complete. To this cooled solution were added Hünig's base (13.76 mL, 79 mmol) and 4-amino-i-benzylpiperidine (29.30 mL, 143.7 mmol). It was kept at −78° C. for one hour then gradually warmed up to RT overnight. After completion $CH_2Cl_2$ (200 mL) was added and washed with brine (200 mL, 3×), dried over $MgSO_4$, filtered and concentrated to give a light brown residue of compound 3 (46 g) ($Ar^2$=3,4 -dichlorophenyl). Compound 3 was purified by flash chromatography on 400 g of flash grade silica gel, eluting with 3.5% $NH_3$—MeOH/$CH_2Cl_2$ to give 24.8 g (44.2 mmol, 61.5%) of pure compound 3 ($Ar^2$=3,4-dichlorophenyl). FAB MS [M+1]$^+$ $^{35}$Cl 561.3.

To a solution of compound 3 ($Ar^2$=3,4-dichlorophenyl) (16 g, 28.49 mmol) in $CH_2Cl_2$ (142.5 mL) at 0° C. was added 4N HCl-dioxane solution (71.24 mL, 284.9 mmol) through a dropping funnel. The reaction was gradually warmed up to RT and stirred for 4 h. After completion the solvents were evaporated to give a light yellow solid which was dissolved in $H_2O$ (400 mL) and brought to pH 10 with 1N NaOH. The product was extracted from basic aqueous solution with $CH_2Cl_2$(200 mL, 4×), dried over $MgSO_4$, filtered and concentrated to give compound 4 ($Ar^2$=3,4-dichlorophenyl) as a light yellow solid (12.5 g, 27.09 mmol, 95%). FAB MS [M+1]$^+$ $^{35}$Cl 461.1 Compound 4 was the key intermediate which was used to couple with various aromatic acid for the synthesis of many compounds.

To a solution of compound 4 ($Ar^2$=3,4-dichlorophenyl) (200 mg, 0.433 mmol) in $CH_2Cl_2$ (5 mL) were sequentially added 4-fluoro-1-naphthoic acid (84.8 mg, 0.433 mmol), HOBT (58.5 mg, 0.434 mmol), $Et_3N$ (0.634 mL, 0.455 mmol) and DEC (85 mg, 0.434 mmol) at RT. The reaction was stirred at RT under $N_2$ overnight. After completion the reaction was diluted with EtOAc (150 mL) and washed with brine (50 mL, 3×), dried over $MgSO_4$, filtered and concentrated to give a crude product 5 ($Ar^2$=3,4-dichlorophenyl, $Ar^1$=4-fluoro-1-naphthyl) which was purified by flash chromatography ( 50 g flash grade silica gel), eluting with 4% sat'd $NH_3$—MeOH in $CH_2Cl_2$ to give pure compound 5 Fab Mass [M+1]$^+$ $^{35}$Cl 633.2, m.p. 78°–81° C.

EXAMPLE 39

The following compounds were prepared according to the procedures described in Example 38. The key intermediate compound 4 ($Ar^2$=3,4-dichlorophenyl) was coupled with the appropriate aromatic acid to obtain the target compounds. Those compounds without melting points were prepared via parallel synthesis.

| | FAB and/or Cl MS [M + 1]$^+$ $^{35}$Cl | M.P. °C. |
|---|---|---|
| | 634/636 (M + 1)$^+$ for (4×$^{35}$Cl)/ (3×$^{35}$Cl + 1×$^{37}$Cl) | |

| | FAB and/or Cl MS [M + 1]+ 35Cl | M.P. °C. |
|---|---|---|
| ![structure with benzylpiperidine-NH-CH2-C(O)-N(piperazine with 3,4-dichlorophenyl)-C(O)-CH(Ph)2] | 655.1 | 70–73 |
| ![structure with benzylpiperidine-NH-CH2-C(O)-N(piperazine with 3,4-dichlorophenyl)-C(O)-naphthyl-N(CH3)2]<br>made pure from chiral enantiomer B<br>intermediate 4 analogous to Example 38 | 658 | Calcd. for<br>C37H41N5O2Cl2.3 HCl.3 H2O<br>C, 54.06; H, 6.13; N, 8.52<br>Found:<br>C, 54.28; H, 6.23; N, 8.77 |
| ![structure with benzylpiperidine-NH-CH2-C(O)-N(piperazine with 3,4-dichlorophenyl)-C(O)-(6-methyl-2-chloropyridyl)]<br>made pure from chiral enantiomer B<br>intermediate 4 analogous to Example 38 | 614 | Calcd. for<br>C30H31N5O2Cl4.2 HCl.2 H2O<br>C, 48.41; H, 5.01; N, 9.41<br>Found:<br>C, 48.16; H, 5.41; N, 9.30 |

What is claimed is:

1. A compound of the formula:

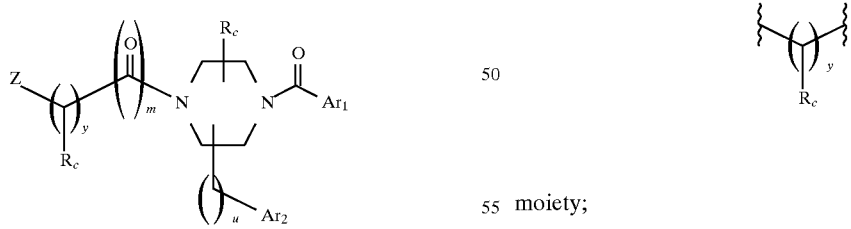

wherein u is 0 to 2;

m is 1, and y is 1 to 3; or m is 2, and y is 0;

and with the further proviso that no more than one $R_c$ is other than H in the moiety;

each $R_c$ is independently selected from the group consisting of H and $C_1$–$C_6$ alkyl;

each $R_a$ and $R_b$ is independently selected from the group consisting of H, $C_1$–$C_6$ alkyl, phenyl, substituted phenyl, benzyl, substituted benzyl and allyl; or $R_a$ and $R_b$ together are $C_3$–$C_6$ alkylene and are attached to the same nitrogen, so that $R_a$ and $R_b$ together with the nitrogen to which they are attached, form a 4 to 7 member ring;

each $R_1$ and $R_2$ is independently selected from the group consisting of H, $C_1$–$C_6$ alkyl, $CF_3$, $C_2F_5$, Cl, Br, I, F, $NO_2$, $OR_a$, CN, $NR_aR_b$, $$-\overset{O}{\underset{\|}{C}}-R_a, \quad -O-\overset{O}{\underset{\|}{C}}-R_a, \quad -O-\overset{O}{\underset{\|}{C}}-\overset{R_a}{\underset{|}{N}}-R_b, \quad -\overset{R_b}{\underset{|}{N}}-\overset{O}{\underset{\|}{C}}-OR_a,$$

$$-\overset{R_a}{\underset{|}{N}}-\overset{O}{\underset{\|}{C}}-R_b, \quad -\overset{O}{\underset{\|}{C}}-OR_a, \quad -\overset{O}{\underset{\|}{C}}-\overset{R_a}{\underset{|}{N}}-R_b, \quad -\overset{O}{\underset{\|}{S}}-R_a, \quad -\overset{O}{\underset{\|}{\underset{\|}{S}}}\overset{O}{=}R_a,$$

$$-SR_a, \text{ and } -\overset{O}{\underset{\|}{\underset{\|}{S}}}\overset{O}{=}NHR_a;$$

and where $R_a$ is not H in $$-\overset{O}{\underset{\|}{S}}-R_a, \quad -\overset{O}{\underset{\|}{\underset{\|}{S}}}\overset{O}{=}R_a \text{ or } -\overset{R_b}{\underset{|}{N}}-\overset{O}{\underset{\|}{C}}-OR_a;$$

or when $R_1$ and $R_2$ are on adjacent carbons on a ring, they can form wherein n' is 1 or 2;

each $R_3$ is independently selected from the group consisting of H, $C_1$–$C_6$ alkyl, $CF_3$, $C_2F_5$, $$-\overset{O}{\underset{\|}{C}}-R_a, \quad -O-\overset{O}{\underset{\|}{C}}-R_a, \quad -\overset{O}{\underset{\|}{C}}-\overset{R_a}{\underset{|}{N}}-R_b$$

Cl, Br, I, F, $OR_a$, $OCF_3$, and phenyl;

$Ar_1$ is $Ar_2$ is

Z is n is independently 0–2;

$m_2$=1–2; $n_3$ is 0–4;

each $R_e$ and $R_f$ is independently selected from the group consisting of H, $C_1$–$C_6$ alkyl, phenyl, substituted phenyl, benzyl, substituted benzyl and allyl; or $R_e$ and $R_f$ taken together with the carbon to which they are attached can also form a carbonyl group with the proviso that no more than one carbonyl group is in the moiety;

$n_5$ is 1;

$R_5$ is H or $C_1$–$C_6$ alkyl;

$R_6$ is H, $C_1$–$C_6$ alkyl, $C_3$–$C_6$ cycloalkyl, thienyl, pyridyl, isoxazoyl, or when $R_e$,$R_f$ taken together with the carbon atom to which they are attached form a carbonyl group and $n_3$ is 1, $R_6$ can also be —$OR_a$ wherein $R_a$ is not H;

and wherein substituted means 1 to 3 substituents independently selected from the group consisting of H, $C_1$–$C_6$ alkyl, $CF_3$, $C_2F_5$, OH, $OC_1$–$C_6$ alkyl, Cl, Br, I and F;

or any enantiomer thereof, or a pharmaceutically acceptable salt thereof.

2. A compound according to claim 1 wherein $R_e$ and $R_f$ are independently selected from the group consisting of H, $C_1$–$C_6$ alkyl and allyl, $n_3$ is 0–4, and $R_6$ is $C_1$–$C_6$ alkyl, $C_3$–$C_6$ cycloalkyl, thienyl, pyridyl, isoxazolyl, or wherein $R_e$ and $R_f$, taken together with the carbon to which they are attached, form a carbonyl group, $n_3$ is 1 and $R_6$ is —$OR_a$, wherein $R_a$ is not H;

or wherein $R_e$ and $R_f$, taken together with the carbon to which they are attached, form a carbonyl group, $n_3$ is 1 and $R_6$ is $C_1$–$C_6$ alkyl, $C_3$–$C_6$ cycloalkyl, thienyl, pyridyl, isoxazolyl.

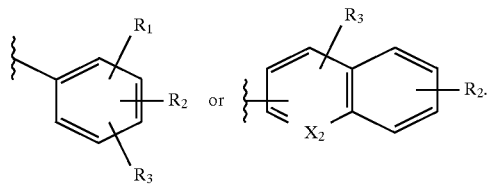

3. A compound according to claim 1 of the formula

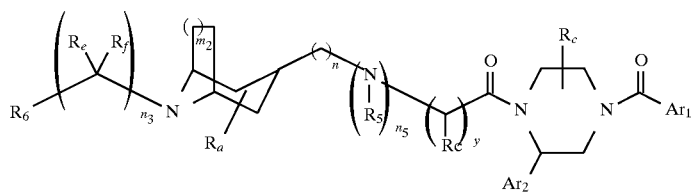

III wherein $Ar_1$ and $Ar_2$ are both

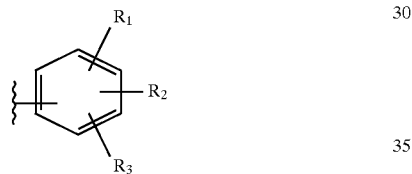

4. A compound selected from the group consisting of

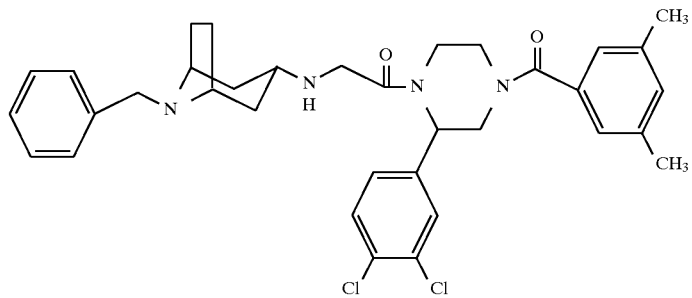

and

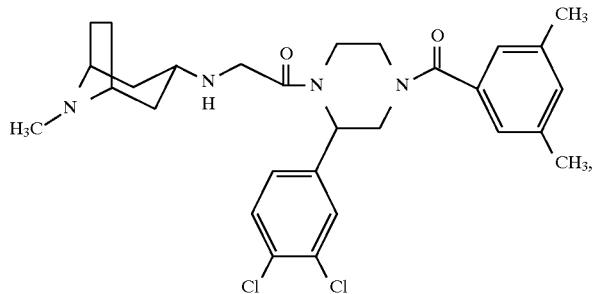

or any enantiomer thereof, or a pharmaceutically acceptable salt thereof.

5. A composition comprising a neurokinin antagonistic effective amount of a compound according to claim 1 and a pharmaceutically acceptable carrier material.

6. A method for treating asthma, bronchospasm, allergies, anxiety coughing or pain, which comprises administering a therapeutically effective amount of a compound according to claim 1 to a mammal in need of such treatment.

* * * * *